United States Patent
Chan et al.

(10) Patent No.: US 8,215,314 B2
(45) Date of Patent: Jul. 10, 2012

(54) PHOTOCHEMICAL TISSUE BONDING

(75) Inventors: Barbara Chan, Cambridge, MA (US); Timothy Shane Johnson, Jamaica Plain, MA (US); Irene E. Kochevar, Charlestown, MA (US); Mark Randolph, Chelmsford, MA (US); Robert W. Redmond, West Newton, MA (US); Jonathan M. Winograd, Sudbury, MA (US)

(73) Assignee: The General Hospital Corporation, Boston, MA (US)

( * ) Notice: Subject to any disclaimer, the term of this patent is extended or adjusted under 35 U.S.C. 154(b) by 872 days.

(21) Appl. No.: 10/732,032

(22) Filed: Dec. 9, 2003

(65) Prior Publication Data
US 2005/0038471 A1     Feb. 17, 2005

Related U.S. Application Data

(63) Continuation-in-part of application No. 10/691,180, filed on Oct. 21, 2003, now abandoned, which is a continuation-in-part of application No. 10/094,120, filed on Mar. 8, 2002, now Pat. No. 7,073,510, which is a continuation-in-part of application No. 09/900,504, filed on Jul. 6, 2001, now abandoned, which is a continuation-in-part of application No. 09/781,577, filed on Feb. 12, 2001, now Pat. No. 7,331,350.

(60) Provisional application No. 60/181,980, filed on Feb. 11, 2000.

(51) Int. Cl.
*A61B 19/00* (2006.01)

(52) U.S. Cl. ........................ 128/898; 606/214

(58) Field of Classification Search .................. 128/898; 522/13; 606/213–221
See application file for complete search history.

(56) References Cited

U.S. PATENT DOCUMENTS

| | | | | |
|---|---|---|---|---|
| 2,127,903 A | * | 8/1938 | Bowen | 606/154 |
| 127,109 A | | 11/1978 | Fourney et al. | |
| 4,127,109 A | * | 11/1978 | Fourney et al. | 128/899 |
| 4,662,884 A | * | 5/1987 | Stensaas et al. | 606/152 |
| 4,870,966 A | * | 10/1989 | Dellon et al. | 606/152 |
| 5,147,514 A | * | 9/1992 | Mechanic | 204/157.68 |
| 5,209,776 A | * | 5/1993 | Bass et al. | 106/124.1 |
| 5,292,362 A | * | 3/1994 | Bass et al. | 106/173.01 |

(Continued)

FOREIGN PATENT DOCUMENTS

CA    2278937 A1    6/1998

(Continued)

OTHER PUBLICATIONS

Bass and Treat, "Laser Tissue Surgery: A comprehensive review of current and future clinical applications", Lasers in Surgery and Medicine, 17:315-349.*

(Continued)

*Primary Examiner* — Paul Prebilic
(74) *Attorney, Agent, or Firm* — Edwards Wildman Palmer LLP; Peter C. Lauro, Esq.

(57) ABSTRACT

Photochemical tissue boding methods for bonding neural tissues include the application of a photosensitizer to a tissue and/or tissue graft, followed by irradiation with electromagnetic energy to produce a tissue seal. The methods are useful for tissue adhesion, such as in wound closure, tissue grafting, skin grafting, musculoskeletal tissue repair, ligament or tendon repair, neural repair, blood vessel repair and corneal repair.

12 Claims, 33 Drawing Sheets
(4 of 33 Drawing Sheet(s) Filed in Color)

U.S. PATENT DOCUMENTS

| | | | | |
|---|---|---|---|---|
| 5,374,515 | A | * | 12/1994 | Parenteau et al. ............... 435/1.1 |
| 5,376,376 | A | * | 12/1994 | Li ................................. 424/443 |
| 5,431,790 | A | * | 7/1995 | Nesburn et al. ........... 204/157.68 |
| 5,552,452 | A | * | 9/1996 | Khadem et al. ................. 522/63 |
| 5,565,551 | A | * | 10/1996 | Lewis et al. .................... 530/405 |
| 5,571,216 | A | * | 11/1996 | Anderson ...................... 128/898 |
| 5,616,562 | A | * | 4/1997 | Murphy et al. .................. 514/15 |
| 5,829,448 | A | * | 11/1998 | Fisher et al. ................... 128/898 |
| 5,844,016 | A | * | 12/1998 | Sawhney et al. ................ 522/13 |
| 5,917,045 | A | * | 6/1999 | Lewis et al. .................... 546/100 |
| 5,942,534 | A | | 8/1999 | Trauner et al. |
| 6,007,833 | A | | 12/1999 | Chudzik et al. |
| 6,017,466 | A | * | 1/2000 | Fujino et al. .............. 252/299.01 |
| 6,030,974 | A | * | 2/2000 | Schwartz et al. ............. 514/267 |
| 6,107,466 | A | | 8/2000 | Hasan et al. |
| 6,156,345 | A | | 12/2000 | Chudzik et al. |
| 6,607,522 | B1 | * | 8/2003 | Hamblin et al. .................. 606/8 |
| 6,773,699 | B1 | * | 8/2004 | Soltz et al. ................. 424/78.03 |
| 6,783,539 | B1 | * | 8/2004 | Timberlake et al. .......... 606/214 |
| 7,073,510 | B2 | * | 7/2006 | Redmond et al. ............. 128/898 |
| 7,331,350 | B2 | * | 2/2008 | Kochevar et al. ............. 128/898 |
| 2002/0006394 | A1 | | 1/2002 | Redmond et al. |
| 2002/0022588 | A1 | * | 2/2002 | Wilkie et al. ...................... 514/2 |
| 2002/0022606 | A1 | | 2/2002 | Kochevar et al. |
| 2005/0038471 | A1 | * | 2/2005 | Chan et al. .................... 606/214 |
| 2005/0095235 | A1 | * | 5/2005 | Austin et al. ............... 424/94.64 |
| 2009/0287313 | A1 | * | 11/2009 | Lowinger et al. .......... 623/23.72 |

FOREIGN PATENT DOCUMENTS

| | | |
|---|---|---|
| CA | 02255493 | 12/1998 |
| WO | WO 91/04073 | 4/1991 |
| WO | WO 99/65536 | * 12/1999 |

OTHER PUBLICATIONS

Hawley's Condensed Chemical Dictionary, 11<sup>th</sup> Edition (1987), Van Nostrand Reinhold Company, title page and p. 1015.*

Judy, M.M., L. Chen, L. Fuh, H. Nosir, R. Jackson, J. Matthews, D. Lewis, R. Utecht, D. Yuan. "Photochemical cross-linking of type 1 collagen with hydrophobic and hydrophyilic dyes.", SPIE., vol. 2682:53-55.

Riley J.N., T. Dsckson, D. Hou, P. Rogers, K. Mar., K. McNally-Heintzzelman, "Improved laser-assisted vascular tissue fusion using light-activated surgical adhesive in a porcine model", Biomed Sci Instrum 37:451-6, 2001.

Moser, D., J. Riley, B. Sorg, A Welch, K. McNally-Heintzellman, "New range of light-activated surgical adhesives for tissue repair", Biomed. Sci. Instruments: 37:441-449,2001.

U. Kumar, D. Albala, "Newer techniques in intracorporeal tissue approximation: suturing, tissue adhesives, and microclips", Urol. Clin. North. Am. 28(1): 15-21,2001.

Paper entitled: *Photochemical Sealing Improves Outcome Following Peripheral Neurorrhaphy*. Anne C. O'Neill MD, Mark A. Randolph MAS, Kenneth E. Bujold BS, Irene E. Kochevar PhD, Robert W. Redmond PhD, Jonathan M. Winograd MD Presented at: Smith Day, MGH Department of Orthopedic Surgery, May 2006.

Paper entitled: *Photochemical sealing of microsurgical neurorrhaphy improves functional recovery*. O'Neill AC*, Zeballos JL, Randolph MA, Kochevar IE, Redmond RW, Winograd JM. Presented at: American Society for Peripheral Nerve (ASPN), Tuscon, Arizona, Jan. 11-14, 2006.

Slides entitled: *Photochemical sealing of microsurgical neurorrhaphy improves functional recovery*. O'Neill AC*, Randolph MA, Bujold K.E., Kochevar IE, Redmond RW, Winograd JM. Presented at: Massachusetts General Hospital May 2006.

Paper and slides entitled: *Preparation and Integration of Nerve Conduits Using a Photochemical Technique*. Anne C. O'Neill MD, Mark A. Randolph MAS, Kenneth E. Bujold BS, Irene E. Kochevar PhD, Robert W. Redmond PhD, Jonathan M. Winograd MD Presented at: Plastic Surgery Research Counsel, Stamford, CA Jun. 20-23, 2007 and the Irish Association of Plastic Surgeons meeting; May 10-12, 2007.

Kuo, Paul, "Tissue Fusion." Laser in Maxillofacial Surgery and Dentistry, 175-178.

Donkerwolcke, M., et al., "Tissues and Bone Adhesives-Historical Aspects." Biomaterials, 19:1461-1466, 1998.

Musa OM, Choi SY, Homer JH, Newcomb M., "Absolute Rate Constants for Alpha-Amide Radical Reactions."J. Org. Chem. Feb. 6, 1998; 63(3): 786-793.

Prause, JU., Kriegbaum, NJ. et al., Rose Bengal Score-A possible key parameter when evaluating disease level and progression in Primary Sjogren's Syndrome., J. Autoimmunity 1989; 2: 501-507.

Toriumi, DS., et al. (1990) "Histotoxicity of cyanoacrylate tissue adhesives. A comparative study." Arch. Otoloaryngol. Head. Neck Surg., 116: 546-550.

Abergel et al., "Skin closure by Nd: YAG laser welding", May 1986, J. Am. Acad. Dematol. 14:810-814.

Barton et al., "The Generation and Reactivity of Oxygen . . . ", Jan. 1991, Tetrahedron Lett. 32: 6869-6872.

Gandin et al., "Quantum Yield or Singlet Oxygen . . . ", Mar. 1983, Photochem Photobiol 37:271-278.

Henrick et al., "Organic tissue glue in the closure of cataract incisions in rabbit eyes", Sep. 1991, J. Cataract Refract Surg. 17:551-555.

Melki et al., "Photochemical Tissue Repair (Welding) of Clear Cornea Incisions", Mar. 1999 IVOS, vol. 40, No. 4: s340, Abstract 1803-B711.

Wider et al., "Skin Closure with Dye-Enhanced . . . ", Dec. 1991 Plastic Reconstr. Surg. 88: 1018-1025.

Houshian S., Tscherning, T., Riegels-Nielsen, P., (1998), "The Epidemiology of Achilles Tendon Rupture in a Danish County", Injury 29(9): 651-654.

Boivin et al. (1990) tetrahedron Lett 31: 6869-672.

Oz, M., et al., "Indocyanine Green Dye Enhanced Welding with a Diode Laser", Surgical Forum: Vascular Surgery, 316-319.

Chan, B.P., et al., Enhancement of Porcine Skin Graft Adherence Using a Light-Activated Process, Journal of Surg. Res., 108(1): Abstract, Nov. 2002.

Kamegaya, Y., et al., Evaluation of Photochemical Tissue Bonding for Closure of Skin Incisions and Excisions, Lasers in Surgery and Medicine, 37:264-270, Sep. 2005.

White, R.A., Technical Frontiers for the Vascular Surgeon: Laser Anastomotic Welding and Angioscopy-Assisted Intraluminal Instrumentaion, Journal of Vascular Surgery, 5(4): 673-680, Apr. 1987.

Kiernan, J.A., Formaldehyde, Formalin, Paraformaldehyde and Glutaraldehyde: What They Are and What They Do, Microscopy Today, Jan. 8-12, 2000.

Lowe, S.W., et al., p53-Dependent Apoptosis Modulates the Cytotoxicity of Anticancer Agents, Cell, vol. 74, 957-967, Sep. 1993.

Lowe, S.W. et al., p53 is Required for Radiation-Induced Apoptosis in Mouse Thmocytes, Nature, vol. 362, 847-849, Apr. 1993.

Nguyen, D.M., et al., Gene Therapy for Lung Cancer: Enhancement of Tumor Suppression by a Combination of Sequential Systemic Cisplatin and Adenovirus-Mediated p53 Gene Transfer, Journal of Thoracic and Cardiovascular Surgery, vol. 112, No. 5: 1372-1377, Nov. 1996.

Chiniwala, H. A., et al., Degenerative Tear of Tendo Achilles: Treatment by Primary Lengthening and Resuturing, http://www.bhj.org/journa1/1999_4102_apr99/original_268.html, Apr. 1999.

Soukos, N.S., et al., Targeted Antimicrobial Photochemotherapy, Antimicrobial Agents and Chemotherapy, vol. 42, No. 10, 2595-2601, Oct. 1998.

Milik, Z., et al., New Trends in Photobiology (Invited Review) Bactericidal Effects of Photoactivated Porphyrins—An Alternative Approach to Antimicrobial Drugs, Journal of Photochemistry and Photobiology, B: Biology, 5, 281-293, May 1990.

Proceedings of the American Association for Cancer Research, vol. 35, 692-693, Apr. 1994.

Hoekstra, A.H. Struszcyk, O. Kivekas, "Percutaneous microcrystlline chitosan application for sealing arterial puncture sites." Biomaterials, 19:1467-1471, Aug. 1998.

Riley J.N., T. Dsckson, D. Hou, P. Rogers, K. March, K. McNally-Heintzzelman, "Improved laser-assisted vascular tissue fusion using light-activated surgical adhesive in a porcine model", Biomed Sci Instrum 37:451-6, Jul. 2001.

Moser, D., J. Riley, B. Sorg, A Welch, K. McNally-Heintzellman, "New range of light-activated surgical adhesives for tissue repair", Biomed. Sci. Instruments: 37:441-449, Jul. 2001.

U. Kumar, D. Albala, "Newer techniques in intracorporeal tissue approximation: suturing, tissue adhesives, and microclips", Urol. Clin. North. Am. 28(1): 15-21, Feb. 2001.

McNally, K., B. Sorg, A. Welch, "Novel solid protein soldier designs for laser-assisted tissue repair." Lasers Surg. Med. 27(2): 147-157, Jul. 2000.

Bleustein, C., C. Walker, D. Felsen, D. Poppas, "Semi-solid albumin soldier improved mechanical properties for laser tissue welding." Lasers Surg. Med. 27(2): 140-146, Jul. 2000.

Sorg, B., K. McNally, A. Welch, Biodegradable polymer film reinforcement of an indocyanine green-doped liquid albumin soldier for laser-assisted incision closure. Lasers Surg. Med. 27(1): 73-81, Jul. 2000.

McNally, K., B. Sorg, E. Chan, A. Welch, J. Dawes, E. Owen, Optimal parameters for laser tissue soldiering: II. Premixed versus separated dye-soldier techniques.: Lasers Surg. Med. 26(4): 346-356, May 2000.

Tanaka, T., S. Furutani, M. Nakamura, T. Nishida, "Changes in extracellular matrix components after excimer laser photoablation in rat cornea." Jpn. I. Opthalmol. 43(5): 348-354, Oct. 1999.

Lauto, A., I. Kerman, M. Ohebshalon, D. Felsen, D. Poppas "Two-laver film as a laser soldering bi+2omaterial." Lasers Surg. Med. 25(3): 250-256, Dec. 2000.

G. Timberlake, A. Patmore, A. Shallal, D. McHugh, J. Marshall, "Thermal and infrared diode laser effects on indocyanine green treated corneal collagen." Presented at the SPIE annual meeting, Jan. 19, 1993, paper 1882-28.

G. Timberlake, A. Patmore, A. Shellal, D. McHugh, J. Marshall, "Thermal and infrared diode laser effects on indocyanine green treated corneal collagen." Presented at the SPIE annual meeting, Jan. 19, 1993, paper 1882-28.

Goins et al., "Photodynamic biological tissue glue to enhance . . . " J. Cataract Refract. Surg., vol. 23, Nov. 1997: 1331-1338.

Quinn, James et al., "A Randomized Trial Comparing Octylcyanoacrylate Tissue Adhesive and Sutures in the Management of Lacerations." JAMA 277, #19: 1527-1530, May 1997.

Oz, Mehhmet, et al., "Comparison of laser-assisted fibrinogen-bonded and sutured canine arteriovenous anastomoses." Surgery, 112 #1: 76-83, Jul. 1992.

Campion, Edmund, et al., "Repair of Peripheral Nerves with the Argon Laser." The Journal of Bone and Joint Surgery, vol. 72-A #5: 715-723, Jun. 1990.

Kuo, Paul, "Tissue Fusion." Laser in Maxillofacial Surgery and Dentistry, 175-178, (1997).

Donkerwolcke, M., et al., "Tissues and Bone Adhesives—Historical Aspects." Biomaterials, 19:1461-1466, 1998.

Bingley, John et al., "Late Complications of Tissue Glues in Aortic Surgery." Ann. Thorac. Surg. 69: 1764-1768, 2000.

Tang, J., et al., "Original Articles Morphological Analysis of Microarterial Media Repair After 830 nm Diode Laser Assisted End to End Anastomosis: Comparison with Conventional Manual Suture." Lasers in Medical Science 12: 300-305, 1997.

Lemp, MA. Report of the National Eye Institute/Industry Workshop on clinical Trials in dry eyes. CLAO J. (1995) 21:221-232.

Musa OM, Choi SY, Homer JH, Newcomb M., "Absolute Rate Constants for Alpha-Amide Radical Reactions."•J. Org. Chem. Feb. 6, 1998; 63(3): 786-793.

Al-Maharik, N., Engman, L., Malmstrom, J., Schiesser, CH, J. Org. Chem. Sep. 21, 2001;66(19): 6286-90.

Chaulk, S.G., Pezacki, JP., MacMillan, AM., Biochemistry Aug. 29, 2000; 39(34): 10448-53.

Aveline, BM., Redmond, RW., Photochem Photobiol. Sep. 1998;68(3): 266-75.

Epe, B., Ballmaier, D., Adam, W., Grimm, GN, Saha-Moller, CR., Nucleic Acids Res., May 1, 1996;24(9): 1625-31.

Reszka, K.J., Chignell, CF., Photochem. Photobiol. Nov. 1994; 60(5):450-4.

Lepri, E., Castagnino, E., Binaglia, L., Giampietri, A., Corsano S., Fioretti MC., Arzneimittelforschung Mar. 1993; 43(3):381-3.

Mulroy, L., Kim, J., Wu I., Scharper, P., Melki, SA., Azar, DT., Redmond, RW., Kochevar, IE., Invest Opthalmol Vis Sci Oct. 2000; 41(11):3335-40.

Khadem, J., Truong, T., Ernest, JT., Cornea Sep. 1994; 13(5):406-10.

Manning, FJ., Wehrly, SR., Foulks, GN., Ophthalmology Dec. 1995; 102(12): 1953-1957.

Tabery, HM., Acta Ophthalmol. Scand. Apr. 1998; 76(2): 142-145.

Gelli, R., et al., "Vessel Wall Recovery After Diode Laser Assisted Microvascular Anastomosis: Clinical and Histologic Analysis and Long Term Follow Up", Journal of Reconstructive Microsurgery 13, #3: 199-205, Apr. 1997.

Oz, M., et al., "Indocyanine Green Dye Enhanced Welding with a Diode Laser", Surgical Forum: Vascular Surgery, 316-319, (1989).

Bass, L., et al., "Changes in Type 1 Collagen Following Laser Welding", Lasers in Surgery and Medicine 12: 500-505 (1992).

Bailes, J., et al., "Review of Tissue Welding Applications in Neurosurgery", Microsurgery 8: 242-244 (1987).

Mulroy, L. et al., "Photochemical Tissue bonding for Corneal Repair and Transplants", Photochemistry and Photobiology, 1999, vol. 69, Supp. p. 41S-42S.

Merguerian, Paul A., et al., "Non-Thermal Ureteral Tissue Bonding: Comparison of Photochemical Collagen Crosslinking with Thermal Laser Bonding", Proceedings of SPIE—The International Society for Optical Engineering, 1999, vol. 3590, pp. 194-202.

Aveline, Beatrice A., et al., "Exclusive Free Radical Mechanisms of Cellular Photosensitization", Photochemistry and Photobiology, 1998, vol. 68, No. 3, pp. 266-275.

Saunders, "Tissue welding a new kind of laser surgery uses molecules to stitch together wounds", Jan. 19, 1998; pp. 16-17, Science News Biology, http://www.discover.com/science_news/bioscience.html.

Judy, M.M., L. Chen, L. Fuh, H. Nosir, R. Jackson, J. Matthews, D. Lewis, R. Utecht, D. Yuan. "Photochemical cross-linking of type 1 collagen with hydrophobic and hydrophyilic dyes.", SPIE., vol. 2682: 53-55, May 1996.

Hoekstra, A.H. Struszcyk, O. Kivekas, "Percutaneous microcrystlline chitosan application for sealing arterial puncture sites." Biomaterials, 19:1467-1471, 1998.

Riley J.N., T. Dsckson, D. Hou, P. Rogers, K. March, K. McNally-Heintzzelman, "Improved laser-assisted vascular tissue fusion using light-activated surgical adhesive in a porcine model", Biomed Sci Instrum 37:451-6, 2001.

Moser, D., J. Riley, B. Sorg, A Welch, K. McNally-Heintzellnnan, "New range of light-activated surgical adhesives for tissue repair", Biomed. Sci. Instruments: 37:441-449, 2001.

U. Kumar, D. Albala, "Newer techniques in intracorporeal tissue approximation: suturing, tissue adhesives, and microclips", Urol. Clin. North. Am. 28(1): 15-21, 2001.

McNally, K., B. Sorg, A. Welch, "Novel solid protein soldier designs for laser-assisted tissue repair." Lasers Surg. Med. 27(2): 147-157, 2000.

Bleustein, C., C. Walker, D. Felsen, D. Poppas, "Semi-solid albumin soldier improved mechanical properties for laser tissue welding." Lasers Surg. Med. 27(2): 140-146, 2000.

Sorg, B., K. McNally, A. Welch, Biodegradable polymer film reinforcement of an indocyanine green-doped liquid albumin soldier for laser-assisted incision closure. Lasers Surg. Med. 27(1): 73-81, 2000.

McNally, K., B. Sorg, E. Chan, A. Welch, J. Dawes, E. Owen, Optimal parameters for laser tissue soldiering: II. Premixed versus separate dye-soldier techniques.: Lasers Surg. Med. 26(4): 346-356, 2000.

Tanaka, T., S. Furutani, M. Nakamura, T. Nishida, "Changes in extracellular matrix components after excimer laser photoablation in rat cornea." Jpn. I. Opthalmol. 43(5): 348-354, 1999.

Lauto, A., I. Kerman, M. Ohebshalon, D. Felsen, D. Poppas, "Two-layer film as a laser soldering bi+2omaterial." Lasers Surg. Med. 25(3): 250-256, 1999.

G. Timberlake, A. Patmore, A. Shallal, D. McHugh, J. Marshall, "Thermal and infrared diode laser effects on indocyanine green treated comeal collagen." Presented at the SPIE annual meeting, Jan. 19, 1993, paper 1882-28.

Kuo, Paul, "Tissue Fusion." Laser in Maxillofacial Surgery and Dentistry, 175-178, 1997.

Musa OM, Choi SY, Homer JH, Newcomb M., "Absolute Rate Constants for Alpha-Amide Radical Reactions." J. Org. Chem. Feb. 6, 1998; 63(3): 786-793.
Kim J., Foulks, GN., Cornea May 1999; 18(3): 328-332.
Arch Ophthalmol Jul. 1992; 110(7):984-993.
Tseng, SC., Zhang, SH., Cornea Jul. 1995; 14(4): 427-435.
Wander, AH., Neumeister, RD., Tschismadia, I., Choromokos, EA., Madukawa, T., Cornea 1985-1986; 4(1) 8-13.
Norn, MS., Acta Ophthalmol (Copenh) 1967; 45(3): 347-358.
Prause, JU., Kriegbaum, NJ. et al., Rose Bengal Score—A possible key parameter when evaluating disease level and progression in Primary Sjogren's Syndrome., J. Autoimmunity 1989; 2: 501-507.
Van Bijsterveld, OP. Diagnostic tests in the Sicca Syndrome, Arch Ophthal. 1969; 82:10-14.
Toriumi, DS., et al. (1990) "Histotoxicity of cyanoacrylate tissue adhesives. A comparative study." Arch. Otoloaryngol. Head Neck Surg., 116: 546-550.
Fujita T., et al. (2000) "Successful preservation of human skin by vitrification.", J. Burn Care Rehabil. 21: 304-309.
Forseth D.M., et al. (1992), "The current status of cyanoacrylate and fibrin tissue adhesives", J. Long Term Eff. Med. Implants 2(4): 221-233.
Chan, et al., "Photochemical tissue bonding in skin grafting—An ex vivo study." 29$^{th}$ Annual meeting of the American Society of Photobiology, (Jul. 7$^{th}$ & 12$^{th}$, 2001).
J.D. Spikes, "Photodynamic Action: From Paramecium to Photochemotherapy", Photochemistry and Photobiology, vol. 65 Special Issue, May 1997, 65S: 142-147S.
Bass & Treat (1995), "Laser Tissue Welding: A comprehensive review of current and future clinical applications", Lasers Surg. Med. 17:315-349.
Dahlstrom, K.K., et al., (1991), "The use of Autologous Fibrin Adhesive in Skin Transporation", Plastic and Reconstructive Surgery 89(5): 968-972.
Abergel et al., "Skin closure by Nd:YAG laser welding", May (1986), J. Am. Acad. Dematol. 14:810-814.
Aveline et al., "Photochemistry of the Nonspecific Hydroxyl Radical Generator, N-Hydroxypyridine-2(1H)-thione", Oct. 23, 1996, J. Am. Chem. Soc. 118:10113-10123.
Barton et al., "The Generation and Reactivity of Oxygen . . . ", Jan. (1991), Tetrahedron Lett. 32: 6869-6872.
Chuck et al. "Dye-enhanced Laser Tissue Welding", Lasers in Surgery and Medicine 9: 471-477 (1989).
Cilesiz et al., "Controlled Temperature Tissue Fusion . . . ", (1997) Lasers Surg. Med 21: 269-286.
Diestelhorst et al., "Clinical dose-Regimen with Latanoprost, . . . ", Survey of Ophthalmology, vol. 414, supp. 2, Feb. 1997: s77-s81.
Gandin et al., "Quantum Yield or Singlet Oxygen . . . ", Mar. (1983), Photochem Photobiol 37:271-278.
Goins et al., "Relative Strength of Photodynamic . . . ", J. Cataract Refract. Surg., vol. 24, Dec. 1998: 1566-1570.
Gollnick & Schenck, Mechanism and Stereoselectivity of . . . , (1964) Pure Appl. Chem. 9: 507-525.
Henrick et al., "Organic tissue glue in the closure of cataract incisions in rabbit eyes", Sep. (1991), J. Cataract Refract Surg. 17:551-555.
Judy et al., "Gel electrophoretic studies of photochemical . . . ", (1994) Proc SPIE—Int. Soc. Opt. Eng. 2128: 506-509.
Katol et al., "Aggregation of Collagen Exposed to UVA . . . ", Photochemistry and Photobiology, vol. 59, No. 3: 343-349, 1994.
Khadem et al., "Photodynamic Biologic Tissue Glue", Cornea, vol. 13, No. 5, (1994): 406-410.
Khodadoust, "Tissue Adhesives in Opthalmology", Surgical Pharmacology of the Eye (1985): 223-234.
Lewis et al., "Dimeric Non-Azo Naphthalimides and Used for Same," US 5,917,045, issued Jun. 29, 2000 (filing date of Jun. 7, 1995).
Massicotte et al., "Effects of Endogenous Absorption in Human . . . ", (1998) Lasers in Surgery and Medicine 23: 18-24.
Melki et al., "Photochemical Tissue Repair (Welding) of Clear Cornea Incisions", Mar. (1999) IVOS, vol. 40, No. 4: s340, Abstract 1803-B711.
Mulroy et al., "Photochemical Tissue Bonding for Corneal Repair and Transplatns", 27$^{th}$ Annual Meeting of the American Society for Photobiology, Abstract MPM-E21 (1999).

Oz et al., "Tissue soldering by use of indocyanine . . . ", J. Vascular Surgery, vol. 11, No. 5, (1990): 718-725.
Ramshaw et al., "Methylene blue sensitized . . . ", Biochimica et Biophysica Acta 1206, (1994): 225-230.
Shigemitsu et al., "The utilization of a biological adhesives for wound . . . ", (1997) International Opthalmology 20: 323-328.
Spoerl et al., "Induction of Cross-links in Cornea Tissue", Exp. Eye Res. (1998) 66: 97-103.
Stewart et al., "Laser assisted Vascular . . . ", (1996) Lasers in Surgery and Medicine 19: 9-16.
Poppas et al., "Temperature-Controlled Laser . . . ", (1996) Lasers in Surgery and Medicine 18: 335-344.
Wider et al., "Skin Closure with Dye-Enhanced . . . ", Dec. (1991) Plastic Reconstr. Surg. 88: 1018-1025.
Timberlake et al., "Corneal Laser Welding Using a Light-Activated Protein Crosslinking Dye", Investigative Ophthalmology & Visual Science 38(4) S510, Mar. 15, 1997.
Poppas et al., "Human Albumin solder supplemented . . . ", (1996) Lasers in Surgery and Medicine 19: 360-368.
Best, TM., Garrett, WE, Jr., "Basic Science of Soft Tissue: Muscle and Tendon", in DeLee, JC, Drez, D. (eds): Orthopaedic Sports Medicine. WB Saunders, Philadelphia: 1-45, 1994.
Bosch U., Kasperczyk, WJ., Oestern, HJ., Tsucherne, H., (1994), "The patellar tendon graft for PCL reconstruction. Morphological Aspects in a Sheep Model", Acta Orthop Belg 60 suppl: 57-61.
Davis, JJ., Mason, KT, Clark, DA., (1999), "Achilles tendon ruptures stratified by age, race and cause of injury among active duty U.S. Military members", Mil Med 164(12): 872-873.
Houshian S., Tscheming, T., Riegels-Nielsen, P., (1998), "The Epidemiology of Achilles Tendon Rupture in a Danish County", Injury 29(9): 651-654.
Judy, MM., Matthews, JL., Boriack, RL., Burlacu, A., Lewis, DE, Utech, RE., (1993b) "Photochemical Cross-linking of Type I Collagen with Brominated 1,8-naphthalimide dyes and visible light", SPIE 1882: 221-4.
Judy, MM., Mathews, JL., Boriack, RL., Burlacu, A., Lewis, DE., Utech, RE., (1993b) "Heat-free photochemical tissue welding with 1, 8-naphthalimides dyes using visible (420nm) light", SPIE Proc. 1876: 175-9.
Maj, Francis, Kilkelly, FX., Choma, TJ., (1996), "Tendon repair by laser welding: A histologic and biomechanical comparision and sutute repair with CO2 and Argon lasers", Laser Surg. Med. 19: 487-491.
Koh, WI, Lim, BH., (1999), "Soft Tissue Complications Following Kirschner Wire Fixation for Fusion of Basal Joint Arthritis", Hand Surgery 4(2): 197-202.
Lambert, CR., Kochevar, IE., (1997), "Electron Transfer Quenching of the Rose Bengla Triplet State", Photochem Photobiol. 66(1): 15-25.
Leppilahti, J., Orava, S., (1998) "Total Achilles Tendon Rupture. A Review", Sports Med 25(2): 79-100.
Maffulli, N., Waterston, SW., Squair, J., Reaper, J., Douglas, AS., (1999), "Changing Incidence of Achilles Tendon Rupture in Scotland: a 15 year study", Clin J. Sport Med. 9(3): 157-160.
Mulroy, L., Kim, J., WU, I., Scharper, P., Melski, SA., Azar, DT., Redmond, RW., Kochevar, IE., (2000), "Photochemical Kertodesmos for Repair of Lamellar Corneal Incisions", Invest Ophthal Vis Sci,41: 3335-3340.
Reddy, GK., Stehno-Bittel, L., Enwemeka, CS., (1998a), "Laser Photostimulation of Collegen Production in Healing Rabbit Achilles Tendons", Laser Surg Med 22: 281-287.
Reddy, GK., Stehno-Bittel, L., Enwemeda, CS., (1998b), "Biochemistry and Biomechanics of Healing Tendon: Part II. Effects of Combined Laser Therapy and Electrical Stimulation", Med Sci Sports Exerc 30(6): 794-800.
Shereff. (ed) (1993), Atlas of Foot and Ankle Surgery, WB Saunders, Philadelphia: 304-311.

Shimo, K., Nakata, K., Horibe, S., Inoue, M., Nakagawa, S. (1993), "Quantitative Evaluation After Arthroscopic Anterior Cruciate Ligament Reconstructions. Allgraft versus Autograft", Am J. Sports Med. 21(4): 609-616.

Stiel H., Teuchner, K., Paul, A., Leupold, D., Kochevar, IE., (1996), "Quantitative Comparison of Excited State Properties and Intensity-dependent Photosensitization by Rose Bengal", J. Photochem Photobiol 33: 245-254.

Barak et al., (1997) Surv. Opthalmol 42 Supp. 1: S77-81.

Barton et al. (1991) Tetrahedron Lett 32: 311-314.

Boivin et al. (1990) tetrahedron Lett 31: 6869-672. 1-1.

Henrick et al., (1987) J. Cataract Refract Surg 13: 551-553.

Annual Meeting of the American Society for Photobiology, Abstract-SPM-G24 (1997).

L. Mulroy et al., "Photochemical Keratodesmos for Repair or Lamellar Corneal Incisions", Investigative Ophthalmology & Visual Science, Oct. 2000, vol. 41, No. 11:3335-3340.

Detweiler, M., et al., "Sutureless and Reduced Suture Anastomosis of Hollow Vessels with Fibrin Glue: A Review", Journal of Investigative Surgery 12: 245-262 (1999).

Dunn, C. et al., "Fibrin Sealant: A Review of its Use in Surgery and Endoscopy", Drugs 58, #5: 863-886, No. 1999.

Bernard, L. et al., "A Prospective Comparision of Octyl Cyanoacrylate Tissue Adhesive (Dermabond) and Suture for the Closure of Excisional Wounds in Children and Adolescents", Arch Dermatol 137: 1177-1180, Sep. 2001.

Oz, M., et al., "Indocyanine Green Dye Enhanced Welding with a Diode Laser", Surgical Forum: Vascular Surgery, 316-319, 1989.

Saunders, "Tissue Welding, A New Kind of Laser Surgery Uses Molecules to Stitch Together Wounds", Jan. 19, 1998; pp. 16-17, Science News: Biology, http://www.discover.com/science_news/bioscience.html.

* cited by examiner

A

B

A

B

A

B

A

B

A

B

A

B

A

B

Method 1 – Cuff approach

Method 2 – Conduit approach

PHOTOCHEMICAL TISSUE BONDING

CROSS-REFERENCE TO RELATED APPLICATIONS

This is a continuation-in-part of U.S. application Ser. No. 10/691,180, filed Oct. 21, 2003, now abandoned, which is a continuation-in-part of U.S. application Ser. No. 10/094,120, filed Mar. 8, 2002, now U.S. Pat. No. 7,073,510, which is a continuation-in-part of U.S. application Ser. No. 09/900,504, filed Jul. 6, 2001, now abandoned, which is a continuation-in-part application of U.S. application Ser. No. 09/781,577, filed Feb. 12, 2001, now, U.S. Pat. No. 7,331,350, claiming priority to U.S. Provisional Application Ser. No. 60/181,980, filed Feb. 11, 2000, the contents of which are incorporated herein by reference. Reference is also made to PCT application No. PCT/US01/40093, filed on Feb. 12, 2001 and published on as PCT Publication No. WO 01/58495 on Aug. 16, 2001, claiming priority to U.S. Provisional Application Ser. No. 60/181,980, filed Feb. 11, 2000, the contents of which are incorporated herein by reference. Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported by the government, in part, by grants from the Department of Defense Medical Free Electron Laser Program, Award Nos. N0014-94-1-0927 and F49620-01-1-0014, the Department of Defense DAMD Program, Award No. 17-02-2-0006, the AFOSR, Award No. F49620-01-1-0014, and the Office of Naval Research, award number N000149910617. The government may have certain rights to this invention.

FIELD OF THE INVENTION

The present invention relates to methods of photochemical tissue bonding for use in tissue adhesion, such as in wound closure, tissue grafting, skin grafting, musculoskeletal tissue repair, ligament or tendon repair, neural repair, blood vessel repair and corneal repair. The present invention further relates to methods of photochemical tissue bonding for use in tissue adhesion, wherein a graft comprising a synthetic tissue substitute, engineered tissue or natural biomaterial is adhered to a host tissue.

BACKGROUND

Traditional wound closure methods, such as staples and sutures, have numerous drawbacks, including the possible occurrence of inflammation, irritation, infection, wound gap, and leakage. The cosmetic results of the use of staples and sutures can also be undesirable. In corneal applications, sutures often produce astigmatism due to uneven suture tension. In tissue grafting techniques, sutures can lead to a variety of complications in wound healing, including foreign body responses that cause scarring. Repair of injuries to tendons and ligaments involve an additional component whereby the wound must return to functional integrity, which would be severely compromised by the presence of scar tissue or the failure of sutures. Traditional wound closure and/or tissue adhesion methods suffer from a number of drawbacks that are addressed by the present invention.

Possible alternatives to sutures include hemostatic adhesives, such as fibrin sealants (Henrick et al. (1987) *J Cataract Refract Surg* 13:551-553; Henrick et al. (1991) *J Cataract Refract Surg* 17:551-555), cyanoacrylate adhesives (Shigemitsu et al. (1997) International *Ophthalmology* 20:323-328), and photodynamic tissue glue, composed of a mixture of riboflavin-5-phosphate and fibrinogen, which has been reported to close cataract incisions and attach donor cornea in corneal transplants (Goins et al. (1997) *J Cataract Refract Surg* 23:1331-1338; Goins et al. (1998) *J Cataract Refract Surg* 24:1566-1570; U.S. Pat. No. 5,552,452). In addition, temperature-controlled tissue welding has been attempted in bovine cornea and rat intestine (Barak et al. (1997) *Surv Ophthalmol* 42 Supp.1:S77-81; Cilesiz et al. (1997) *Lasers Surg Med* 21:269-86). Photochemical tissue welding of dura mater has also been reported, using 1,8 naphthalimides irradiated with visible light (Judy et al. (1993) *Proc. SPIE—Int. Soc. Opt. Eng.* 1876:175-179).

Tissue grafts and/or tissue substitutes (e.g., extracellular matrix-based scaffolds, such as collagen and proteoglycan, and/or other engineered tissue implants) are important components used in structural tissue engineering. Although many tissue grafts and/or substitutes are made of naturally occurring biomaterials, these structures, once implanted, do not attach well to the target tissue and can lack the ability to hold sutures. As a result, additional support material, such as silicon tubing, is implanted for further support and integration of the implant with the target tissue. The disadvantage of this method is that a second surgical procedure is often required for the removal of the support material once the implants become integrated with the host tissue.

In particular, tissue grafts comprising skin grafts and/or skin substitutes are widely used in surgical procedures such as skin transplantation, burn and ulcer wound management and plastic surgery. Current fixation aids for grafting mainly consist of mechanical and adhesive means (Bass & Treat (1995) *Lasers Surg Med* 17: 315-49). Surgical sutures and staples mechanically hold the tissue in position while tissue and fibrin glues chemically/biochemically bond the graft to the host. However, the use of sutures and staples has low aesthetic/cosmetic value and may lead to foreign-body reactions as well as wound complications (Bass & Treat (1995) *Lasers Surg Med* 17: 315-49). The use of tissue glues such as cyanoacrylate provides excellent binding strength but results in persistent inflammation and foreign body giant cell reaction (Forseth et al. (1992) *J Long Term Eff Med Implants* 2(4): 221-33, Toriumi et al. (1990) *Arch Otololaryngol Head Neck Surg* 116: 546-550). Although the use of autogenous fibrin glue eliminates the foreign-body reactions and the associated complications, it elicits other problems. Firstly, it is costly and time-consuming to extract and purify autogenous fibrinogen from the patient's blood (Dahlstrom et al. (1991) *Skin Transplantation* 89(5): 968-72) and secondly, the mechanical outcome is not satisfactory since the breaking strength at the interface was less than 0.2N/cm² (Dahlstrom et al. (1991) *Skin Transplantation* 89(5): 968-72).

Tendon and ligament injuries, including Achilles tendon rupture (Davis et al. (1999) *Mil Med* 164(12): 872-3; Maffulli et al. (1999) *Clin J Sport Med* 9(3): 157-60; Houshian et al. (1998) *Injury* 29(9): 651-4), are extremely common, and can occur in various anatomical regions (Best & Garrett Jr (1993) *Orthopaedic Sports Medicine* pp. 1-45): rupture or inflammation may occur at the supraspinatus and subscapularis tendon of the shoulder region, and in the biceps and triceps tendons of the upper limb; extensive tendon and ligament injuries can occur in both hands and fingers, disturbing the normal function of the appendage and making delicate movements impossible; knee injuries often involve the medial collateral ligament (MCL), anterior cruciate ligament (ACL) or posterior cruciate ligament (PCL), and can also involve the patellar tendon. Tendons are usually injured upon excessive acceleration or deceleration, especially when the associated muscles become fatigued. The injury often occurs as a laceration or an avulsion from the bone and tendon transaction, which is deemed rupture of the tendon. Such injuries are very common in individuals who frequently engage in strenuous activities for extended periods of time.

Although many nonsurgical treatment regimens such as bracing, rehabilitation program, immobilization, passive controlled movement and ultrasound have been used, surgical repair and reconstruction of a completely torn tendon or ligament is still the preferred treatment, in particular among young patients and those who require an early return to normal activities (Leppilahti & Orava (1998) *Sports Med* 25(2): 79-100), such as athletes and military personnel. Typical treatments include surgical repair using the Kessler suture procedure and the pedicle flap turn-down procedure (Shereff (1993) *Atlas of foot and ankle surgery* pp. 304-11) in achilles tendon, surgical reconstruction of torn anterior cruciate ligament (ACL) using autogenous patellar tendon graft (Shino et al. (1993) *Am J Sports Med* 21(4): 609-616) and reconstruction of ruptured posterior cruciate ligament (PCL) (Bosch et al. (1994) *Acta Orthop Belg* 60(suppl): 57-61).

Despite its popularity, the current surgical management of musculoskeletal tissues is not problem-free. The major complaint involving surgical treatment is the high rate of complications (Leppilahti & Orava (1998) *Sports Med* 25(2): 79-100). Most of these procedures involve multiple sutures and staples, which may be associated with wound complications such as infection and necrosis (Shereff (1993) *Atlas of foot and ankle surgery* pp. 304-11; Koh & Lim (1999) *Hand Surg* 4(2): 197-202). For procedures making use of autogenous tendon or facia grafts for reinforcement or reconstruction, additional soft tissue injuries at the donor sites are created which make the procedure more invasive and may lead to donor site morbidity. Recurrent rupture, skin adhesions and excessive scarring are other surgery-associated problems.

These complications have prompted investigation into laser tissue welding as an alternative or supplement to surgical options. Laser tissue welding is a developing technique with numerous clinical applications for many surgical specialties including orthopedics (Bass & Treat (1995) *Lasers Surg Med* 17: 315-49), of which repair of tendons is a potential use. An immediate regaining of partial strength after repair is essential because of the large stress the tendon is subjected to post-operatively. A previous report (Kilkelly & Choma (1996) *Laser Surg Med* 19: 487-91) using $CO_2$ and Argon lasers, showed that thermal welding of ruptured achilles tendon in rats led to ~50-70% tensile strength recovery at 2 weeks post-op but no immediate tensile strength improvement. Other modes of laser tissue interaction mechanisms such as low energy laser photostimulation have also been studied to improve tendon repair by stimulating the intrinsic tendon healing. These means were found to induce a significant (~30%) increase in collagen production but insignificant increase (~10%) in mature crosslinks in ruptured rabbit achilles tendon (Reddy et al. (1998) *Laser Surg Med* 22: 281-7). In addition, the mechanical properties of the repaired tendon, in particular stress and stiffness demonstrated a ~30% but statistically insignificant increase (Reddy et al. (1998) *Med Sci Sports Exerc* 30(6): 794-800).

The ideal technique for tissue adhesion would be simpler, more rapid, and prone to fewer post-operative complications than conventional techniques. In the cornea, an ideal tissue repair or wound closure technique would produce a water-tight seal without inducing astigmatism. In tissue grafts and/or tissue substitutes, such as collagen-based scaffolds, the ideal technique would enhance fixation to the surrounding host tissues. In particular, skin grafting techniques enabling rapid and sustained adherence to the wound surface and the ability to resist shear stress are ideal for successful graft take. Repair of injuries to tendons and ligaments would ideally minimize or eliminate the use of multiple sutures and autogenous tendon grafts, minimize complications associated with foreign-body reactions, and minimize the thermal damage to surrounding tissue currently associated with thermal laser tissue welding.

Initial repair technique plays an important role in determining overall outcome in peripheral nerve regeneration after injury (de Medinaceli et al. (1982), *Exp Neurol* 77(3): 634-43). Microsurgical re-approximation of severed nerve ends is currently the most commonly used technique for repair of peripheral nerve injuries in which a significant deficit of neural tissue does not occur. Unfortunately, even in more favorable lesions, such as median or ulnar nerve injuries in the forearm, only 10% of patients who undergo microsurgical repair achieve an excellent recovery, i.e. full muscle strength and normal two-point discrimination. There are both biologic and technical reasons for this. Following peripheral nerve injury, a large proportion of the lower motor neurons and sensory neurons from the injured nerve undergo apoptotic death, with loss of up to 30% of the neurons within the nerve. This biologic limitation virtually ensures inadequate or absent recovery distally for any proximal nerve injury. Although current microsurgical techniques utilizing end-to-end repair and nerve grafting are adequate for more distal injuries, those with longer nerve gaps and injuries that are more proximal rarely achieve complete recovery. Further complicating this issue, surgery itself is traumatic to the nervous tissue with suture material acting as a potential nidus for the formation of scar tissue, which inhibits regeneration of proximal nerve fibers (Korff et al (1992), *Otolaryngol-Head and Neck Surg* 106(4): 345-350).

In addition to standard surgical techniques, laser-based techniques have also been used in nerve repair. However, these methods typically result in heat absorption, which denatures proteins. Thus, there exists in the art a need for improved methods of nerve repair. Improved methods of regenerating nerve fibers, ideally without the formation of scar tissue, would be highly desirable for the treatment of many nerve injuries.

SUMMARY

The present invention is based, in part, on the discovery that the application of a photosensitizer (e.g., Rose Bengal (RB), riboflavin-5-phosphate (R-5-P), methylene blue (MB), or N-hydroxypyridine-2-(1H)-thione (N-HTP)) to a tissue, followed by photoactivation produces an adhesive tissue-tissue seal (e.g., to repair a wound, or seal a tissue transplant) without collagen denaturation or heat induced peripheral tissue damage. Furthermore, the tissue-tissue seal can be produced when the photosensitizer is applied to the tissue in the absence of an exogenously supplied source of cross-linkable substrate, e.g., a protein such as fibrin or fibrinogen or other protein-based tissue adhesive or glue. Such exogenous substances are often suggested to be used to contribute cross-linkable protein to a tissue. (Herein, a graft tissue or the components thereof is not considered such a source of exogenously supplied cross-linkable substrate.) This procedure is referred to herein as photochemical tissue bonding (PTB). PTB can be used ex vivo or in vivo in a subject, e.g., a human, or a non-human animal.

Accordingly, in one aspect, the invention features a method for cross-linking tissue, e.g., creating a tissue seal, such as in tissue grafting. The method includes identifying a tissue in need of repair, e.g., a collagenous tissue, cornea, skin, cartilage, ligament or tendon; contacting the tissue with a photosensitizer e.g., Rose Bengal (RB), riboflavin-5-phosphate (R-5-P), methylene blue (MB), or N-hydroxypyridine-2-(1H)-thione (N-HTP), and optionally contacting a second tissue, e.g. a tissue graft or substitute comprising natural or synthetic extracellular matrix-based scaffolds, such as collagen and proteoglycan, and/or other engineered tissue implants, with photosensitizer, to form a photosensitizer-tissue complex; and applying electromagnetic energy, e.g., light, to the tissue-photosensitizer complex sufficient to produce cross linking in the tissue or tissue graft. The tissue is not contacted with an exogenously supplied source of cross-linkable substrate, e.g., protein, e.g., fibrin or fibrinogen, or protein-based adhesive or glue, which is cross linked by the application of electromagnetic energy. (Herein, a graft tissue or the components thereof is not considered such a source of exogenously supplied cross-linkable substrate or adhesive.) PTB can be used to graft tissue ex vivo or in vivo in a subject, e.g., a human, or a non-human animal.

In one aspect, the tissue is in need of repair. This tissue can be of any type where adhesion or wound closure is necessary, for example a cardiovascular, neurological, gastrointestinal, urological, vascular, renal, ocular, oral, connective, respiratory, otolaryngological, dermatological, genital, gynecological or musculoskeletal tissue. Wound closure can comprise the joining of cut or otherwise separated edges or surfaces of the tissue/damaged tissue.

In one aspect, the tissue is corneal tissue. For example, the tissue, e.g., cornea, has been subjected to trauma, a surgical incision, LASIK flap reattachment, corneal transplant, or correction of astigmatism. One or more elements, for instance, cut or otherwise separated edges or surfaces, of the subject's corneal tissue can be joined together, or to graft tissue through photochemical tissue bonding.

In one embodiment, the tissue in need of repair is grafted with an exogenous tissue. An exogenous tissue is one supplied from a site other than the site of the lesion/wound. Preferably, this tissue is skin. The exogenous tissue can be in the form of a tissue graft, e.g. a graft or substitute comprising natural or synthetic extracellular matrix-based scaffolds, such as collagen and proteoglycan, and/or other engineered tissue implants. Suitable exogenous tissue can be supplied to a variety of sites, for example, to a wound, tear or lesion in a cardiovascular, neurological, gastrointestinal, urological, vascular, renal, ocular, oral, connective, respiratory, otolaryngological, dermatological, genital, gynecological or musculoskeletal tissue.

In yet another embodiment, the photosensitizer agent is selected from the group consisting of Rose Bengal, riboflavin-5-phosphate, methylene blue, and N-hydroxypyridine-2-(1H)-thione.

In yet another embodiment, the photosensitizer agent is Rose Bengal.

In yet another embodiment, the contacting step occurs ex vivo.

In yet another embodiment, the contacting step occurs in vivo in a subject, e.g., a human, or an non-human animal, preferably a non-albino animal, e.g., a non-albino rabbit.

In yet another embodiment, the subject is other than an albino animal, e.g., other than an albino rabbit.

In yet another embodiment, the subject is a human.

In yet another embodiment, the application of electromagnetic energy to the tissue-photosensitizer complex occurs without substantial thermal tissue damage, e.g., shrinkage or deformation around the wound site and thermal cell damage.

In yet another embodiment, the application of electromagnetic energy to the tissue-photosensitizer complex occurs without more than a 15° C. rise in temperature as measured, e.g., with an imaging thermal camera during irradiation.

In yet another embodiment, the application of electromagnetic energy to the tissue-photosensitizer complex occurs without more than a 10° C. rise in temperature as measured, e.g., with an imaging thermal camera during irradiation.

In yet another embodiment, the application of electromagnetic energy to the tissue-photosensitizer complex occurs without more than a 3° C. rise in temperature as measured, e.g., with an imaging thermal camera during irradiation.

In yet another embodiment, the application of electromagnetic energy to the tissue-photosensitizer complex occurs without more than a 2° C. rise in temperature as measured, e.g., with an imaging thermal camera during irradiation.

In yet another embodiment, the application of electromagnetic energy to the tissue-photosensitizer complex occurs without more than a 1° C. rise in temperature as measured, e.g., during irradiation with an imaging thermal camera.

In yet another aspect, the invention features, a method for repairing a corneal lesion, e.g., a corneal incision, laceration, or a corneal transplant, in a subject, e.g., a human, or a non-human animal, preferably a non-albino animal. The method includes: contacting a corneal tissue with at least one photosensitizer agent, e.g., RB, R-5-P, MB, or N-HTP, and applying electromagnetic energy, e.g., light, to the corneal tissue-photosensitizer complex sufficient to produce a reactive species, e.g., a reactive oxygen species, from the photosensitizer. The corneal tissue is not contacted with an exogenously supplied source of cross-linkable substrate, e.g., protein, e.g., fibrin or fibrinogen, or protein-based tissue adhesive or glue, which is cross-linked by the application of electromagnetic energy.

In one embodiment, the corneal lesion is caused by a surgical procedure.

In yet another embodiment, the surgical procedure is selected from the group consisting of corneal transplant surgery, cataract surgery, laser surgery, keratoplasty, penetrating keratoplasty, posterior lamellar keratoplasty, LASIK, refractive surgery, cornea reshaping, and treatment of corneal laceration.

In yet another embodiment one or more elements, e.g., cut or otherwise separated edges or surfaces, of the subject's corneal tissue can be joined together, or to graft tissue.

In yet another embodiment, a subject's muscle tendon can be joined to the subject's eye. E.g., an ocular misalignment can be reduced, adjusted, or corrected, for instance, by joining an eye muscle tendon to the eye.

In yet another embodiment, the cornea is in need of correction for astigmatism. For example, PTB can be used to correct, reduce, or decrease astigmatism, e.g., by inducing astigmatism in the orthogonal meridian, thereby counteracting preexisting astigmatism. In a preferred embodiment, PTB induces a predictable degree of corrective astigmatism.

In yet another embodiment, the method further comprises administration of an adjunctive therapy, e.g., contact lens therapy, amniotic membrane therapy, LASIK therapy, or administration of antibiotics.

In yet another embodiment, the electromagnetic energy applied is greater than 1200 J/cm$^2$. In another preferred embodiment, the electromagnetic energy applied is between 200 and 1200 J/cm$^2$. In another preferred embodiment, the electromagnetic energy applied is between 200 and 800 J/cm$^2$. In yet another preferred embodiment, the electromagnetic energy applied is between 200 and 500 J/cm$^2$. In yet another preferred embodiment, the electromagnetic energy applied is between 300 and 600 J/cm$^2$. In another preferred embodiment, the electromagnetic energy applied is between 350 and 550 J/cm$^2$.

In yet another embodiment, the electromagnetic energy is applied at an irradiance less than 3.5 W/cm$^2$.

In yet another embodiment, the electromagnetic energy is applied at an irradiance less than 1.5 W/cm$^2$.

In yet another embodiment, the electromagnetic energy is applied at an irradiance of about 0.10 W/cm$^2$.

In yet another embodiment, the subject is other than an albino animal, e.g., other than an albino rabbit.

In yet another aspect, the invention features, a method for repairing a corneal lesion in vivo in a living subject, e.g., a human, or a non-human animal, preferably a non-albino animal. The method includes contacting a corneal tissue with Rose Bengal (RB) to form a corneal tissue-RB complex; and applying electromagnetic energy, e.g., light, to the corneal tissue-RB complex in a manner effective to elicit the production of a reactive species, e.g., a reactive oxygen species, from the RB. The corneal tissue is not contacted with an exogenously supplied source of cross-linkable substrate, e.g., protein, e.g., fibrin or fibrinogen, or protein-based tissue adhesive or glue, which is cross-linked by the application of electromagnetic energy.

In one embodiment, the subject is a human.

In yet another embodiment, the corneal lesion is caused by a surgical procedure.

In yet another embodiment, the surgical procedure is selected from the group consisting of corneal transplant surgery, cataract surgery, laser surgery, keratoplasty, penetrating keratoplasty, posterior lamellar keratoplasty, LASIK, refractive surgery, cornea reshaping, and treatment of corneal laceration.

In yet another embodiment one or more elements, e.g., cut or otherwise separated edges or surfaces, of the subject's corneal tissue can be joined together, or to graft tissue.

In yet another embodiment, a subject's muscle tendon can be joined to the subject's eye, e.g., an ocular misalignment can be reduced, adjusted, or corrected, e.g., by joining an eye muscle tendon to the eye.

In yet another embodiment, the cornea is in need of correction for astigmatism. For example, PTB can be used to correct, reduce, or decrease astigmatism, e.g., by inducing astigmatism in the orthogonal meridian, thereby counteracting preexisting astigmatism. In a preferred embodiment, PTB induces a predictable degree of corrective astigmatism.

In yet another embodiment, the method further comprises administration of an adjunctive therapy, e.g., contact lens therapy, amniotic membrane therapy, LASIK therapy, or administration of antibiotics.

In yet another embodiment, the subject is other than an albino animal, e.g., other than an albino rabbit.

In yet another aspect, the invention features a kit for repairing corneal lesions, which kit includes a photosensitizer agent, e.g., RB, R-5-P, MB, or N-HTP, instructions for photoactivation of the photosensitizer agent to repair the corneal lesion, accessory tools and instructions for effective tissue edge approximation. In a preferred embodiment the kit does not include a source of cross-linkable substrate, e.g., protein, e.g., fibrin or fibrinogen, or protein-based tissue adhesive or glue, for use with the photosensitizer.

In one embodiment, the photosensitizer agent is Rose Bengal.

In yet another aspect, the invention features a method for repairing a musculoskeletal tissue e.g., a tendon, ligament or cartilage, damaged by a laceration or rupture, in a subject, e.g., a human, or a non-human animal. The method includes: contacting musculoskeletal tissue with at least one photosensitizer agent, e.g., RB, R-5-P, MB, or N-HTP, and applying electromagnetic energy, e.g., light, to the tendon tissue-photosensitizer complex sufficient to produce a reactive species, e.g., a free radical, from the reaction between the photosensitizer and the tissue. The musculoskeletal tissue is not contacted with an exogenously supplied source of cross-linkable substrate, e.g., protein, e.g., fibrin or fibrinogen, or protein-based tissue adhesive or glue, which is cross-linked by the application of electromagnetic energy.

In one embodiment, the subject is a human.

In yet another embodiment, the musculoskeletal tissue is a tendon.

In yet another embodiment, the tendon is ruptured.

In yet another embodiment, the tendon is damaged by an avulsion from the bone and tendon transection.

In yet another embodiment, the ruptured ends of the tendon are joined together.

In yet another embodiment, there is a laceration of the tendon.

In yet another embodiment, the edges of the laceration of the tendon are joined together.

In yet another embodiment, the tendon is joined to a tendon graft.

In yet another embodiment, the musculoskeletal tissue is a ligament.

In yet another embodiment, the ligament is a small ligament.

In yet another embodiment, the ligament is the anterior cruciate ligament.

In yet another embodiment, the photosensitizer agent is Rose Bengal.

In yet another embodiment, the Rose Bengal is applied to the musculoskeletal tissue at a concentration of less than 1.0% weight per volume in phosphate buffered saline. In another preferred embodiment, the Rose Bengal is applied at a concentration of less than 0.5% weight per volume in phosphate buffered saline. In another preferred embodiment, the Rose Bengal is applied at a concentration between 0.1 and 0.5% weight per volume in phosphate buffered saline.

In yet another embodiment, the electromagnetic energy applied to the musculoskeletal tissue is greater than 750 J/cm$^2$. In another preferred embodiment, the electromagnetic energy applied is between 50 and 750 J/cm$^2$. In another preferred embodiment, the electromagnetic energy applied is between 250 and 750 J/cm². In yet another preferred embodiment, the electromagnetic energy applied is between 250 and 500 J/cm².

In yet another embodiment, the electromagnetic energy is applied at an irradiance less than 1.5 W/cm².

In yet another embodiment, the electromagnetic energy is applied at an irradiance less than 1.0 W/cm².

In yet another embodiment, the electromagnetic energy is applied at an irradiance of between 0.5 and 1.0 W/cm².

In yet another embodiment, immediately after joining, the photochemically joined tendon has an ultimate stress, which is greater than 10% of that of a healthy tendon. In a preferred embodiment, immediately after joining, the photochemically joined tendon has an ultimate stress, which is greater than 25% of that of a healthy tendon. In a preferred embodiment, immediately after joining, the photochemically joined tendon has an ultimate stress which is greater than 50% of that of a healthy tendon.

In yet another embodiment, immediately after joining, the photochemically joined tendon has a stiffness which is greater than 10% of that of a healthy tendon. In a preferred embodiment, immediately after joining, the photochemically joined tendon has a stiffness which is greater than 25% of that of a healthy tendon. In a preferred embodiment, immediately after joining, the photochemically joined tendon has a stiffness which is greater than 50% of that of a healthy tendon.

In another embodiment, the present invention provides methods for adhering neural tissue, comprising contacting a first neural tissue and second neural tissue, and at least one photosensitizer agent to form a tissue-photosensitizer complex; and applying electromagnetic energy to the tissue-photosensitizer complex in a manner effective to bond the tissues, thereby creating a tissue seal between neural tissues.

In another embodiment, the present invention provides a method for adhering neural tissue, comprising placing a first neural tissue and second neural tissue in a conduit; contacting the first neural tissue and second neural tissue with at least one photosensitizer agent to form a tissue-photosensitizer complex; and applying electromagnetic energy to the tissue-photosensitizer complex in a manner effective to bond the tissues, thereby creating a tissue seal between the neural tissues and the conduit.

In another embodiment, the present invention provides a method for adhering neural tissue, comprising retracting the epineural tissue of a first neural segment and exposing the endoneurium; removing the exposed endoneurium; contacting the first and a second neural segment with at least one photosensitizer agent to form a tissue-photosensitizer complex; joining the second neural segment with the first neural segment and applying at least one suture between the segments; and applying electromagnetic energy to the tissue-photosensitizer complex in a manner effective to bond the tissues, thereby creating a tissue seal between the neural segments. Preferably, the first neural segment is distal and the second neural segment is proximal to the spinal column.

In another embodiment, the present invention provides a method for adhering blood vessel tissue, comprising placing a first blood vessel tissue and second blood vessel tissue in a conduit; contacting the first blood vessel tissue and second blood vessel tissue with at least one photosensitizer agent to form a tissue-photosensitizer complex; and applying electromagnetic energy to the tissue-photosensitizer complex in a manner effective to bond the tissues, thereby creating a tissue seal between the blood vessel tissues and the conduit.

In another embodiment, the present invention provides a method for adhering blood vessel tissue, comprising retracting a tissue layer of a distal vessel segment; contacting the distal and a proximal vessel segment with at least one photosensitizer agent to form a tissue-photosensitizer complex; joining the proximal vessel segment with the distal vessel segment and applying at least one suture between the segments; and applying electromagnetic energy to the tissue-photosensitizer complex in a manner effective to bond the tissues, thereby creating a tissue seal between the neural segments.

Other features, objects, and advantages of the invention will be apparent from the description and drawings, and from the claims, and are part of the invention.

DESCRIPTION OF THE DRAWINGS

The patent or application file contains at least one drawing executed in color. Copies of this patent or application with color drawing(s) will be provided by the Patent and Trademark Office upon request and payment of the necessary fee.

(FIG. 12A) and 1.68 W/cm² (FIG. 12B). The horizontal bar represents a distance of 0.1 inch (2.54 mm). The maximum temperature is represented by a color scale at the left-hand side of the thermograph.

DETAILED DESCRIPTION

Figure 1:
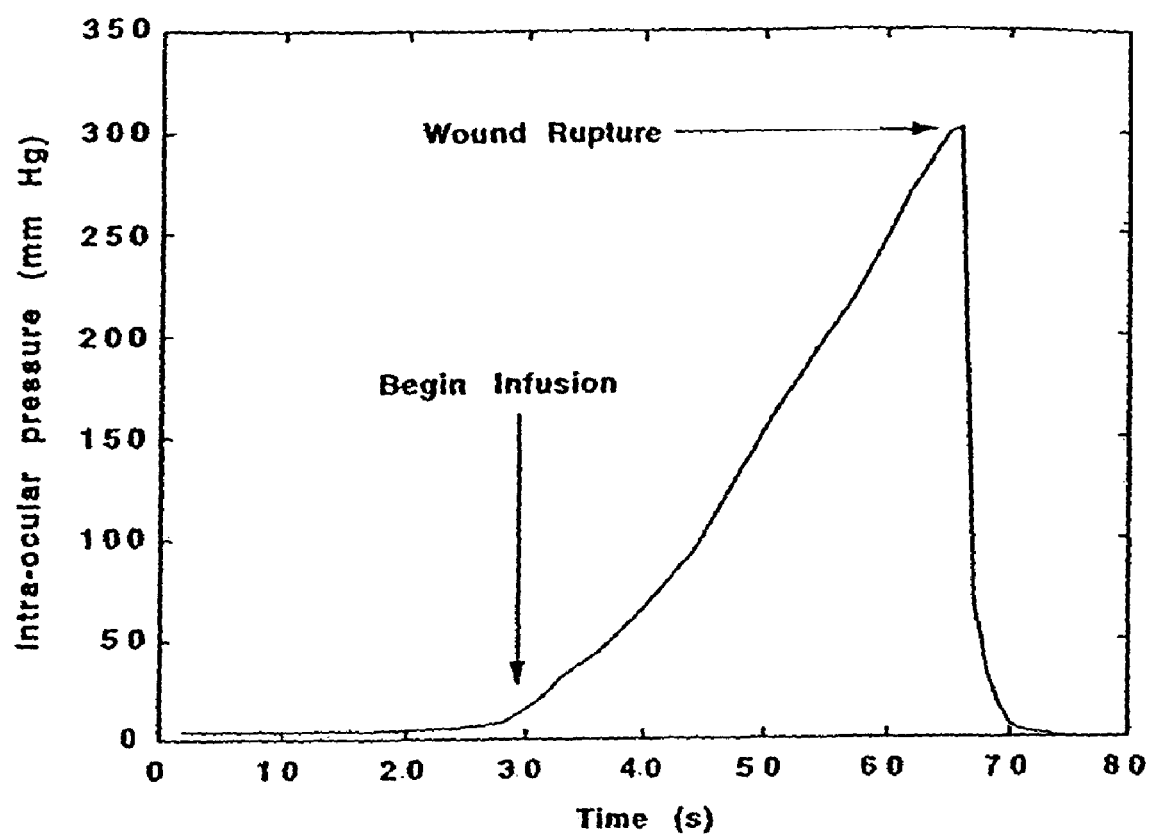
FIG. 1 shows a graph of a typical trace of increasing IOP with infusion time for a PTB treated eye, showing IOPL at 300 mm Hg.

Photochemical tissue bonding (PTB), as described herein, provides a method to create a tissue-tissue seal, e.g., to treat a wound, e.g., a corneal wound, without collagen denaturation or heat-induced peripheral tissue damage. PTB, as described herein, involves the application of a photosensitizer to a wound surface followed by photoactivation by laser irradiation to seal the wound. The photosensitizer can be effectively applied to seal a wound, or otherwise repair a tissue, such as by graft, in the absence of an exogenous protein-based adhesive, such as fibrinogen.

Photochemical tissue bonding has the advantage of producing covalent crosslinks that are theoretically stronger than the non-covalent interactions created by the thermal welding technique, such as those disclosed in U.S. Pat. Nos. 5,292,362 and 5,209,776. Photochemical tissue bonding provides for an immediate return of strength to the injured area in a manner that has considerably less associated tissue damage (Bass & Treat (1995) *Lasers Surg Med* 17: 315-49; Judy et al. (1993) *SPIE Proc* 1882: 221-4).

Methods of the invention provide strong covalent bonding at the tissue to tissue interface and have no requirement for an exogenous protein (other than what may be present in a tissue graft), e.g., fibrinogen, that must be isolated from the patient to be treated or derived from one or more donors. Methods of the invention do not require the use of chemical glues, e.g., cyanoacrylate adhesives. The methods described herein minimize tissue thermal denaturation of proteins caused by tissue heating.

Current methods of tissue grafting are complicated by multiple use of sutures, low cosmetic value, wound complications such as foreign body reactions, void and non-adherent grafts. The present invention overcomes problems known in the art. The methods of tissue adhesion described herein are ideal for tissues in need of repair and/or a water-tight seal. These tissues can be of any type where tissue adhesion such as wound closure is necessary, for example a cardiovascular, neurological, gastrointestinal, urological, renal, occular, oral, connective, respiratory, otolaryngological, dermatological, genital, gynecological or musculoskeletal tissue. Wound closure can comprise the joining of cut or otherwise separated edges or surfaces of the damaged tissue. Wound closure can further comprise the grafting of an exogenous tissue on to the surface of a damaged tissue. Preferably, this tissue is skin.

Closure of corneal wounds or corneal transplants with sutures can be associated with neo-vascularisation, rejection of the donor cornea, and induced post-operative astigmatism partly due to uneven suture tension. This can occur after penetrating keratoplasty where numerous sutures are needed to hold the graft in place. Suturing techniques designed to evenly distribute tension across corneal grafts may still result in significant astigmatism. Additionally, loose or broken sutures can leave a patient vulnerable to microbial keratitis. The sutures used are skill intensive and are mainly performed by corneal specialists. The methods described herein minimize the use of sutures. Although factors such as wound healing, host graft sizing and trephination techniques also play a role in post-operative astigmatism, the methods described herein hold the graft with equally distributed force and help reduce post-operative astigmatism. PTB reduces the operating and rehabilitation time for procedures to close wounds, e.g., to treat incisions or corneal lacerations, spot seal LASIK flaps, perform cataract surgery, and attach donor cornea.

Surgical repair of musculoskeletal tissue, such as ruptured tendons and ligaments, is currently plagued by complications resulting from the use of multiple sutures and staples. The use of these can lead to infection and necrosis, thereby negating the potential benefits of the reparative surgery. Other complications include recurrent rupture, skin adhesions and excessive scarring. In addition, it is preferable that patients who undergo surgery experience and immediate partial regaining of strength after the repair, due the large stress placed on during the period of recovery following surgery. The methods described in do not require the use of sutures or staples, thereby eliminating the possibility of foreign body reactions to them. In addition, the methods described herein result in an immediate increase in the mechanical properties of the tendon following the procedure, reducing the possibility of complications including recurrent rupture, and enhancing the subsequent healing process in tendons.

Photoactivation and Photosensitizers

The methods to create a tissue-tissue seal described herein include treating a tissue with a photosensitizer agent, e.g., RB, R-5-P, MB, or N-HTP, preferably in the absence of an exogenous protein, e.g., a protein based adhesive, e.g., fibrin or fibrinogen, and photoactivating the photosensitizer agent with electromagnetic radiation, e.g., light.

Photoactivation is used to describe the process by which energy in the form of electromagnetic radiation is absorbed by a compound, e.g., a photosensitizer, thus "exciting" the compound, which then becomes capable of converting the energy to another form of energy, preferably chemical energy. The electromagnetic radiation can include energy, e.g., light, having a wavelength in the visible range or portion of the electromagnetic spectrum, or the ultra violet and infra red regions of the spectrum. The chemical energy can be in the form of reactive species, e.g., a singlet oxygen, superoxide anion, hydroxyl radical, the excited state of the photosensitizer, photosensitizer free radical or substrate free radical species. The photoactivation process described herein preferably involves insubstantial transfer of the absorbed energy into heat energy. Preferably, photoactivation occurs with a rise in temperature of less than 15 degrees Celsius (C.), more preferably a rise of less than 10 degrees C., more preferably a rise of less than 3 degrees C., more preferably a rise of less than 2 degrees C. and even more preferably, a rise in temperature of less than 1 degree C. as measured, e.g., by an imaging thermal camera that looks at the tissue during irradiation. The camera can be focused in the area of original dye deposit, e.g., the wound area, or on an area immediately adjacent the wound area, to which dye will diffuse. As used herein, a "photosensitizer" is a chemical compound that produces a biological effect upon photoactivation or a biological precursor of a compound that produces a biological effect upon photoactivation. Preferred photosensitizers are those that absorb electromagnetic energy, such as light. While not wishing to be bound by theory, the photosensitizer may act by producing an excited photosensitizer or derived species that interacts with tissue, e.g., collagenous tissue, to form a bond, e.g., a covalent bond or crosslink. Photosensitizers typically have chemical structures that include multiple conjugated rings that allow for light absorption and photoactivation. Examples of photosensitive compounds include various light-sensitive dyes and biological molecules such as, for example, Photofrin®, synthetic diporphyrins and dichlorins, phthalocyanines with or without metal substituents, chloro-aluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorin e6, mono-1-aspartyl derivative of chlorin e6, di-1-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, amino anthraquinone, phenoxazine dyes, thiazines, methylene blue, phenothiazine and phenothiazine derivatives, pyridine, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-amino levulinic acid, benzonaphthoporphyrazines, cationic imminium salts, tetracyclines, lutetium texaphyrin, texaphyrin, tin-etio-purpurin, porphycenes, benzophenothiazinium, xanthenes, rose bengal, eosin, erythrosin, cyanines, merocyanine 540, selenium substituted cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

Preferred photosensitizers for use in the methods described herein are compounds capable of causing a photochemical reaction capable of producing a reactive intermediate when exposed to light, and which do not release a substantial amount of heat energy. Preferred photosensitizers are also water soluble. Preferred photosensitizers include Rose Bengal (RB); riboflavin-S-phosphate (R-5-P); methylene blue (MB); and N-hydroxypyridine-2-(1H)-thione (N-HTP).

Without wanting to be bound by theory, it is believed that the chemical energy, e.g., a reactive oxygen species, produced by photoactivation of the photosensitizer agent with which the tissue to be repaired is contacted, binds and causes structural changes in the amino acids of the proteins of the tissue, resulting in the formation of covalent bonds, polymerization, or cross-links between amino acids of the tissue, thus creating a proteinaceous framework that serves to seal, repair, heal, or close the tissue lesion or wound. For example, as a result of PTB treatment, strong covalent cross-links are believed to form between collagen molecules on opposing surfaces of a corneal lesion to produce a tight tissue seal.

The photosensitizer agent, e.g., RB, R-5-P, MB, or N-HTP, can be dissolved in a biocompatible buffer or solution, e.g., saline solution, and used at a concentration of from about 0.1 mM to 10 mM, preferably from about 0.5 mM to 5 mM, more preferably from about 1 mM to 3 mM.

The photosensitizer agent can be administered to the tissue by, e.g., injection into the tissue, or application onto the surface of the tissue. An amount of photosensitizer sufficient to stain, e.g., to cover the walls of, the lesion or wound to be repaired, can be applied. For example, at least 10 µl of photosensitizer solution, preferably 50 µl (microliter), 100 µl, 250 µl, 500 µl, or 1 ml, or more, of photosensitizer solution can be applied to a tissue, e.g., a cornea. Preferably, the photosensitizer has a binding efficiency, e.g., a collagen binding efficiency, such that the dye is predominantly bound to the surface of the incision.

The electromagnetic radiation, e.g., light, is applied to the tissue at an appropriate wavelength, energy, and duration, to cause the photosensitizer to undergo a reaction to affect the structure of the amino acids in the tissue, e.g., to cross-link a tissue protein, thereby creating a tissue seal. The wavelength of light can be chosen so that it corresponds to or encompasses the absorption of the photosensitizer, and reaches the area of the tissue that has been contacted with the photosensitizer, e.g., penetrates into the region where the photosensitizer presents. Preferably, the electromagnetic energy applied is less than 2000 $J/cm^2$. Even more preferably, the electromagnetic energy applied is between 100 and 500 $J/cm^2$. The electromagnetic radiation, e.g., light, necessary to achieve photoactivation of the photosensitizer agent can have a wavelength from about 350 nm to about 800 nm, preferably from about 400 to 700 nm and can be within the visible, infrared or near ultraviolet spectra. The energy can be delivered at an irradiance of about between 0.1 and 5 $W/cm^2$, preferably between about 0.5 and 2 $W/cm^2$. The duration of irradiation can be sufficient to allow cross-linking of one or more proteins of the tissue, e.g., of a tissue collagen. For example, in corneal tissue, the duration of irradiation can be from about 30 seconds to 30 minutes, preferably from about 1 to 5 minutes. The duration of irradiation to deliver the required dose to a skin or tendon wound can be from about one minute to 60 minutes, preferably between 1 and 15 minutes. The duration of irradiation can be substantially longer where power is lower.

Suitable sources of electromagnetic energy include commercially available lasers, lamps, light emitting diodes, or other sources of electromagnetic radiation. Light radiation can be supplied in the form of a monochromatic laser beam, e.g., an argon laser beam or diode-pumped solid state laser beam. Light can also be supplied to a non-external surface tissue through an optical fiber device, e.g., the light can be delivered by optical fibers threaded through a small gauge hypodermic needle or an arthroscope. Light can also be transmitted by percutaneous instrumentation using optical fibers or cannulated waveguides.

The choice of energy source will generally be made in conjunction with the choice of photosensitizer employed in the method. For example, an argon laser is a preferred energy source suitable for use with RB or R-5-P because these dyes are optimally excited at wavelengths corresponding to the wavelength of the radiation emitted by the argon laser. Other suitable combinations of lasers and photosensitizers will be known to those of skill in the art. Tunable dye lasers can also be used with the methods described herein.

Uses

The methods described herein are suitable for use in a variety of applications, including in vitro laboratory applications, ex vivo tissue treatments, but especially in in vivo surgical procedures on living subjects, e.g., humans, and non-surgical wound healing.

The methods described herein are particularly useful for surgical applications, e.g., to seal, close, or otherwise join, two or more portions of tissue, e.g., to perform a tissue transplant and/or grafting operation, or to heal damaged tissue, e.g., a corneal incision, or to prevent leakage from tissue. The methods described herein can be used in surgical applications where precise adhesion is necessary, and/or where the application of sutures, staples, or protein sealants is inconvenient or undesirable. For example, in corneal transplants and other eye operations, surgical complications such as inflammation, irritation, infection, wound gap, leakage, and epithelial ingrowth, often arise from the use of sutures. The photochemical tissue bonding methods described herein are particularly suitable for use in surgery or microsurgery, for example, in surgical operations or maneuvers of the eye, e.g., in the repair of corneal wounds or incisions, in refractive surgery (the correction of irregularities or defects in the cornea by "shaving" an even layer off the cornea), in keratoplasty, in corneal transplants, and in correction of astigmatism, e.g., by inducing astigmatism designed to counteract preexisting astigmatism, e.g., in the orthogonal meridian.

As another example, sutures cannot be satisfactorily used on bone joint cartilage because of their mechanical interference with the mutual sliding of cartilage surfaces required for joint motion. Neither can sutures be used to seal surfaces of small blood vessels with diameters 1-2 mm or less, as sutures impinge upon the vessel lumen, compromising blood flow. Further, in skin grafting, sutures can induce foreign body responses that lead to scarring and therefore reduce cosmetic value. Thus, the methods described herein are also useful in surgical interventions of vascular tissue, joint cartilage, skin, gastrointestinal tract, nerve sheaths, urological tissue, small ducts (urethra, ureter, bile ducts, thoracic duct), oral tissue or even tissues of the middle or inner ear. Other procedures where sutures or staples are not indicated or desirable, and where the photochemical tissue bonding methods described herein are useful, include procedures involving laparoscopic operations or interventions such as laparoscopic (LP) thoracic procedures, LP appendectomy, LP hernia repairs, LP tubal ligations and LP orbital surgeries.

Photochemical tissue bonding methods as described herein are optimal for the repair of musculoskeletal tissues such as tendons, ligaments, extracellular matrix and cartilage. For example, these methods are particularly suitable for repair of lacerations or ruptures of tendons such that the healing of the tendon in the patient may benefit from an immediate recovery in the strength of the injured site following repair, and such that the recovery is not hindered by infection of foreign-body reactions that may occur following the use of multiple staples or sutures. In addition, use of these methods may reduce the surgery time, may help prevent a future recurrent rupture of the site, and may reduce hospitalization and immobilization time during the rehabilitation period. Photochemical tissue bonding methods as described herein are optimal for use in sports medicine.

The photochemical tissue bonding methods described herein can also be used in tissue grafting. Exogenous grafts can be, for example, autografts, allografts or xenografts. In one embodiment, an exogenous tissue graft comprising tissue such as skin, muscle, vasculature, stomach, esophagus, colon or intestine, can be placed over the surface of the wound, impregnated with the photosensitizer agent described herein, and photoactivated with a visible light source, e.g., an incandescent, fluorescent or mercury vapor light source, e.g., a xenon arc lamp, or a laser light source, e.g. argon-ion laser. Preferably, the photochemical bond enables rapid and sustained adherence of the graft to the wound surface and the ability to resist shear stress. Sources of grafted tissue can be any known in the art, including exogenous grafts obtained from non-injured tissues in a subject. Sources of grafted tissue can also comprise extracellular matrix-based scaffolds, such as collagen and proteoglycan, and/or other engineered tissue implants.

Exogenous grafts can likewise be synthetic, e.g. skin substitutes. Synthetic materials suitable for use in grafting include, but are not limited to, silicon, polyurethane, polyvinyl and nylon. Skin substitutes can be any known in the art, including those comprising culture derivatives and cellular or acellular collagen membranes. Culture derived substitutes give rise to bilayer human tissue, for example Apligraf™ comprises epidermal or dermal analogs derived from neonatal foreskin, the host-graft composite of which will become repopulated with cells from the host subject. Commercially available skin substitutes include Biobrane™, composed of silicon, nylon and collagen, TransCyte™, composed of silicon, collagen, fibronectin and glycosaminoglycan, and Integra™, composed of silicon, collagen and glycosaminoglycan. Skin substitutes can be used in applications of permanent and semi-permanent grafting. Preferably, Integra™ is used for permanent grafting.

In grafting tissues, the surface of the graft is aligned to the lesion site through a process known in the art as "approximation." Approximation of the graft to the lesion site can be carried out according to methods known in the art. For instance, a graft can be placed on top of the lesion site and aligned so that the dye-stained dermal sides are in close approximation. Molecular contact between the graft and the lesion site is achieved by close approximation, which can be performed through pressing and smoothing the dermal-to-dermal composite with several layers of tissue paper, which are then removed without disturbing the graft interface. The approximated graft-lesion site composite is then ready for irradiation.

The photochemical tissue bonding methods described herein can also be used to supplement the use of sutures, e.g., to reinforce sutured anastomosis. Sutures leave a tract behind which can allow for leakage of fluids and organisms. The problem of leakage is especially critical in vascular anastomoses or for any anastomoses of a fluid-containing structure (aorta, ureter, GI tract, eye, etc.) where the fluid or contents inside can leak out through the suture hole. In one embodiment, a wound can be sutured according to general procedures and then treated with the photochemical tissue bonding methods described herein, thereby making the healing wound water tight, and impermeable to bacteria.

In addition, the methods described herein can be used in non-surgical wound healing applications, e.g., a photochemical adhesive can be used for wound healing in addition to, or in place of, a conventional bandage, optionally in combination with another beneficial material for wound healing. In one embodiment, a biocompatible substrate, e.g., a conventional bandage material, e.g., a strip of fiber, can be impregnated with the photosensitizer agent described herein, applied to a wound, and photoactivated with a visible light source, e.g., an incandescent, fluorescent or mercury vapor light source, e.g., a xenon arc lamp, or a laser light source. The photosensitizer-impregnated bandage can contain another beneficial material for wound healing, e.g., an antibiotic. In some embodiments, the photosensitizer-impregnated bandage, and/or the light source, can be supplied to a subject in a kit, e.g., a kit for use by a health care practitioner, or a kit for household use, which kits can contain instructions for use. The photochemical adhesive described herein can be left on the wound, or can be replaced as necessary. Such an adhesive can be used ex vivo, on a tissue removed from the body, or in situ on a subject, e.g., a human subject. For example, a photochemical adhesive described herein can be used as an "artificial skin" or covering agent to cover large, oozing surfaces inside or outside the body.

The methods described herein can also be used to cross-link proteins for use in laboratory applications, e.g., to fix proteins for microscopy; to immobilize antibodies or other protein reagents to a substrate for diagnosis or purification; or to cross link proteins or peptides to a solid matrix for use in chromatographic or immunological applications.

In another embodiment, the present invention provides methods for adhering neural tissue, comprising contacting a first neural tissue and second neural tissue, and at least one photosensitizer agent to form a tissue-photosensitizer complex; and applying electromagnetic energy to the tissue-photosensitizer complex in a manner effective to bond the tissues, thereby creating a tissue seal between neural tissues.

The neural tissues can be any neural tissues in need of repair. For example, the first and second neural tissues can comprise two exposed nerve segments, or "stumps," at the proximal and distal sides a nerve lesion. The neural tissues can comprise, for example, epineurium, perineurium and dura. Preferably, the neural tissues comprise epineurium.

The nerve lesion can be one that completely severs or transects the nerve, or can be any other form of localized damage to a nerve. Methods of the present invention are especially suitable for shortened nerves (i.e., having severed and shortened axonal segments). For shortened nerves, adhering neural tissue comprising the epineurium allows the axonal segments to grow and rejoin within the shell of the bonded epineurium. In a preferred embodiment the neural tissue to be repaired comprises peripheral nerves, such for example, the sciatic nerve.

The two neural tissues are treated with a suitable photosensitizer agent. Any of the photosensitizer agents describe herein can be used. In a preferred embodiment, the photosensitizer agent is rose bengal. Either or both of the neural tissues can be treated with the photosensitizer agent.

In a preferred embodiment, treatment of the neural tissues with a photosensitizer agent is performed before the two neural tissues are brought into close physical contact with one another. In alternative embodiments, the photosensitizer agent is applied to the two neural tissues at the same time, or after the two neural tissues are brought into close physical contact with one another.

In one embodiment, any suitable source, wavelength, and energy of electromagnetic radiation can be used to illuminate the tissue:photosensitizer complex, provided that it is sufficient to activate the photosensitizer agent. Suitable illumination parameters for various photosensitizer agents are provided herein. Additionally, one of skill in the art could readily determine suitable illumination parameters without undue experimentation.

In embodiments where rose bengal is used as the photosensitizer agent, it is preferred that wavelengths in the range of 350-750 nm are used, preferably 532 nm is used.

In another embodiment, the present invention provides a method for adhering neural tissue, comprising placing a first neural tissue and second neural tissue in a conduit; contacting the first neural tissue and second neural tissue with at least one photosensitizer agent to form a tissue-photosensitizer complex; and applying electromagnetic energy to the tissue-photosensitizer complex in a manner effective to bond the tissues, thereby creating a tissue seal between the neural tissues and the conduit.

In another embodiment, the present invention provides a method for adhering blood vessel tissue, comprising placing a first blood vessel tissue and second blood vessel tissue in a conduit; contacting the first blood vessel tissue and second blood vessel tissue with at least one photosensitizer agent to form a tissue-photosensitizer complex; and applying electromagnetic energy to the tissue-photosensitizer complex in a manner effective to bond the tissues, thereby creating a tissue seal between the blood vessel tissues and the conduit.

A conduit of any suitable biocompatible material can be used, such as collagen. The conduit is formed from a tissue including, but not limited to, blood vessel, acellular muscle and nerve.

The conduit can be formed from a polymer selected from the group consisting of polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbomene, hydrogels, metallic alloys, and oligo(.epsilon.-caprolactone)diol as switching segment/oligo(p-dioxyanone)diol as physical crosslink. Other suitable polymers can be obtained by reference to The Polymer Handbook, 3rd edition (Wiley, N.Y., 1989). The conduit can also be formed from silicone.

Preferably, the conduit is a collagen conduit, and a circumferential, watertight seal is created. Where neural tissue is joined, it is preferable that the seal is effective to maintain the intraneural neurotrophic environment.

In another embodiment, the present invention provides a method for adhering neural tissue, comprising retracting the epineural tissue of a first neural segment and exposing the endoneurium; removing the exposed endoneurium; contacting the first and a second neural segment with at least one photosensitizer agent to form a tissue-photosensitizer complex; joining the second neural segment with the first neural segment and applying at least one suture between the segments; and applying electromagnetic energy to the tissue-photosensitizer complex in a manner effective to bond the tissues, thereby creating a tissue seal between the neural segments.

This method is referred to herein as the "cuff" method, due to the retracting of the outer layer into a "cuff." As used herein, the term "retracting" refers to the folding back of at least one tissue layer of a segment (i.e., nerve or vessel segment) such that the inner surface of the layer becomes exposed.

Preferably, the first neural segment can be contacted with at least one photosensitizer agent on the inner surface of the retracted epineurium, and the second neural segment can be contacted with at least one photosensitizer agent on the outer surface of the epineurium prior to joining.

The second neural segment can be joined to the first neural segment by placing the second neural segment within the epineurium of the first neural segment. Preferably, the first neural segment is distal and the second neural segment is proximal to the spinal column. When joined in this orientation, the nerve fibers are most effectively retained within the confines of the sealed neural tissue.

The "cuff" method can be used to adhere blood vessels (e.g., an artery or a vein) as well. Thus, in another embodiment, the present invention provides a method for adhering blood vessel tissue, comprising retracting a tissue layer of a distal vessel segment; contacting the distal and a proximal vessel segment with at least one photosensitizer agent to form a tissue-photosensitizer complex; joining the proximal vessel segment with the distal vessel segment and applying at least one suture between the segments; and applying electromagnetic energy to the tissue-photosensitizer complex in a manner effective to bond the tissues, thereby creating a tissue seal between the neural segments.

Proximal to distal is determined according to the direction of blood flow in the vessel. The proximal vessel segment is upstream and the distal vessel segment is downstream of the blood flow. Preferably, the proximal vessel segment is joined to the distal vessel segment by placing the proximal vessel segment within the distal vessel segment. Prior to joining, the distal vessel segment is contacted with at least one photosensitizer agent on an inner surface, and the proximal vessel segment is contacted with at least one photosensitizer agent on an outer surface. Irradiation can be provided externally, around the circumference of the vessel, or internally, by illuminating the inner channel of the vessel (e.g., illuminating the interior of the vessel such that the inner surface is bonded).

Kits

The invention also includes kits for use in photochemical tissue bonding. Such kits can be used for laboratory or for clinical applications. Such kits include a photosensitizer agent, e.g., a photosensitizer described herein, and instructions for applying and irradiating the photosensitizer to crosslink at least one protein reagent for laboratory use, or to bond, repair, or heal an animal tissue, e.g., a human tissue, particularly in a human patient. The kits can include a container for storage, e.g., a light-protected and/or refrigerated container for storage of the photosensitizer agent. A photosensitizer included in the kits can be provided in various forms, e.g., in powdered, lyophilized, crystal, or liquid form. Optionally, a kit can include an additional agent for use in a tissue bonding, wound repair, or ocular therapy application, e.g., an antibiotic or a contact lens.

The kits described herein can also include a means to apply the photosensitizer agent to a tissue, for example, a syringe or syringe-like device, a dropper, a powder, an aerosol container, sponge applicator, and/or a bandage material. Kits can further include accessory tools for tissue approximation e.g. clips, standard weights, aspiration apparatus, and compression gauges.

Kits can include instructions for use, e.g., instructions for use in the absence of an exogenously supplied source of cross-linkable substrate, e.g., protein, e.g., fibrin or fibrinogen.

EXAMPLES

Example 1

Assessment of PTB in Repair of Corneal Incisions

PTB can be used to seal or repair a tissue, e.g., a wound, e.g., a corneal wound. This example illustrates the experimental procedure designed to test the efficacy of PTB, as described herein, using mammalian corneas ex vivo. Experiments were performed according to the following procedure.

Rabbit eyes were received on ice (Pel-Freez Biologicals) approximately 17-24 hours after sacrifice and enucleation. The eyes were kept on ice and used the same day. The eye to be studied was mounted on a plastic-covered polystyrene block and fixed in position by needles inserted through the extraocular muscles into the polystyrene. The eye was then placed under a dissecting microscope (Reichert Scientific Instruments, Ill.) allowing visualization of the treated area during the entire procedure. A 27 G needle was inserted parallel to the iris, 2 mm anterior to the limbus into clear cornea, and positioned above the lens in the anterior chamber. The needle was connected to both a blood pressure transducer (Harvard Apparatus, Mass.) and a mini-infuser 400 (Bard Harvard) via a T coupler. The pressure transducer consists of a transducer element that is hard wired to an amplifier box and uses a semi-disposable dome with an integral silicone rubber membrane. Pressure inside the dome is transmitted through the membrane to a plastic button whose motion is translated to a voltage. The voltage generated by the transducer amplifier combination is proportional to the lower limit of intraocular pressure (IOP). Signals from the transducer amplifier were recorded using a Macintosh G3 Power book equipped with a PCMICA (DAQCARD—1200) data acquisition card (National Instruments, Tex.). Data acquisition was controlled using programs written using the LabView 4 software package (National Instruments, Tex.). The voltage from the transducer and amplifier was converted to pressure by calibrating with a standing manometer.

Experiments on individual eyes were initiated by increasing the IOP to 30-40 mm Hg, using water infusion at a rate of 1 mL per minute. An incision was made in the cornea, 1 mm from the limbus and parallel to the iris, using a 3.5 mm angled keratome (Becton Dickinson Co.). For each eye the IOP required to produce fluid leakage from the incision ($IOP_L$) was recorded pre- and post-PTB treatment. A photosensitizer, dissolved in phosphate buffer solution (PBS, pH 7.2, Gibco BRL) was applied to the walls of the incision using a Gastight, 50 µl syringe (Hamilton Co.) with a 27 G needle. Confocal fluorescence spectroscopy confirmed the location of photosensitizer, e.g., rose Bengal, on the incision walls and indicated that the photosensitizer penetrated only approximately 100 µM laterally into the wall of the incision.

The photosensitizers, their absorption maxima, and their absorption coefficients at the laser wavelength used in this Example were, e.g., rose bengal (RB), 550 nm, 33000 $dm^3 mol^{-1} cm^{-1}$ at 514 nm; fluorescein (Fl), 490 nm, 88300 $dm^3 mol^{-1} cm^{-1}$ at 488 nm; methylene blue (MB), 664 nm, 15600 $dm^3 mol^{-1} cm^{-1}$ at 661 nm; riboflavin-5-phosphate (R-5-P), 445 nm, 4330 $dm^3 mol^{-1} cm^{-1}$ at 488 nm; and N-hydroxypyridine-2-(1H)-thione (N-HPT), 314 nm, 2110 $dm^3 mol^{-1} cm^{-1}$ at 351 nm. The photosensitizers were used as received with the exception of N-HPT which was recrystallized twice from aqueous ethanol before use. The concentrations of the photosensitizers were adjusted so that all the solutions had an absorbance of approximately 1.0 in a path length of 200 µm at the laser irradiation wavelength (with the exception of N-HPT for which the absorption was approximately a factor of 10 lower).

Irradiations employed a continuous wave (CW) argon-ion laser (Innova 100; Coherent, Inc., Palo Alto, Calif.) at 488 nm (for Fl and R-5-P), 514.5 nm (for RB) or 351 nm (for NHPT). An argon-ion-pumped dye laser (CR-599; Coherent) with 4-dicyanomethylene-2-methyl-6-(p-dimethylaminostyryl)-4H-pyran dye (Exciton, Inc., Dayton, Ohio) was used for irradiation at 661 nm (for MB). Laser light was coupled into a 1 mm diameter quartz fiber and a 1 cm diameter spot on the tissue was created by using a combination of 1 and 2 inch focal length, S1-UV grade fused silica, biconvex lenses (Esco Products), mounted in a SM1 series cage assembly (Thorlabs, N.J.). The 1 cm diameter circular spot was sufficient to cover the entire incision and the optics were adjusted so that the laser light was incident on the cornea at an angle approximately 45° to the plane of the incision. Dose response curves were obtained by varying the duration of the irradiation at a constant irradiance. In separate experiments the effects of laser irradiance were investigated by comparison of the same delivered dose using different irradiances. The doses used ranged from 124 to 1524 $J/cm^2$ and the irradiances used were 0.64, 1.27, 2.55 and 3.86 $W/cm^2$. The laser exposure time varied from 33 seconds for the lowest dose using the highest irradiance to 26 minutes, 27 seconds for the highest dose using the lowest irradiance. The $IOP_L$ was recorded immediately following treatment. Infusion was started (1 mL per minute) and the IOP increased until a maximum followed by a sharp decrease occurred, corresponding to the opening of the incision and leakage of fluid from the anterior chamber. A typical trace showing the changes in IOP with infusion time is shown in FIG. 1. Five to 10 rabbit eyes were tested for each condition of dose and irradiance.

Control experiments included: (1) irradiation with no photosensitizer application, (2) photosensitizer application only and (3) no photosensitizer or laser irradiation. In the experiments using no photosensitizer, PBS was applied to the incision walls, using the same method as described for the photosensitizers. In control experiments with no laser irradiation the eye was allowed to stand for the same period of time as the laser-treated samples.

Example 2

Use of Rose Bengal (RB) in PTB

In the cornea, RB can be used in PTB at a concentration of about 0.5 mM to 5 mM, preferably about 1 mM to 3 mM. The wavelength of irradiation for RB is preferably about 450-600 nm, more preferably about 500 to 560 nm. The dose of irradiation can be from about 0.5 to 2 $kJ/cm^2$. The irradiance delivered can be from about 0.2 to 3 $W/cm^2$. The duration of irradiation is preferably from about 1 to 10 minutes.

Figure 2:
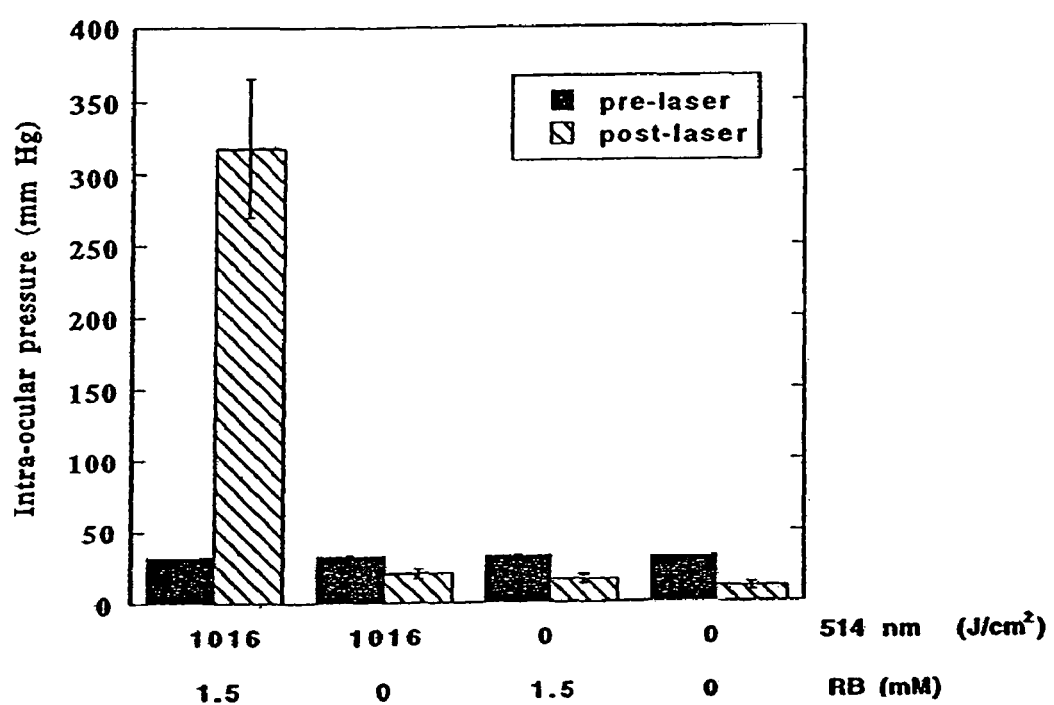
FIG. 2 shows a graph of the mean IOPL values for PTB treated eyes (n=5) using 514 nm light (2.55 W/cm²) and Rose Bengal (1.5 mM) in PBS. Additional controls are incisions treated with Rose Bengal or buffer but no laser light.

Treatment of incisions with 1.5 mM RB and 514 nm laser light resulted in an increase in post-treatment $IOP_L$, as measured as described in Example 1. Control experiments demonstrated that a significant increase ($p<0.005$) in the $IOP_L$, following PTB treatment, occurred when both RB and laser irradiation were applied and not by either alone (FIG. 2). The mean $IOP_L$ of incisions treated with RB and 514 nm laser light was greater than 300±48 mm Hg, whereas laser irradiation alone or photosensitizer alone produced no significant increase between the pre- and post-treatment $IOP_L$ values.

Figure 3:
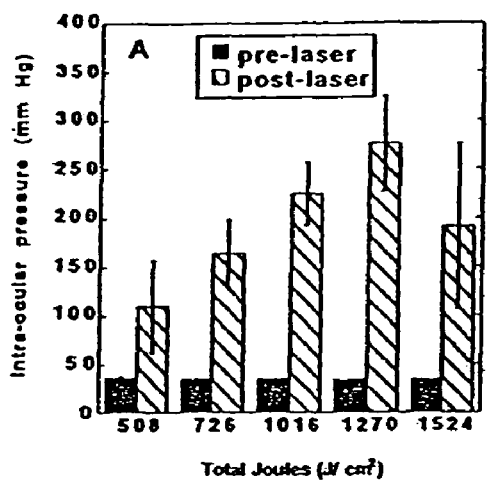
FIG. 3 shows graphs of mean IOPL before and after PTB using Rose Bengal and 514 nm irradiation. Rose Bengal (10 μl, 1.5 mM) was applied to the incision surfaces then treated with the doses indicated using irradiances of: (A) 1.27 W/cm2, (B) 2.55 W/cm2 and (C) 3.82 W/cm2.
Figure 3:
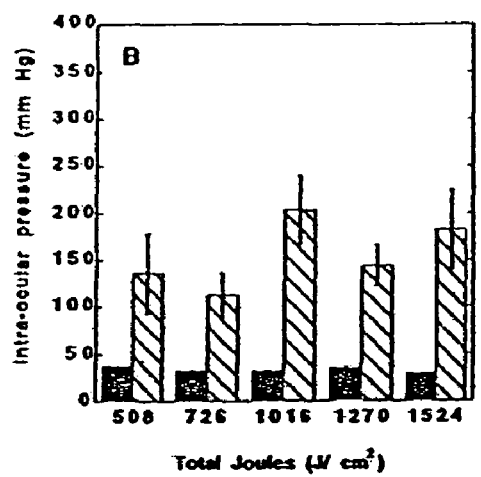
Figure 3:
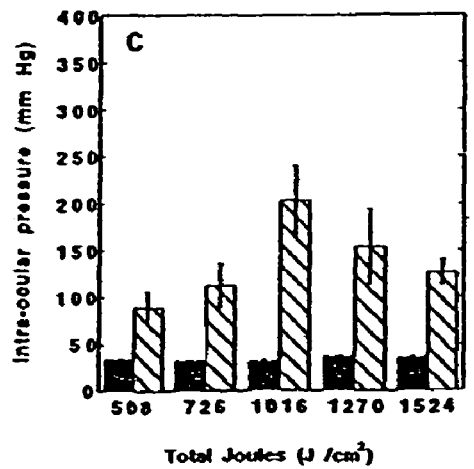

Dose response curves for $IOP_L$ are shown in FIG. 3 for RB doses delivered at irradiances of 1.27 (3A), 2.55 (3B) and 3.82 $W/cm^2$ (3C). A dose-response relationship was observed at the lowest irradiance (1.27 $W/cm^2$) for doses between 508 and 1270 $J/cm^2$ (3A). No significant rise in the $IOP_L$ was observed for doses below 508 $J/cm^2$ at any irradiance tested. PTB was most efficient at 1270 $J/cm^2$ delivered at an irradiance of 1.27 $W/cm^2$. All doses delivered at the two lower irradiances (1.27 and 2.55 $W/cm^2$) gave $IOP_L$ values greater than 100 mm Hg. Treatment using irradiances of 2.55 and 3.82 $W/cm^2$ produced no obvious dose response pattern. In general, for a selected dose the $IOP_L$ was lower at higher irradiances. For example, at 1270 $J/cm^2$ the mean $IOP_L$ values were 274, 150 and 130 mm Hg for the irradiances 1.27 $W/cm^2$, 2.55 $W/cm^2$ and 3.86 $W/cm^2$.

Post-treatment, the eyes were examined for the presence of thermal damage. Tissue shrinkage and deformation around the wound site were taken as signs of thermal damage. Thermal damage to the cornea was not observed at the lowest irradiance tested (1.27 W/cm2). Thermal damage could be observed at doses of 762 to 1524 J/cm2 at the highest irradiance (3.82 W/cm2) and occasionally at 2.55 W/cm2. Thermal effects produced using high irradiances may produce collagen contraction resulting in distortion of the patient's vision.

Example 3

Use of Riboflavin-5-Phosphate (R-5-P) in PTB

In the cornea, R-5-P can be applied for PTB at a concentration of about 1 mM to 30 mM, preferably about 10 mM to 20 mM. The wavelength of irradiation for R-5-P is preferably about 400-600 nm, more preferably about 450 to 550 nm. The dose of irradiation can be from about 0.5 to 2 kJ/cm$^2$. The irradiance delivered can be from about 0.2 to 3 W/cm$^2$. The duration of irradiation is preferably from about 1 to 10 minutes.

Figure 4:
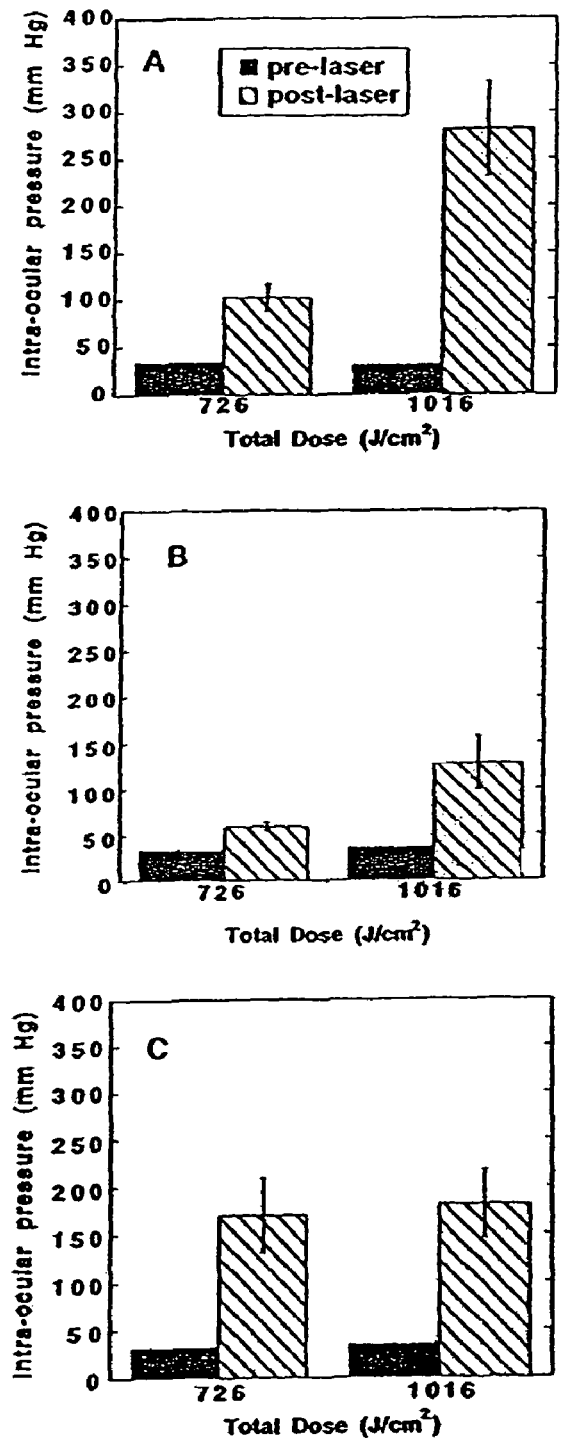
FIG. 4 shows graphs of mean IOPL before and after PTB using R-5-P and 488 nm irradiation. R-5-P (40 μl, 11 mM) was applied to the incision surfaces then treated with the doses indicated using irradiances of: (A) 1.27 W/cm2, (B) 2.55 W/cm2 and (C) 3.82 W/cm2.

The effect of R-5-P PTB was assessed as described in Example 1. The application of 11 mM R-5-P and irradiation using 488 nm light, at the same irradiances used for RB, and doses of 762 J/cm$^2$ and 1016 J/cm$^2$, significantly increased the post PTB treatment $IOP_L$ value (p<0.05), see FIG. 4. The $IOP_L$ values observed using R-5-P are of a similar magnitude to those for RB. However, the $IOP_L$ values observed for each dye at the same irradiance and dose were not comparable. Although the treatment produces significant increases in $IOP_L$, no simple pattern between the two dyes is observed.

Example 4

Use of N-hydroxypyridine-2-(1H)-thione (N-HTP) in PTB

In the cornea, N-HTP can be applied at a concentration of about 0.5 mM to 10 mM, preferably about 3 mM to 6 mM. The wavelength of irradiation for N-HTP is preferably about 330-400 nm. The dose of irradiation can be from about 0.5 to 2 kJ/cm$^2$. The irradiance delivered can be from about 0.2 to 3 W/cm$^2$. The duration of irradiation is preferably from about 1 to 10 minutes. A 4.5 mM solution of NHPT was applied to the walls of the incision, as described in Example 1, and irradiated using 351 nm light (0.64 W/cm2) at doses ranging from 127 J/cm2 to 508 J/cm2. Mean $IOP_L$ values of 60±23 mm Hg and 126±40 mm Hg were produced when using the doses of 254 J/cm2 and 508 J/cm2 respectively, lower doses than used for the other photosensitizers.

Example 5

Use of Methylene Blue (MB) in PTB

MB is a frequently used dye in ophthalmic surgery that has been reported to photosensitize collagen cross-links in rat tail tendon (Ramshaw et al. (1994) *Biochim Biophys Acta* 1206: 225-230). Our previous studies showed that MB and 355 nm light did not produce efficient cross-linking of soluble collagen. MB was therefore used as a control in these ex vivo studies. MB (3 mM) was applied to the walls of the incision, as described in Example 1, and irradiated with 0.64 W/cm$^2$ of 661 nm light. Doses of 508/cm$^2$, 762 J/cm$^2$ and 1016 J/cm$^2$ did not increase the post-treatment, $IOP_L$. However, it was observed that MB did not stain the corneal tissue efficiently, which perhaps explains its low efficiency for PTB.

Example 6

Assessment of Thermal Contribution to PTB

Laser activated tissue welding has been studied in a variety of tissues (Abergel et al. (1986) *J Am Acad Dermatol.* 14: 810-814; Cilesiz et al., supra; Massicotte et al. (1998) *Lasers in Surgery and Medicine* 23:18-24; Oz et al. (1990) *J Vasc Surg.* 11:718-725; Poppas et al. (1996) *Lasers in Surgery and Medicine* 18:335-344; Poppas et al. (1996) *Lasers in Surgery and Medicine* 19: 360-368; Stewart et al. (1996) *Lasers in Surgery and Medicine* 19:9-16; Wider et al. (1991) *Plastic Reconstr Surg* 88:1018-1025). In tissue welding, the laser radiation is used to heat the tissue to temperatures at which collagen denatures and, upon cooling, the collagen molecules intertwine to form a 'weld'. Additionally, dye-enhanced thermal welding has been investigated (Bass & Treat (1995) *Lasers Surg and Med* 17: 315-349; Chuck et al. (1989) *Lasers Surg and Med* 9:471-477). In this method the dye selectively absorbs the laser energy and then releases heat to the desired area, reducing peripheral tissue damage. These methods, however, are not appropriate for the cornea due to the potential reduction in visual acuity that would result from the corneal deformation produced by thermal tissue damage. When performing PTB on the cornea, heating must be avoided.

Figure 5:
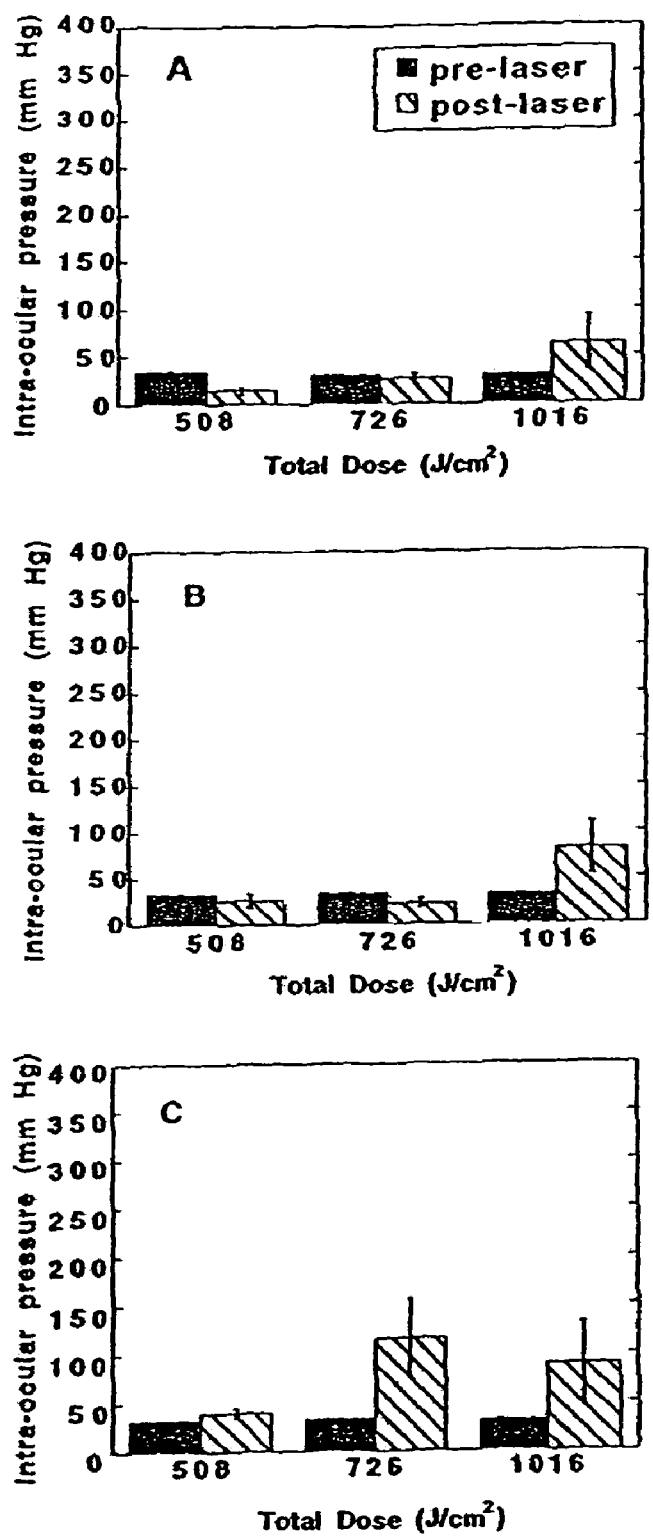
FIG. 5 shows graphs of mean IOPL values before and after PTB using Fl and 488 nm irradiation. Fl (40 μl, 0.6 mM) was applied to the incision surfaces then treated with the doses indicated using irradiances of: (A) 1.27 W/cm2, (B) 2.55 W/cm2 and (C) 3.82 W/cm2.

We evaluated the possibility that non-photochemical processes contribute to wound closure by comparing PTB produced by RB with that produced by fluorescein (Fl), a dye with a similar structure but which is not expected to induce protein cross-links. RB and Fl are both xanthene dyes. However, RB is halogenated (4 iodines and 4 chlorines) and the presence of these heavy atoms causes RB to be photochemically active (Lessing et al. (1982) *J Mol Struct* 84:281-292). Fl has a high quantum yield of fluorescence and lower quantum yield of triplet state formation than RB (Fleming et al. (1977) *JACS* 99:4306-4311) and will, therefore, produce a lower proportion of active species with the potential to produce collagen cross-links. A solution of 0.6 mM Fl was applied and irradiated using 488 nm laser light at the same range of irradiances used for RB and at doses from 508 J/cm$^2$ to 1016 J/cm$^2$ (FIG. 5). No increase in $IOP_L$ was observed for the incisions treated with the two lowest doses using the two lowest irradiances studied. However, at the highest dose for all irradiances an increase $IOP_L$ values was observed with values ranging from 63±30 to 89±42 mm Hg although this is much less efficient than RB (compare FIGS. 3 and 5). These results suggest that PTB is indeed produced by photochemical processes. The $IOP_L$ value of 116±40 mm Hg obtained using a dose of 762 J/cm$^2$ at 3.82 W/cm$^2$ (laser exposure time of 3 min, 10 sec) is considerably higher than any other observed using Fl. The sealing observed at the highest irradiance (3.82 W/cm$^2$) and dose (762 J/cm$^2$) suggests that some other effect is operating, such as a thermal mechanism under these high irradiance conditions.

Example 7

PTB Versus Sutures

The $IOP_L$ following PTB treatment, as described in Example 1, was compared to that obtained using sutures. Two interrupted radial sutures of black monofilament 10-0 nylon (Ethilon Inc.) were used to close the keratome incision. The sutures were placed in a radial fashion at approximately 90% corneal depth. $IOP_L$ values with sutures were approximately 230 mm Hg. This value is similar for the incisions closed with PTB treatment.

Example 8

In Vivo PTB

PTB was performed in vivo in New Zealand rabbits to repair two types of corneal wounds.

In group I 3.5-mm incisions were performed in 20 rabbit (New Zealand White) corneas. Dose and laser irradiance were varied in subgroups of five or more eyes for each condition and appropriate control eyes. Photoactivation was performed with a 514 nm Argon Laser. Wound leak and incisional bursting pressure of the treated and untreated rabbit eyes was determined in vivo, with the animals under anesthetic.

Group I wounds were healed using, e.g., 191 J/cm2, applying 1.5 mM RB. The immediate in vivo bursting pressure was 495±10 mm Hg for PTB treated eyes. Under the same conditions the values of the busting pressure in the control eye varied from 15 to 60 mm Hg. One day after surgery, the bursting pressure was the same for PTB treated eyes and control eyes (approximately 450±125 mmHg). At 14 days, the bursting pressure exceeded 500 mm Hg in both PTB-treated and control eyes.

In Group II, 6-mm Penetrating Keratoplasy (PK) incisions anchored by 4-16 sutures were performed in 16 rabbit corneas. Half of the corneas in each group underwent PTB where 1% Rose Bengal dye was applied to the wound edges followed by laser irradiation at fluence of 191 J/cm2. Photoactivation was performed with a 514 nm Argon Laser and a 532-nm CW Nd:YAG laser. Wound leak and incisional bursting pressure were determined in vivo in the immediate postoperative period. PTB-treated eyes showed an immediate bursting pressure of 410±70 mm Hg for the PTB-treated eyes, compared to 250±150 mm Hg for the control eyes with sutures alone. This result indicates that PTB is useful and effective as a supplement to sutures, as well as on its own.

The results described herein show that PTB is effective to seal, close, or heal a tissue, e.g., a corneal incision, in vivo, in a subject, e.g, an animal, or a human. The presence of a protein, e.g., a protein based sealant, e.g., fibrinogen, is not necessary to obtain a good tissue seal. PTB may be used instead of, or in addition to, other wound healing techniques, e.g., sutures.

Example 9

Assessment of PTB in Adhesion of Skin Grafts

Skin grafts and/or skin substitutes are widely used in surgical procedures such as skin transplantation, burn and ulcer wound management and plastic surgery. The primary qualities of successful skin grafts include rapid and sustained adherence to the wound surface and the ability to resist shear stress in order to be void-free and adherent.

To test the ability of PTB to quickly and effectively bond skin grafts to a wound site, an ex vivo model utilizing mini pigs was developed. The use of porcine models in wound healing is well known by those skilled in the art. The similarities between porcine wound healing and that of humans enable one to extrapolate the therapeutic results obtained in a porcine model system to a therapeutic result in humans.

Partial thickness skin grafts of approximately 0.020 inch (corresponding to the thick partial-thickness grafts used in clinical situation) were harvested from mini pigs (2 to 7 months old, weight 15 to 43 kgs) after euthanasia. The grafts were temporarily stored by wrapping the graft around gauze, which was soaked in phosphate buffered saline (PBS). The grafts were then immersed in vitrification fluid and cryo-preserved at −80° C. until needed (Fujita T et al. (2000) *J Burn Care Rehabil* 21: 304-9).

The skin grafts were freshly thawed on the day of the experiment and were washed with PBS before being cut into either square biopsies of 1 cm$^2$ area or into round biopsies of 0.6 cm diameter. The photosensitizer used was rose bengal (RB) (Sigma), which has the absorption maximum and absorption coefficient of 550 nm and 33,000 dm3/mol/cm at 514 nm, respectively. The RB was dissolved in PBS at concentrations of 0, 0.01, 0.1, and 1% (weight/volume) and kept in darkness before being applied liberally onto the dermal side of the skin grafts for time periods of 30 sec, 1, 2, 5, or 10 minutes, after which time the excess fluid was removed by aspiration and blotting. The round graft was attached to a suture loop while the square graft was secured onto a flat surface with sutures to prepare for the adherence test. The round layer was placed on top of the flat layer with the dye-stained dermal sides in approximation. Excess dye and air at the interface were removed by pressing and rubbing the graft surface over several layers of paper tissue, which was then removed without disturbing the graft interface.

The grafts were irradiated using a continuous-wave (CW) argon-ion laser (Innova 100; Coherent, Palo Alto, Calif.) at 514.5 nm. The approximated grafts were irradiated at a spot size of 0.6 cm diameter, transmitted through a 1 mm diameter quartz fiber. The irradiance of laser applied was 0.56 and 1.68 W/cm$^2$ while the dose-dependent response of the laser fluence from 126 to 504 J/cm$^2$ was determined. As a result, the exposure time ranged from 2.5 to 15 minutes. During this time the skin grafts were sprayed with PBS at regular intervals in order to prevent dessication.

Figure 6:
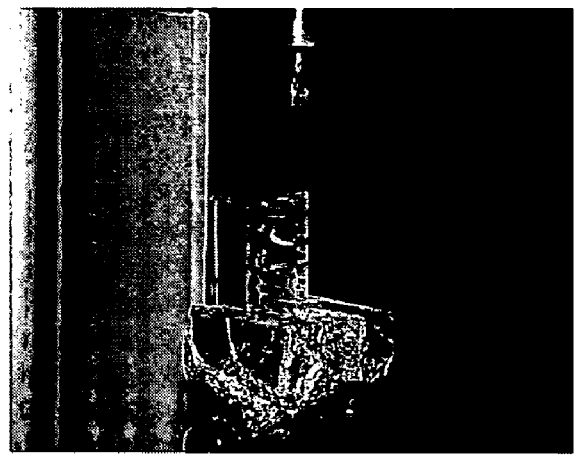
FIG. 6 shows a tensiometer coupled to a force transducer. Force was applied along the direction of the skin grafts at a constant speed of 12.7 mm/min by pulling on the pre-attached suture loop.

Following the irradiation, the adherence of the skin grafts was tested utilizing a tensiometer (Chartillon) coupled to a force transducer (DFA2, Ametek). The applied force versus the displacement of the force plate was acquired through the transducer and recorded by computer software (Labview 4.0, National Instrument). A force was applied along the direction of the skin grafts at a constant speed of 12.7 mm/min by pulling on the pre-attached suture loop (FIG. 6). Force-deflection plots were obtained, and the average force needed to separate the skin grafts was calculated and normalized by the size of the upper (round) graft (stress n/cm$^2$) using Kaleida-Gragh software. This measurement was used to compare the effects of the variations in concentration of RB, dose-response to the change in fluence level as well as differences between the two irradiance levels.

Figure 7:
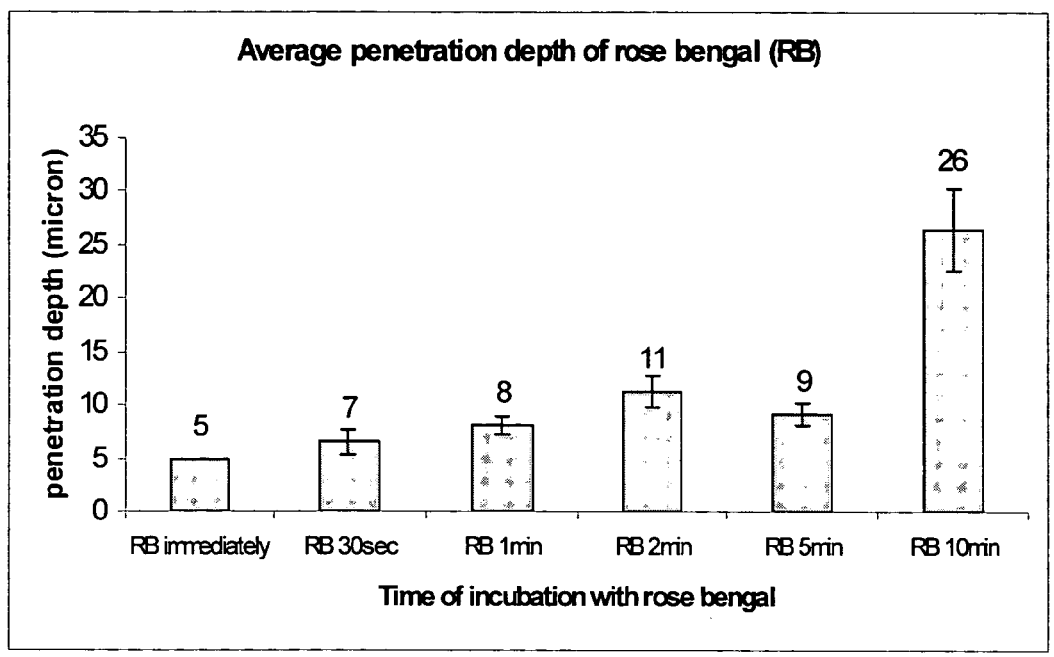
FIG. 7 shows a graph of the average penetration depth of rose bengal based on the association between dermal uptake and time of Rose Bengal exposure. An increase in exposure time to 10 minutes increased the depth of dermal uptake to approximately 25 microns.
Figure 8:
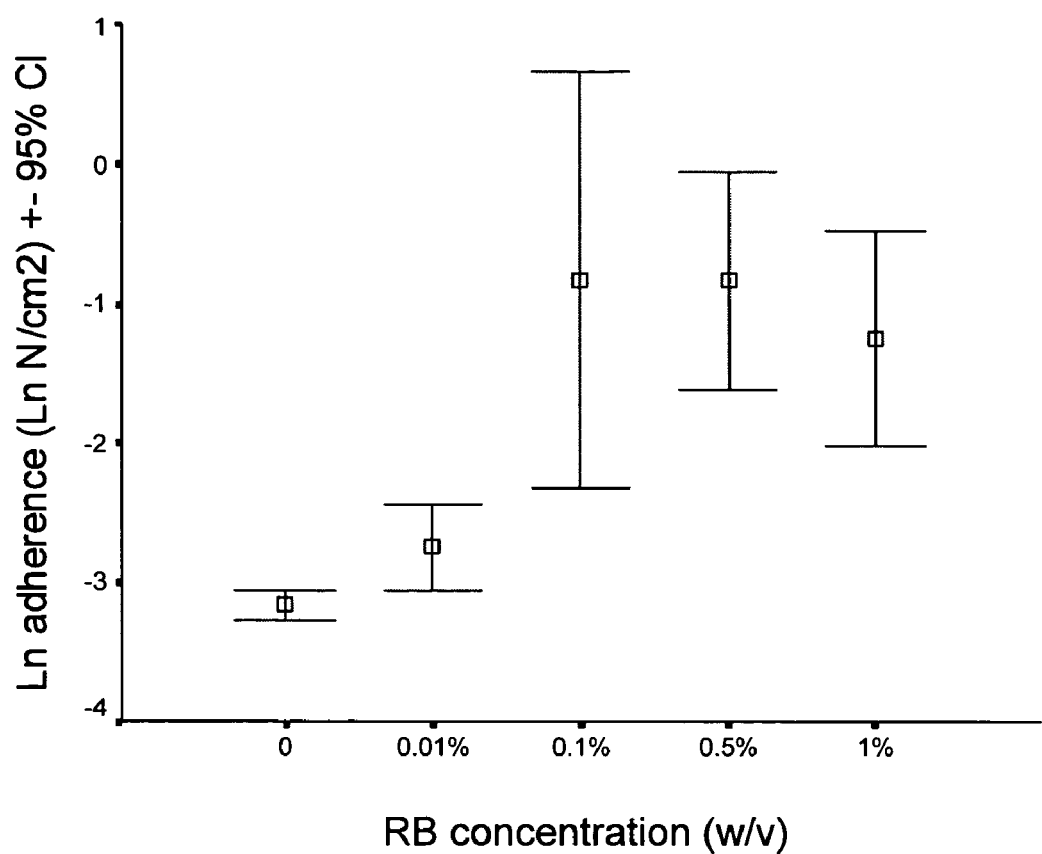
FIG. 8 shows a graph of the effect of Rose Bengal at various concentrations on laser-induced skin graft adherence. Use of Rose Bengal at a concentration of 0.1% (w/v) provided an optimal increase in adherence levels.
Figure 9:
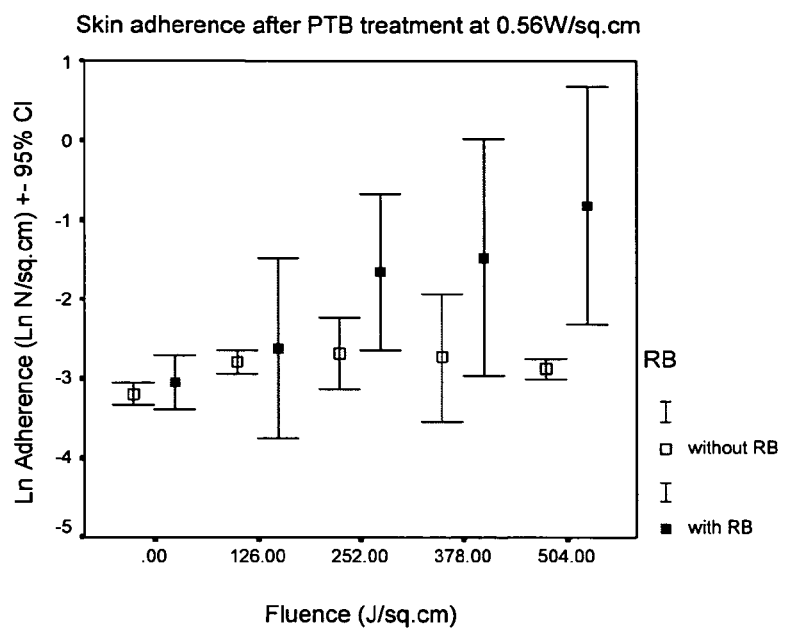
FIG. 9 shows a graph of the skin adherence after PTB at 0.56 (FIG. 9A) and 1.68 W/cm² (FIG. 9B). Irradiation levels of 0.56 and 1.68 W/cm² provided a positive dose-dependent relationship between the laser energy (fluence) and the adherence of the skin grafts.
Figure 9:
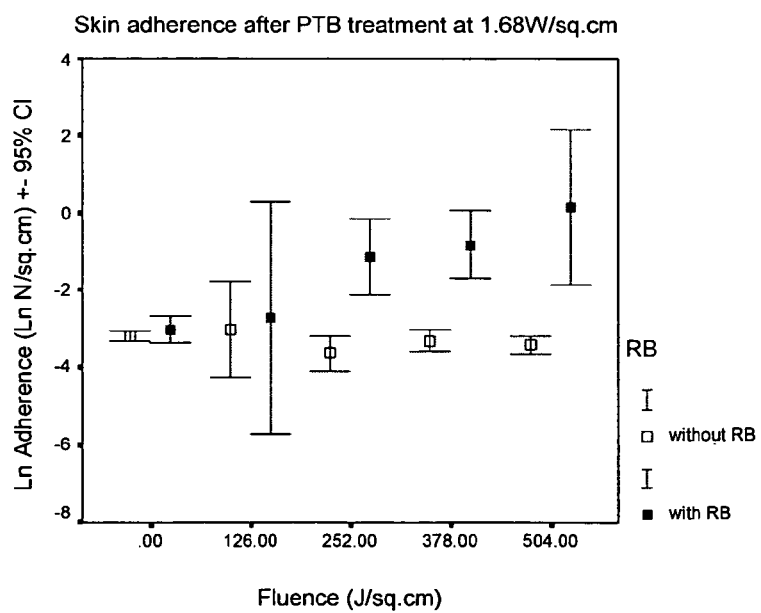

Frozen sections of tissue were analyzed using an eye-piece grid on a light microscope to determine the correlation between the time of exposure to RB and the distance of diffusion/penetration of RB. Exposure times of 5 minutes or less resulted in a dermal diffusion/penetration to a depth of approximately 10 microns. When exposure time was increased to 10 minutes, the depth of dermal diffusion/penetration increased to approximately 25 microns (FIG. 7). The depth of penetration of the dye will be minimized in order to prevent photochemical damage and intrinsic toxicity of the dye if any. Use of RB at a concentration of 0.1% (w/v) provided an optimal increase in adherence levels (FIG. 8). In addition, both irradiation levels (0.56 and 1.68 W/cm$^2$) provided a positive dose-dependent relationship between the laser energy (fluence) and the adherence of the skin grafts (FIGS. 9a and 9b).

Figure 10:
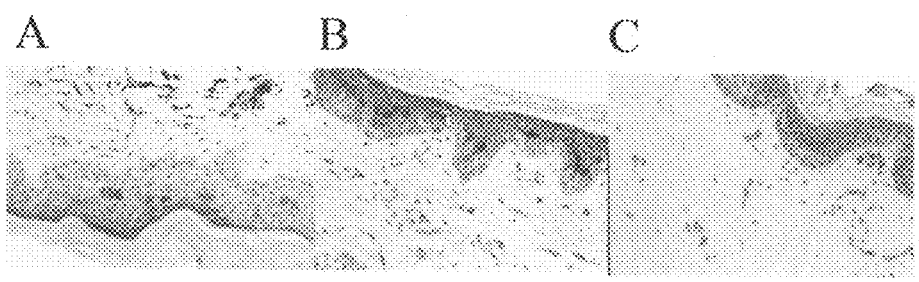
FIG. 10 shows cell viability and collagen organization. Following irradiation levels of both 0 (control) and 0.56 W/cm², skin grafts were viable, as indicated by NADH-diaphorase activity, shown as the dark blue precipitates in the cytoplasm contrasted by the red nuclear counterstain.

To test the viability of the cells after the irradiation, nicotinamide adenine dinucleotide (NADH-diaphorase) staining was carried out based on the methods described by Heisterkamp J et al. (1999) *Lasers Sug Med* 25(3): 257-62 and Neumann R A et al. (1991) *J Am Acad Dermatol* 25: 991-8. The skin grafts were exposed overnight to an incubation solution consisting of nicotinamide adenine dinuleotide (NADH) and nitroblue tetrazolium chloride (NBT) (Sigma). A water-insoluble blue precipitate formed at the points where NADH-diaphorase activity was present, indicating the viability of the cell. The grafts were washed in PBS and prepared in paraffin sections with a thickness of 5 microns. The sections were counterstained with nuclear fast red to show the cell nuclei. Following irradiation levels of both 0 (control) and 0.56 W/cm$^2$, the skin grafts and the cells were viable, as indicated by the dark blue precipitates in the cytoplasm of the cells contrasted by the red nuclear counterstain (FIGS. 10A and B). However, signs of thermal damage such as less intensive dark blue staining and disorganization of collagen bundles were found at high irradiance (1.68 W/cm2) as indicated in FIG. 10C.

Figure 11:
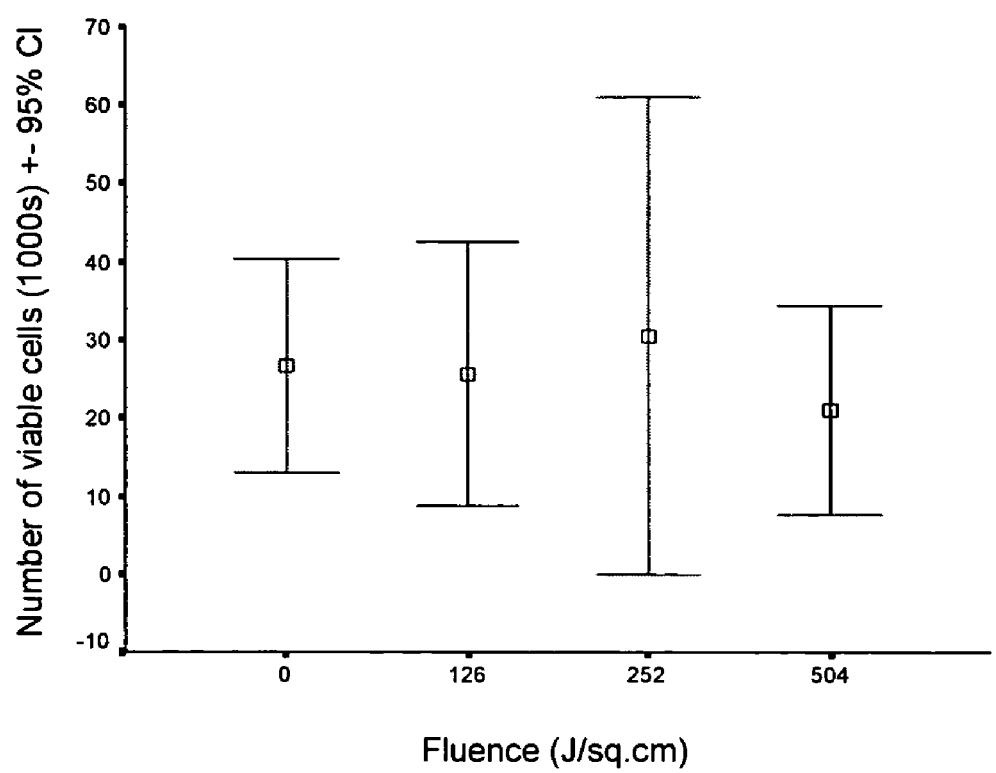
FIG. 11 shows cell viability after PTB of skin grafts at an irradiance of 0.56 W/cm² and various fluences.

The cell viability in the skin grafts was further assessed quantitatively by trypan blue exclusion assay. The upper grafts were chosen to be examined because they absorbed more light, and therefore would be damaged to a greater extent, if any, than the lower ones. Following irradiation, the upper skin grafts were incubated with 1 mg/ml dispase (Life Technologies, Rockville, Md.) in PBS overnight at 4° C. The epidermis was gently peeled off from the dermis and washed twice in PBS. Epidermal cells were released by incubating the epidermis with 0.25% trypsin-EDTA (Cellgro) at 37° C. for 15 minutes, accompanied by gentle agitation. Fetal calf serum (FCS) was added to inhibit trypsin activity and the cell suspension was then centrifuged at 2500 rpm for 10 mins. The cell pellet was washed once and re-suspended in PBS. The trypan blue exclusion assay was performed after mixing equal volumes of cell suspension and 0.2% (w/v) trypan blue and loading onto a hemocytometer. The number of viable cells released from each skin graft was calculated. After preparing a single cell suspension from intact epidermis, the cell viability was assessed (FIG. 11). The data for the number of viable cells per skin graft in different fluence groups is shown in FIG. 11. The number of viable cells per skin graft after irradiation (0.1% RB) at 126, 252 and 504 J/cm$^2$ was not significantly different from the control. Although there was a slight reduction in the number of viable cells in the 504 J/cm$^2$ group to ~80% of the control group, one-way ANOVA showed no statistical significant difference among the groups (p=0.899).

This example indicates that the utilization of low concentration RB, e.g., 0.1% and non-thermal irradiation (e.g., between approximately 0.1 and 1 W/cm$^2$) causes immediate skin graft adherence which maintains graft viability. As a non-thermal bonding method, this type of procedure minimizes or eliminates the tissue damage caused by thermal bonding methods. The procedures can be varied to incorporate various photosensitizers, appropriate laser light sources, concentrations of RB and amounts of irradiation. This type of treatment is beneficial in humans and would advantageously eliminate the need for or minimize the use of staples, sutures, glues, and other adhesives.

Example 10

Non-Thermal Adhesion of Skin Grafts

PTB advantageously proceeds by a non-thermal mechanism, as demonstrated by the following results.

Figure 12:
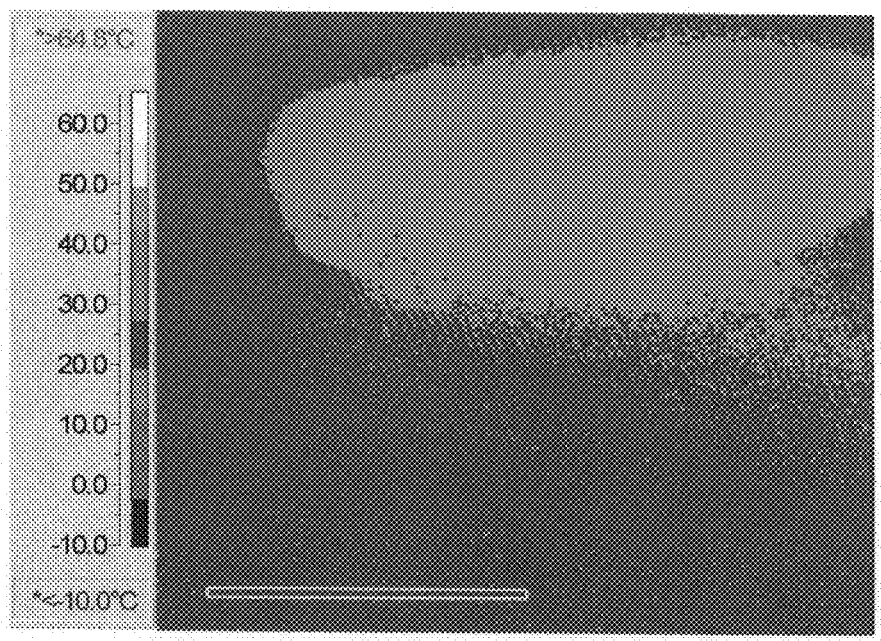
FIG. 12 shows typical thermographs of the focused edge of a cross-section of the skin graft during irradiation at 0.56
Figure 12:
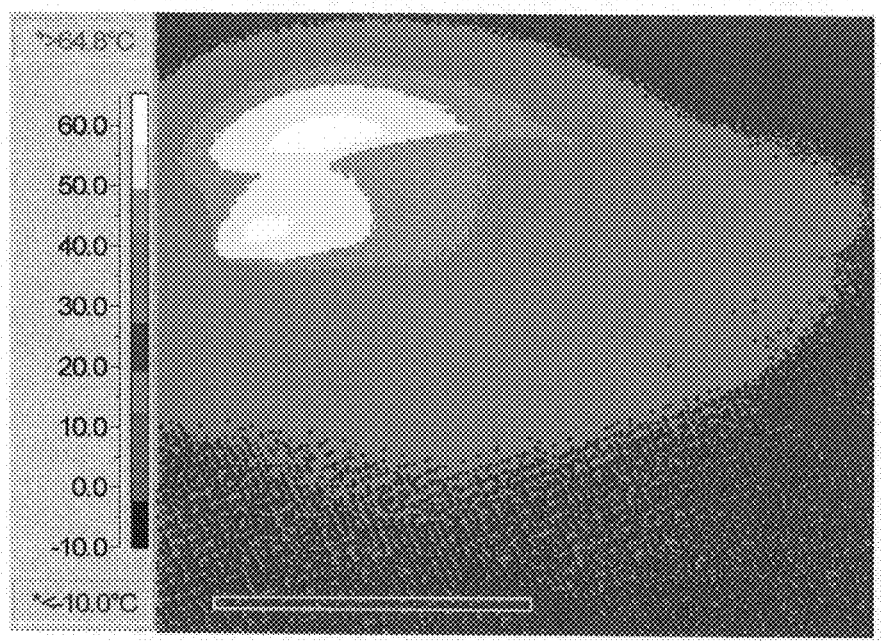
Figure 13:
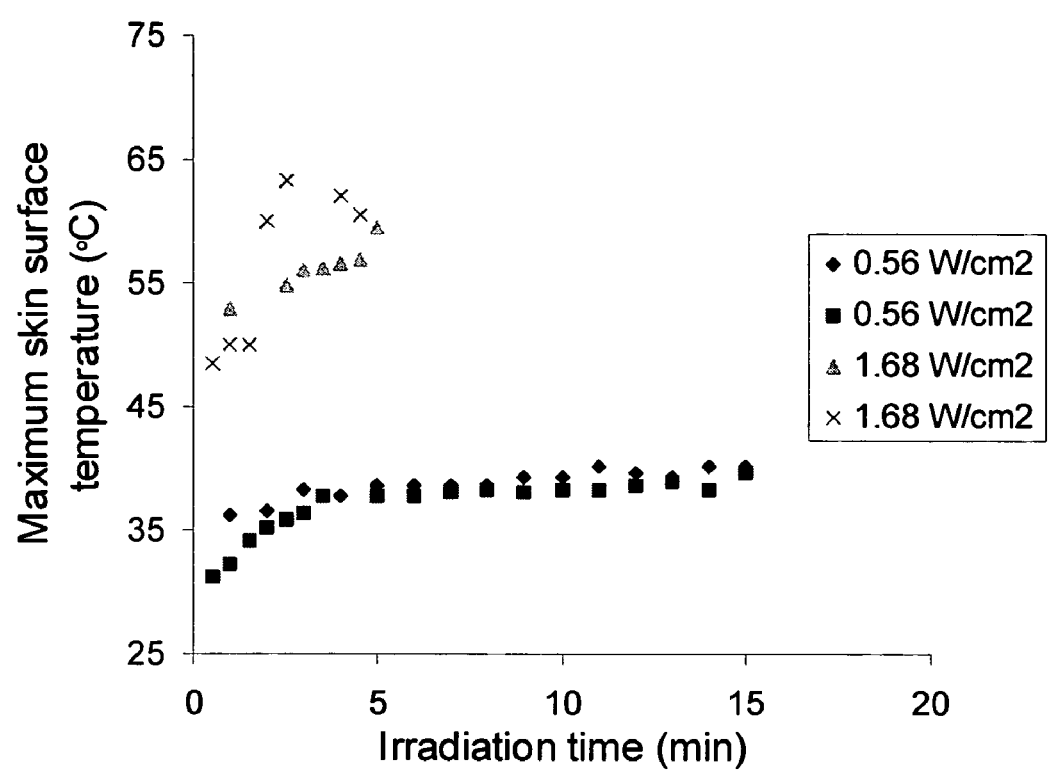
FIG. 13 shows a scatter plot of the maximal surface temperature of skin grafts during photochemical tissue bonding at 0.56 W/cm² and 1.68 W/cm², and up to a fluence of 504 J/cm².

The maximal temperature of skin grafts was recorded by a ThermaCAM infrared imaging radiometer (PM180, Inframetrics, Mass.). The ThermaCAM was set approximately 30° above the plane perpendicular to the direction of laser irradiation. The focus was set at one edge of the skin grafts before irradiation. Room temperature at 23° C. was set as the reference. Real time thermal images of the cross-sectional view of the focused edge of the skin grafts were captured at 30 second intervals throughout the irradiation (15 minutes for 0.56 W/cm$^2$ and 5 minutes for 1.68 W/cm$^2$). Images were analyzed by ThermaGRAM 95 software (Inframetrics, Mass.), which converted the values of the color-scale to temperatures. Typical thermographs of the cross-sectional view of the focused edge of the skin graft during irradiation at both 0.56 (FIG. 12A) and 1.68 W/cm$^2$ (FIG. 12B). The color images were interpreted using the color scale on the figure. The maximal temperature of the cross-sectional image of the skin grafts during the course of photochemical tissue bonding was recorded at 0.56 W/cm$^2$ and 1.68 W/cm$^2$, and up to 504 J/cm$^2$ (FIG. 13). At 0.56 W/cm$^2$, there was a gradual, slight increase in temperature throughout the 15 minutes of irradiation, from room temperature at 23° C., to an average of 31.2° C. after 1 minute of irradiation and then to 39.9° C. after 15 minutes of irradiation. By contrast, the maximal skin temperature reached 48.5° C. at 1 minute and then increased up to 59.5° C. by the end of a 5 minute irradiation using an irradiance of 1.68 W/cm$^2$.

The results demonstrate that PTB proceeds by a non-thermal tissue bonding procedure. The average of the maximal temperature of the skin grafts during the whole course of irradiation, 15 minutes, ranges from 31.2 to 39.9° C., which is far lower than the optimal coagulation temperature for laser thermal welding, 65-75° C. (Fung, L. C., et al., (1999) *Lasers Surg Med* 25: 285-290). This temperature change is expected to be even lower in vivo due to the thermal regulation in highly perfused skin.

To reduce the irradiation time during PTB, the irradiance was increased from 0.56 W/cm$^2$ to 1.68 W/cm$^2$ (a photochemical effect generally does not depend on the rate that the photons are absorbed). The high irradiance induced a greater temperature increase ranging from 48.5 to 59.5° C. during the 5 minute-long irradiation (FIG. 13). This increase in temperature also produced a decrease in cell viability and collagen organization as shown by NADH-diaphorase staining and the eosin counter staining, respectively (FIG. 10C). This is consistent with a previous report in which the critical temperature for cell death was 50-60° C. for a short period of heating of less than 3 minutes and ~50° C. for a longer period of 24 minutes (Heisterkamp, J et al. (1999) *Lasers Surg Med* 25(3): 257-62).

Irradiance is an important factor in photochemical tissue bonding. Maintaining the temperature below 40° C. is desirable for minimizing side effects. Temperature can be maintained by controlling irradiance conditions alone, or by including cooling agents such as spray coolants (Zenzie, H. H. et al. (2000) *Lasers Surg Med* 26: 130-44). In particular, surface coolants can be applied to protect the epidermis from thermal injury.

Example 11

Use of PTB to Enhance Bonding of Collagen Implants to Host Muscle Flap

An ex vivo experimental system was developed to investigate the effect of PTB on the bonding of an engineered, collagen-based, esophagus implant to host muscle flap tissue without the need for silicon tubing.

Figure 14:
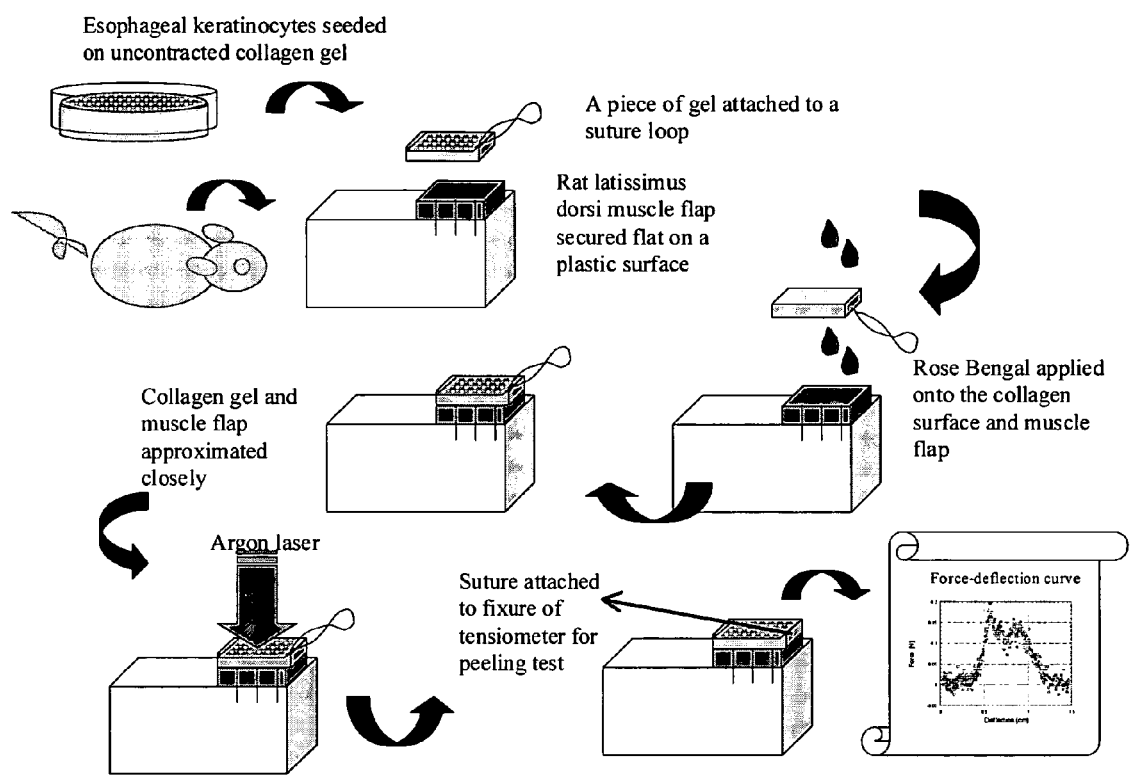
FIG. 14 shows a schematic diagram of photochemical tissue bonding of an esophagus implant to a host muscle flap.

FIG. 14 provides an overview of the experimental methods. Esophageal keratinocytes were seeded on uncontracted collagen gel (ICN Biomedicals) for about one week until confluence was reached. A 1×1 cm piece of seeded collagen gel was removed (implant) from the culture dish and a suture loop was laced through at its edge. An equivalently-sized section of rat latissimus dorsi muscle flap was secured onto a flat plastic surface with sutures. Rose bengal (RB) at 0.1% (w/v), a photosensitizer having an absorption maximum and absorption coefficient of 550 nm and 33,000 $dm^3$/mo/cm at 514 nm, respectively, was applied to the collagen side of the implant and the surface of the muscle flap and incubated for about two minutes. The esophagus implant and the muscle flap were approximated with the dye-treated surfaces facing each other by gently pressing over the esophagus implants without damaging the keratinocyte layer. Excess dye was removed by aspiration and blotting.

The approximated composite was photoactivated by irradiation with an optic fiber argon laser (514 nm), having a spot diameter of 1 cm. Two distinct irradiation conditions were used for separate samples in which the fluence of applied laser energy was 50 $J/cm^2$ (100 seconds) and 100 $J/cm^2$ (200 seconds), respectively. For both samples, the irradiance of applied laser was 0.25 $W/cm^2$. The composites were sprayed with PBS at 1 minute intervals to prevent desiccation. As controls, an RB untreated and nonirradiated composite (negative control), an RB treated and nonirradiated composite (RB control), and a RB untreated and irradiated composite (laser control) were prepared concurrently.

Figure 15:
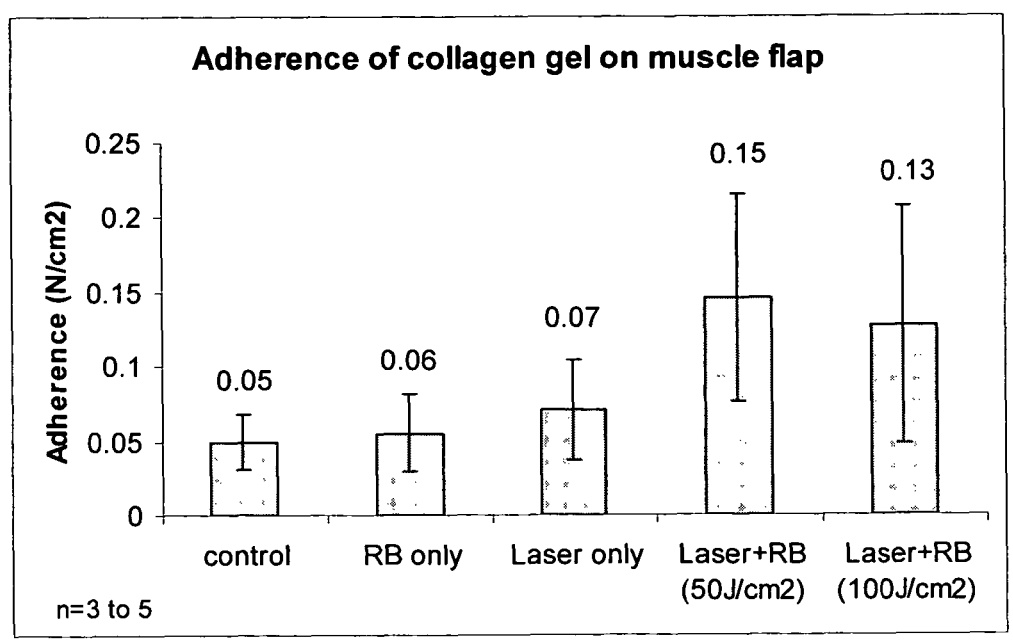
FIG. 15 shows the mean adherence of collagen gel on muscle flap of the control, Rose Bengal control, Laser control and the PTB treated groups.

Following irradiation, the adherence of the collagen-based esophageal implant to the host muscle flap was tested for the 50 $J/cm^2$ sample, 100 $J/cm^2$ sample, and the three controls, using a tensiometer (Chartillon) coupled to a force transducer (DFA2, Ametek). The adherence ($N/cm^2$; N=force applied, $cm^2$=area of collagen implant) of the collagen implant on the muscle flap was determined from the force-deflection curve, generated by plotting the amount of peeling force applied to the collagen implant to the force plate displacement level of the force transducer. It was observe that the mean adherence measurements determined for the negative, RB, and laser controls were 0.05, 0.06, and 0.07 $N/cm^2$, respectively (FIG. 15). In contrast, the adherence measurements determined for the 50 and 100 $J/cm^2$ composite samples were 0.15 and 0.13 $N/cm^2$, respectively (FIG. 15). Statistical analysis using the Kruskal Wallist test showed a statistically significant result at a significance level of 0.1 (p=0.09). The increase in adherence of the 50 and 100 J/cm irradiated composite samples suggests clinical importance.

Figure 16:
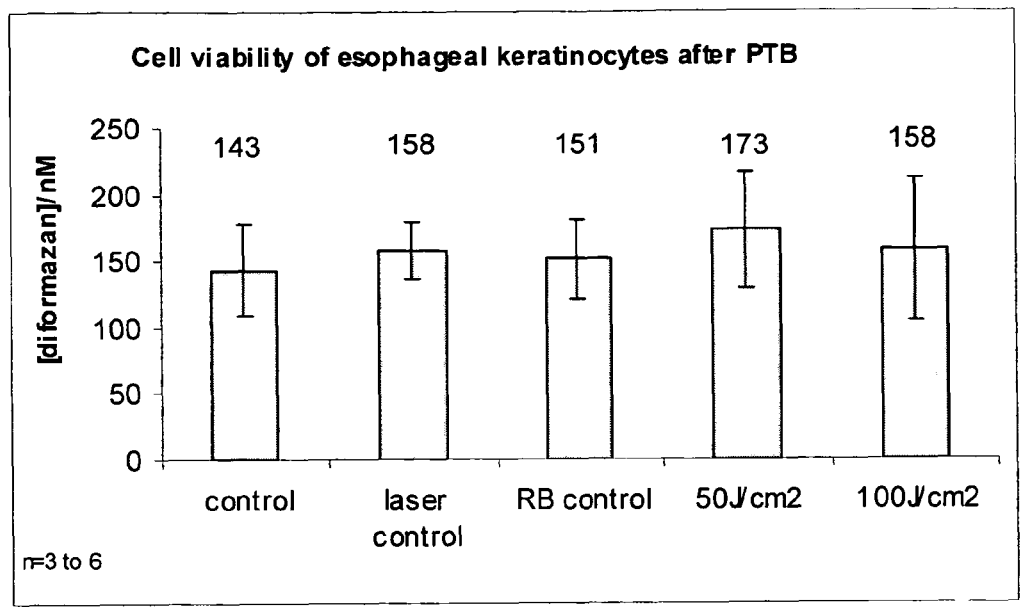
FIG. 16 shows the viability of esophageal keratinocytes after photochemical tissue bonding treatment.

The viability of the photoactivated cells was also assessed. Nicotinamide adenine dinucleotide (NADH-diaphorase) staining was carried out based on the methods described by Heisterkamp J et al. (1999) *Lasers Sug Med* 25(3): 257-62 and Neumann R A et al. (1991) *J Am Acad Dermatol* 25: 991-8. Following irradiation, the keratinocyte layer was gently peeled away from the collagen gel and was exposed overnight to an incubation solution consisting of nicotinamide adenine dinucleotide (NADH) and nitroblue tetrazolium chloride (NBT) (Sigma). The viability of the cells was indicated by the formation of a water-insoluble blue precipitate (diformazan), which corresponded to areas with NADH-diaphorase activity. The insoluble blue precipitate was dissolved in DMSO (an organic solvent) and quantified by measuring the optical density (OD) at 550 nm against a commercially available standard. The negative control, RB control, and the laser control composites were also tested using identical conditions. It was determined for the negative control, RB control, laser control, 50 $J/cm^2$ composite sample, and the 100 $J/cm^2$ composite sample that the levels of corresponding blue precipitate were 143, 151, 158, 173 and 158 diformazan/nM after photochemical tissue bonding treatment (FIG. 16). It was determined by non-parametric Kruskal Wallis test that the differences between measurements was not significant (p=0.596), indicating that viability was the same between treated and non-treated controls.

The current ex vivo study demonstrates that photochemical tissue bonding is able to increase the adherence of collagen-based esophagus implants to the host muscle flap tissue. The mean adherence measurements of the negative, RB, and laser controls were less than the mean adherence measurements of the PTB treated groups. The bonding strength produced reduces or even eliminates the need for surgical supporting aids, such as silicon tubing, during integration of collagen-based scaffold tissue implants. Viability assessment of the top keratinocyte layer after PTB treatment was shown to be the same as the controls, indicating that PTB is a safe procedure that retains high cell viability.

Example 12

Use of PTB in Ruptured Tendons

Repair of ruptured or torn tendons and ligaments is often accomplished by surgically reattaching the tissue or closing the laceration. In addition to the physiological repair, the wound must return to functional integrity.

To test the ability of PTB to quickly and effectively bond ruptured tendons, an in vitro model utilizing bovine tendons was developed. The use of bovine models in wound healing is well known by those skilled in the art. The similarities between bovine wound healing and that of humans enables one to extrapolate the therapeutic results obtained in a bovine model system to a therapeutic result in humans.

Fresh bovine achilles tendons were obtained and stored at 40° C. until use. The tendon was cut into dumbbell-shaped 5 cm strips with the central 3 cm strip at an approximate cross-sectional area of 1 mm by 1 mm, and were irrigated constantly with phosphate buffered saline (PBS) to prevent desiccation.

Rupture of the tendon was induced by weakening the central 1 cm of the tendon with a surgical blade and mechanically pulling it apart. A solution of Rose Bengal at various concentrations (0.1, 0.5 and 1.0% weight per volume in PBS) was applied to the ends of the ruptured tendons for two minutes, after which the ruptured ends were approximated and the excess dye was removed.

The ruptured ends of the tendon were crossed over each other with an overlap of approximately 1 cm before being wrapped by several layers of tissue paper. The tissue wrapped tendon was rolled and pressed in order to approximate the ruptured ends and remove the excess dye. The tissue paper was carefully removed before the tendon was placed between two glass slides that were then clipped together.

The center of the approximated tendon was irradiated with an argon laser (514 nm), having a spot size of 1 cm in diameter, which was transmitted through an optic fiber. The laser was applied with an irradiance of 0.5, 1.0, or 1.5 $W/cm^2$, while the fluence of laser energy applied was 125, 250, 500, or 750 $J/cm^2$. The exposure time ranged from 1 min and 23 seconds to 25 minutes.

Control tendons were ruptured in the same manner, however treatments consisted of application of Rose Bengal and approximation of the tendon ends without laser irradiation, approximation of the tendon ends with laser irradiation but no exposure to rose bengal, and approximation of the ends with no further treatment.

Figure 17:
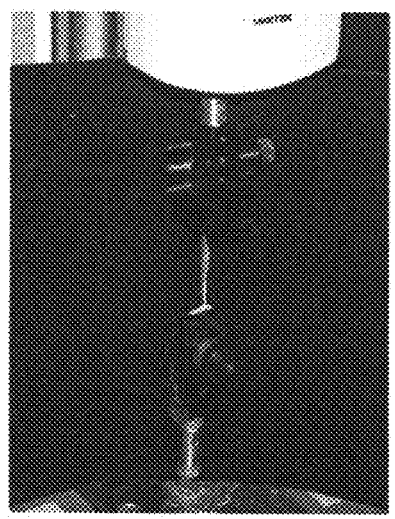
FIG. 17 shows a strip of tendon attached to the fixture of the tensiometer. Cyclic loading of the tendon was conducted by stretching the tendon at a magnitude of 0.5 mm for 6 cycles, before tendon was pulled to failure at a constant speed of 100 mm/min.
Figure 18:
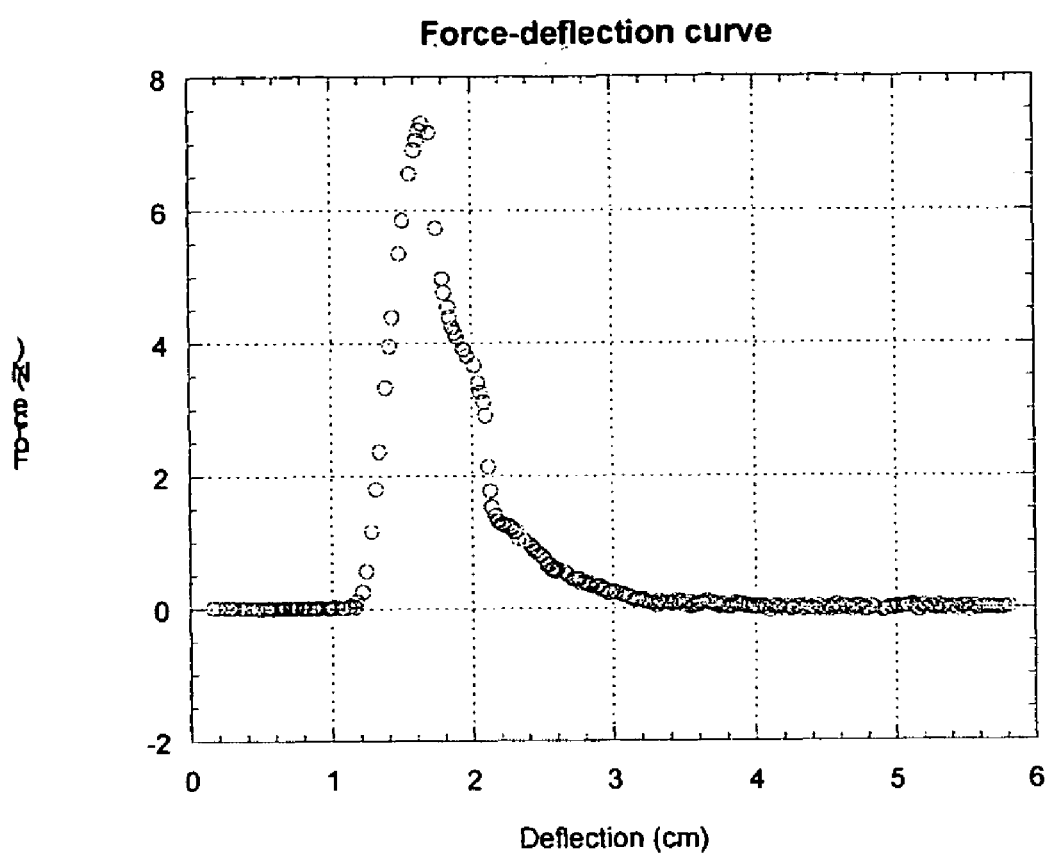
FIG. 18 shows a typical force-deflection curve obtained by measurements from the tensiometer.

To test the effectiveness of the photochemical tissue bonding, immediately after photochemical tissue bonding, the tendon strips were attached to the fixture of a tensiometer, which was coupled to a force transducer (FIG. 17). The tendon was held at a straight and vertical position, and cyclic loading of the tendon was conducted by stretching the tendon for a magnitude of 0.5 mm for 6 cycles. The tendon was brought back to a zero deflection position before being pulled to failure at a constant speed of 100 mm/min. The peak force needed to rupture the tendon was recorded, and a typical force-deflection curve was obtained (FIG. 18). The ultimate stress and stiffness (peak force for tendon rupture normalized by the cross-sectional area, and slope of the linear region of the force-deflection curve, respectively) were calculated from the force-deflection curve.

Figure 19:
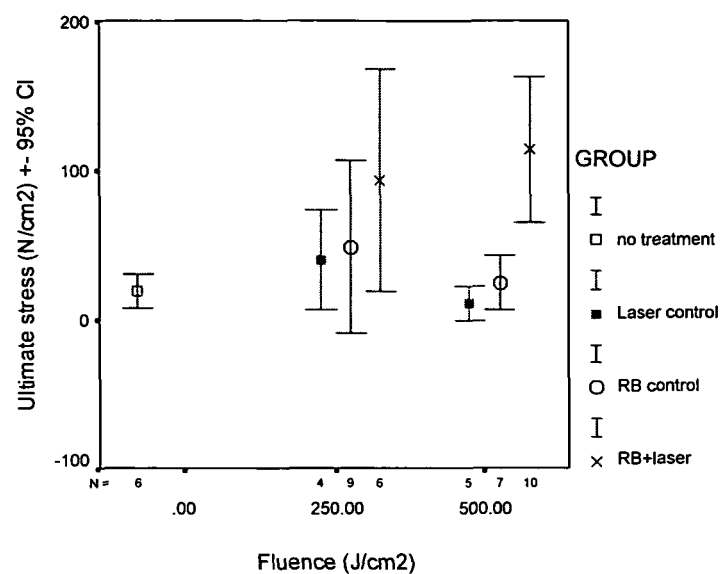
FIGS. 19A and 19B show a graph of the ultimate stress and stiffness in ruptured tendons treated with laser only, Rose Bengal only, laser and Rose Bengal or no treatment. Combinatory use of visible light (argon laser) and Rose Bengal significantly increased the ultimate stress and the stiffness.
Figure 19:
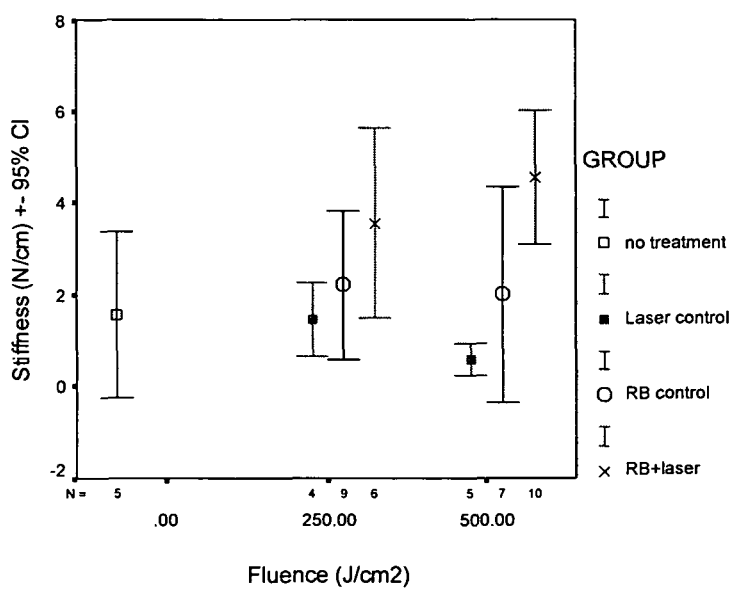

The ruptured tendons treated with visible light (argon laser) and a photoactivated dye (Rose Bengal) showed a significant increase in the ultimate stress and stiffness compared to the controls (FIGS. 19A and 19B). The fluence dose response was studied up to 750 J/cm$^2$, however, apparent dehydration in the tendon was reported in the highest dosage group.

Figure 20:
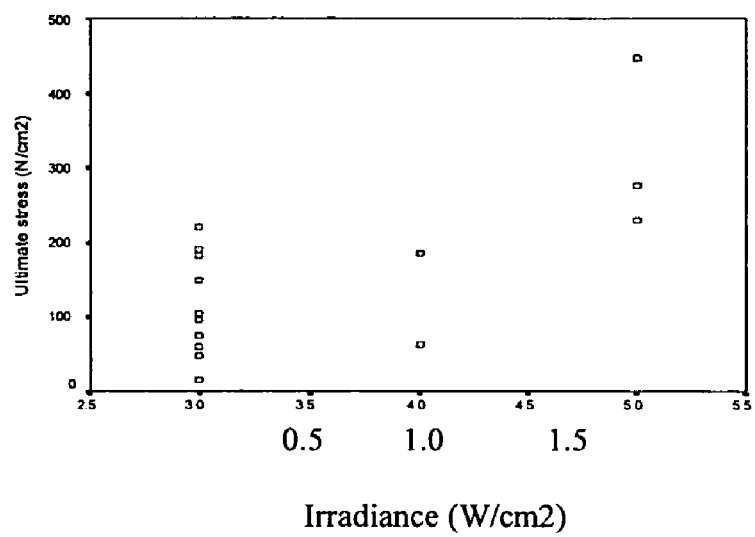
FIGS. 20A and 20B show graphs of the ultimate stress and stiffness in ruptured tendons at a fixed fluence dosage of 500 J/cm², while increasing the laser power density. Ultimate stress was significantly increased, but stiffness was not.
Figure 20:
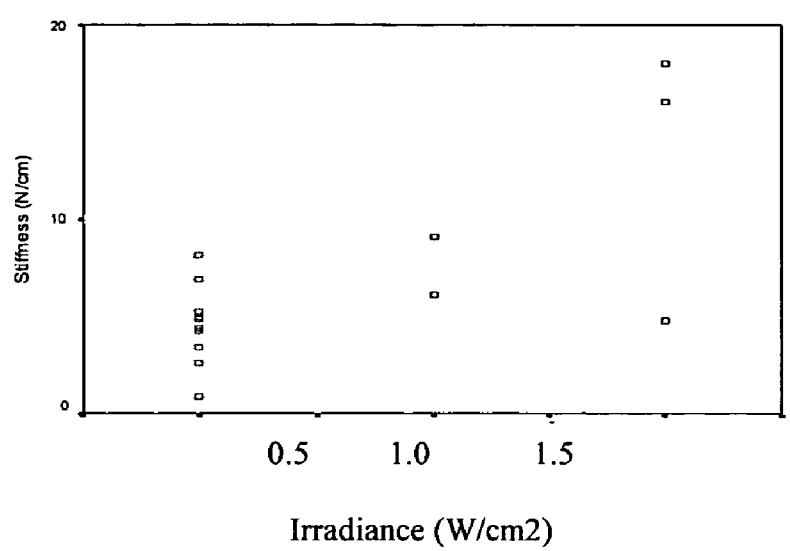

At a fixed fluence dosage of 500 J/cm$^2$, increasing the power density (irradiance) significantly increased the ultimate stress (p=0.034), but not the stiffness (p=0.088 of the ruptured tendon (FIGS. 20A and 20B). Dehydration of the tendon was noticed at the highest irradiance (1.5 W/cm$^2$).

Figure 21:
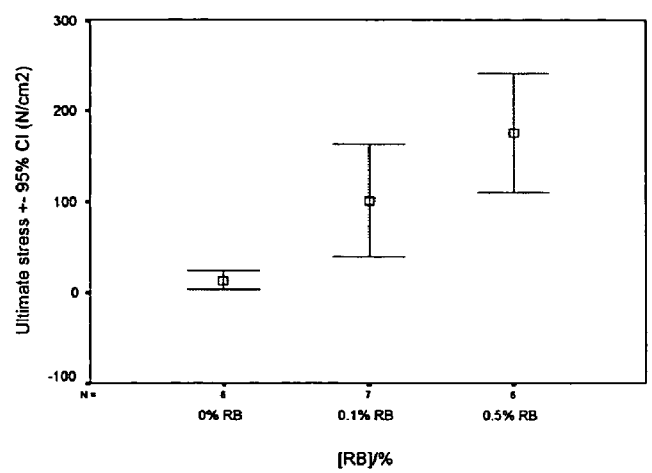
FIGS. 21A and 21B show a graph of the ultimate stress and stiffness in ruptured tendons at increasing Rose Bengal concentrations.
Figure 21:
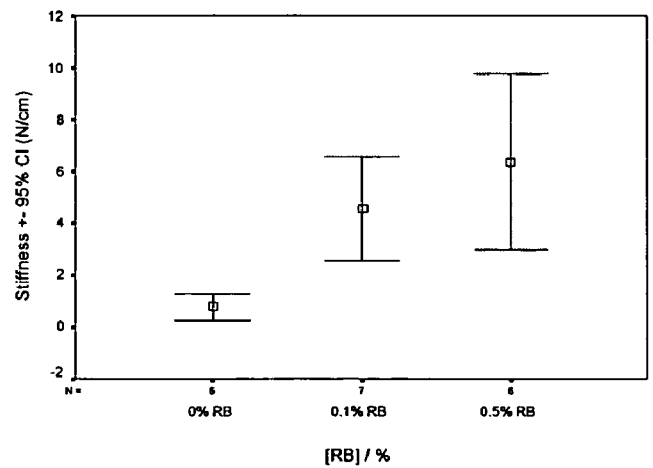

The concentration of Rose Bengal was varied to determine its influence on the photochemical tissue bonding. Dosages of 0.0, 0.1, 0.5 and 1.0% (w/v in PBS) were tested, with the results showing a significant increase in both the ultimate stress and the stiffness at higher Rose Bengal concentrations (FIGS. 21A and 21B). When 1.0% Rose Bengal was tested, dehydration of the tendon was noticed.

Healthy tendons were also placed in the tensiometer, and were pulled to the point of failure. Following failure, they were treated with photochemical tissue bonding at 500 J/cm$^2$ fluence and again pulled to failure to study the percentage of recovery of mechanical properties. Immediately after the photochemical tissue bonding, the ultimate stress and the stiffness returned to approximately 59.66% and 52.75% of the healthy tendon, respectively (Table 1).

TABLE 1

| Group | Mean change in ultimate stress % (95% CI) | Mean change in stiffness % (95% CI) | n |
| --- | --- | --- | --- |
| Laser control | 17.07 (4.19, 29.95) | 35.00 (0.75, 69.25) | 6 |
| Dye control | 24.18 (6.57, 41.79) | 20.65 (10.16, 31.14) | 6 |
| Laser + Dye | 59.66 (8.71, 110.61) | 52.75 (24.05, 81.45) | 7 |

This example indicates that the utilization of low concentration RB and non-thermal irradiation (e.g. between approximately 0.5 and 1 W/cm$^2$) causes immediate tendon bonding which enhanced the mechanical properties, including the ultimate stress and the stiffness, of the ruptured tendon immediately after the bonding procedure. As a non-thermal bonding method, this type of procedure eliminates the tissue damage caused by thermal bonding methods. The procedures can be varied to incorporate various photosensitizers, appropriate laser light sources, concentrations of RB and amounts of irradiation. This type of treatment is beneficial in humans and would advantageously eliminate the need for or minimize the use of staples, sutures, glues, and other adhesives.

Example 13

Use of PTB in Ruptured Tendons In Vivo

The tensile strength was tested one week after in vivo bonding of rat achilles tendon. The bonding was carried out in vivo. The tendon was removed and tested ex vivo. The peak force needed to break the tendon was normalized by the cross sectional area of the tendon. The elasticity of the tendon was also calculated from a stress-strain curve obtained during the tensile strength test.

Figure 22:
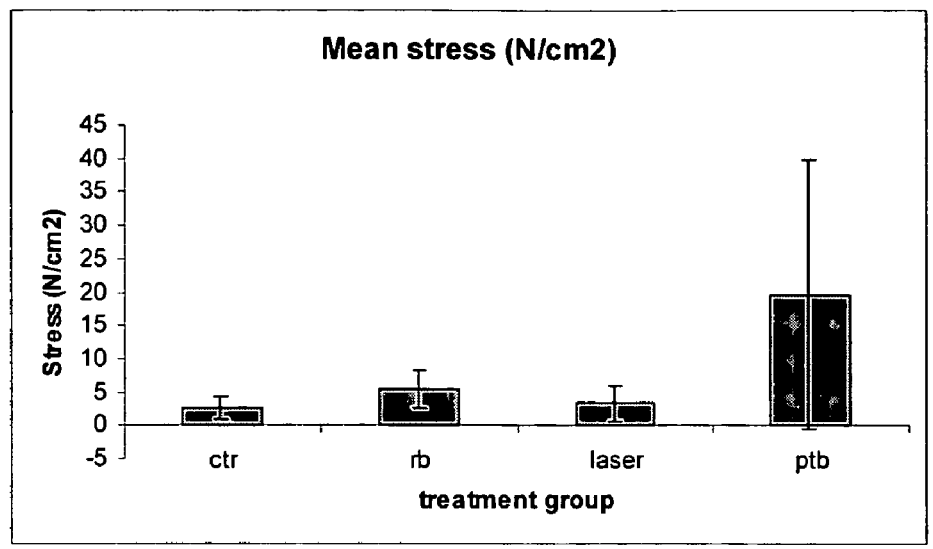
FIGS. 22A and 22B show the ultimate stress and the stiffness following in vivo PTB treatment compared to the controls.
Figure 22:
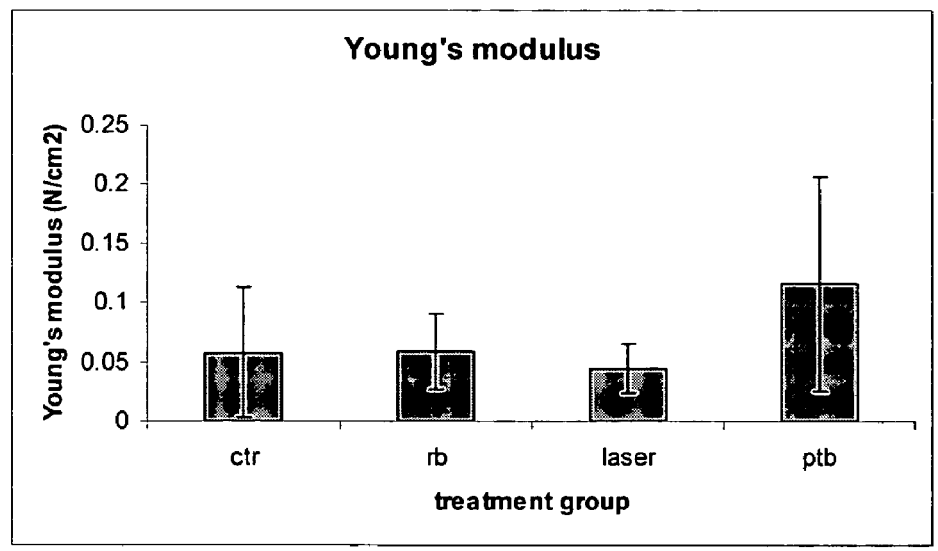

PTB treatment significantly increased the ultimate stress (p=0.004), which is the peak force for tendon rupture normalized by the cross-sectional area and the stiffness (p=0.006), which is the slope of the linear region of the force-deflection curve, of ruptured tendons (FIGS. 22A and 22B).

Figure 23:
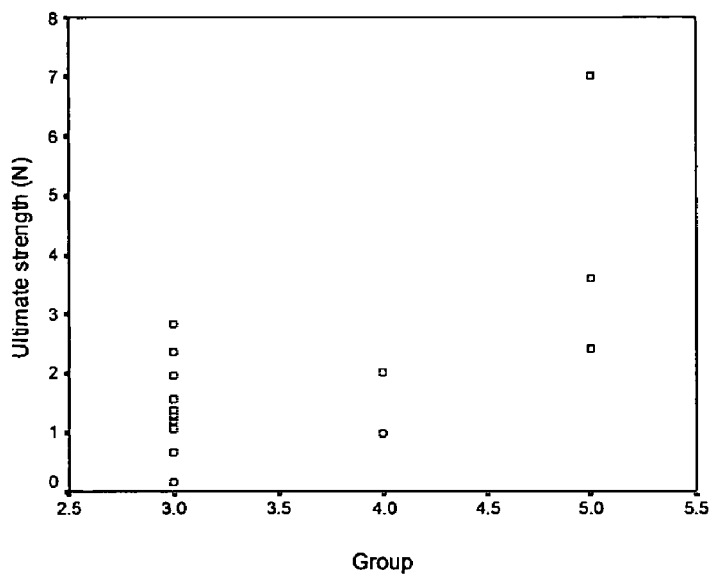
FIGS. 23A and 23B show an increase in the ultimate stress ($p=0.034$) but not the stiffness ($p=0.088$) of the ruptured tendon in vivo following irradiance at a fixed fluence dosage of 500 J/cm².
Figure 23:
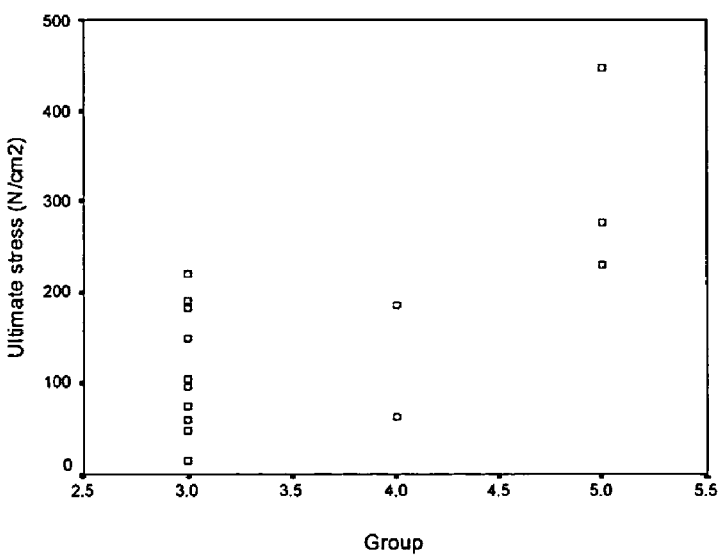

At a fixed fluence dosage of 500 J/cm$^2$, increasing the laser power density, or the irradiance, significantly increased the ultimate stress (p=0.034) but not the stiffness (p=0.088) of the ruptured tendon (FIGS. 23A and 23B).

Figure 24:
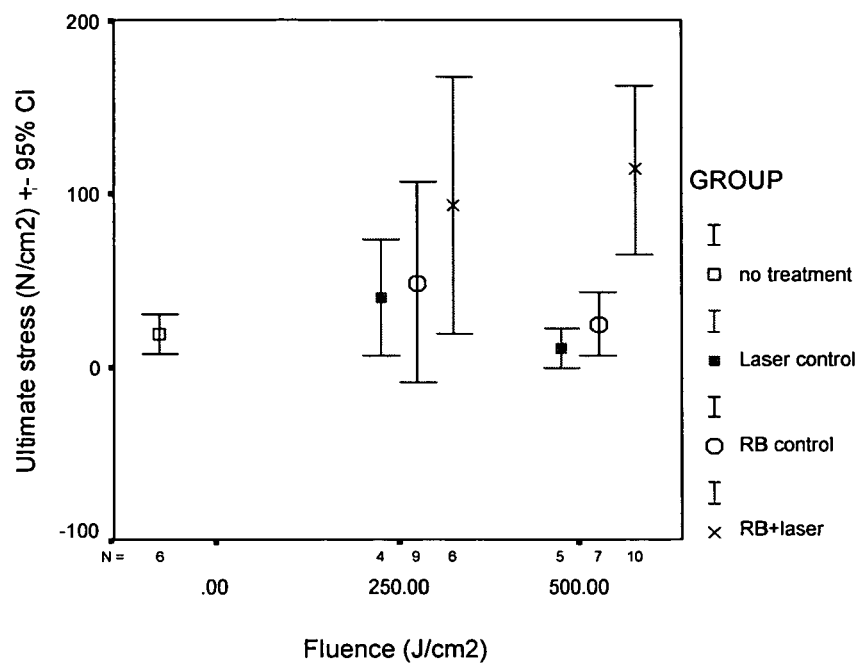
FIGS. 24A and 24B show the statistically significant dose-response in vivo in both the ultimate stress ($p=0.002$) and the stiffness ($p=0.004$) of the photochemically bonded tendon.
Figure 24:
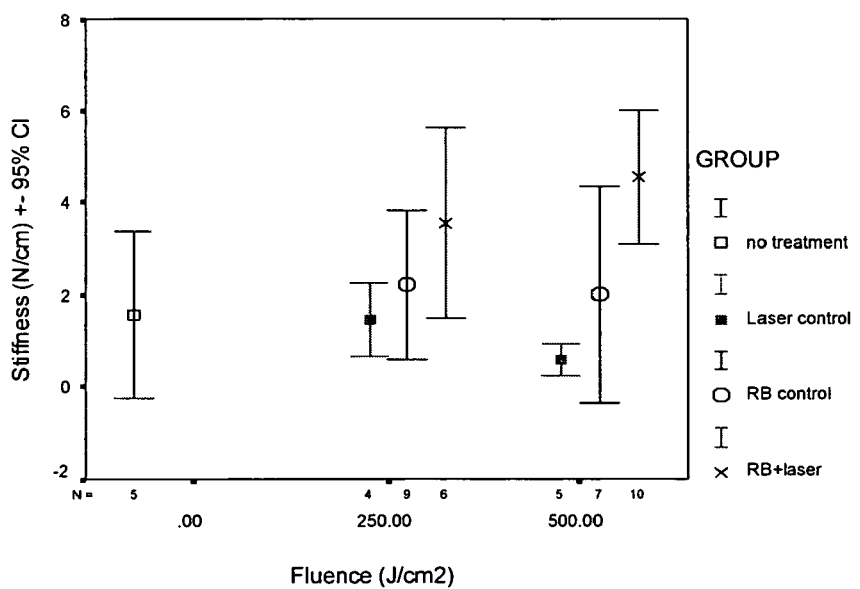

At a fixed irradiance of 1.0 w/cm$^2$, increasing the fluence dosage induced a significant increase in both the ultimate stress (p=0.002) and the stiffness (p=0.004) of the photochemically bonded tendon (FIGS. 24A and 24B).

Example 14

Use of PTB in an In Vivo Rat Sciatic Nerve Repair Model

Methods of the present invention can be used to effectively repair neural tissue.

Presently, the goal in peripheral nerve repair is to maximize axonal regeneration while minimizing scar/neuroma formation and operative time. In addition to creating scar tissue, gaps created by suture-based repair compromise the nerve's environment by allowing the entrance of inflammatory cells, such as macrophages, as well as the escape of regenerating axons and essential neurotrophic and neurotropic factors. The methods described herein are designed to overcome these obstacles.

Photochemical tissue bonding was performed on a rat sciatic nerve model of peripheral nerve injury. Various experimental and control surgical protocols were tested, each being tested on a group of 10 rats (n=10).

Adult, male, 300 g Fischer rats (NCI) were anesthetized with pentobarbital (40 mg/kg IP) and weighed. The left hind limb was shaved with clippers and prepared with povidone-iodine solution. Under semi-sterile conditions using a double-headed operative microscope, a longitudinal incision along the lateral aspect of the left hind limb was made to expose the sciatic nerve via a muscle splitting incision. A 1 cm segment of sciatic nerve was dissected free from all surrounding tissues and then sharply transected using microsurgical scissors approximately 1 cm from the pelvic hiatus. Animals were then randomly assigned to one of the four treatment groups shown below in Table 2.

TABLE 2

| Experimental Group | Surgical Repair Procedure | PTB with Rose Bengal | Number of Animals |
| --- | --- | --- | --- |
| A | Standard Suture | No | 10 |
| B | No Surgical Repair | No | 10 |
| C | Epineurial Cuff | No | 10 |
| D | Epineurial Cuff | Yes | 10 |

In Experimental group A, following transection the proximal and distal segments of the sciatic nerve were microsurgically repaired in an end-to-end fashion, by placing multiple epineurial 10-0 nylon sutures.

In experimental group B, where the sciatic nerve was transected but not repaired, the distal sciatic nerve segment was buried in the thigh musculature and anchored using a 10-0 nylon suture.

Figure 25:
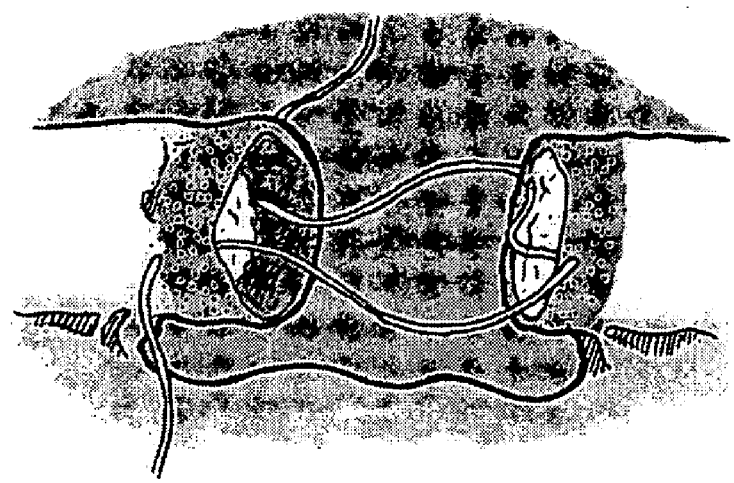
FIG. 25 shows a schematic illustration of the procedure for the formation of epineurial cuffs, as described in Example 14.
Figure 25:
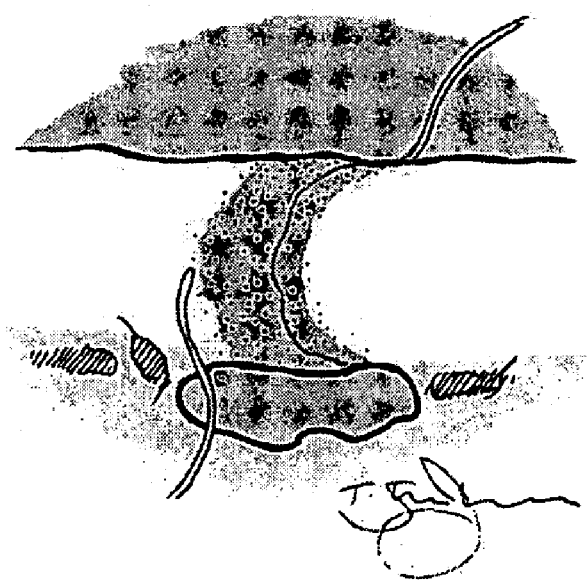

In experimental group C, "epineurial cuff" procedure was performed, as illustrated in FIG. 25, to produce a protrusion or "cuff" of the epineurial tissue extending beyond the inner neural tissue. Following transection, the epineurial cuff of the distal segment was gently retracted and approximately 2 mm of endoneurium was sharply removed. A single 10-0 nylon suture was used as an aid to draw the proximal sciatic segment into the distal sciatic cuff, as illustrated in FIG. 25. The suture was then gently removed. This "cuffing" procedure served to maximize the area of surface contact between the proximal and distal stumps of the transected nerve.

In experimental group D, the transected nerves of the rats were treated as for group C, except that PTB treatment was performed by applying 25 µl of 0.1% RB dye to the exposed epineurial surfaces of the sciatic nerve and left in place for 30 seconds prior to alignment of the nerve segments. Endoneurium exposed to the dye was removed. The repair site was then exposed to green laser light at 514 nm. The nerve was then rotated 180° and the irradiation was repeated.

After completion of the above surgical and/or PTB procedures, and after insuring adequate hemostasis, all wounds were closed in a subcuticular fashion with 4-0 absorbable, braided sutures. Once the animals were awakened from anesthesia, only those animals moving comfortably and tolerating food and liquids were used in subsequent experiments. All animals received Buprenex (0.03 mg/kg IM) postoperatively and then every 12 hrs for 3 days.

Initially, the left lower leg of all rats was non-functional, as is to be expected after sciatic nerve transection.

Functional assays for sciatic nerve repair were performed as follows. At 90 days following surgery, animals were sacrificed. A "gastrocnemius muscle mass assay" was used to assess functional nerve repair. This assay makes us of the phenomenon whereby denervated muscles waste away and lose mass, over time. The weight of the gastrocnemius muscle of the treated hind limb of each rat was compared to that in the untreated hind limb, which acted as an internal control.

Figure 26:
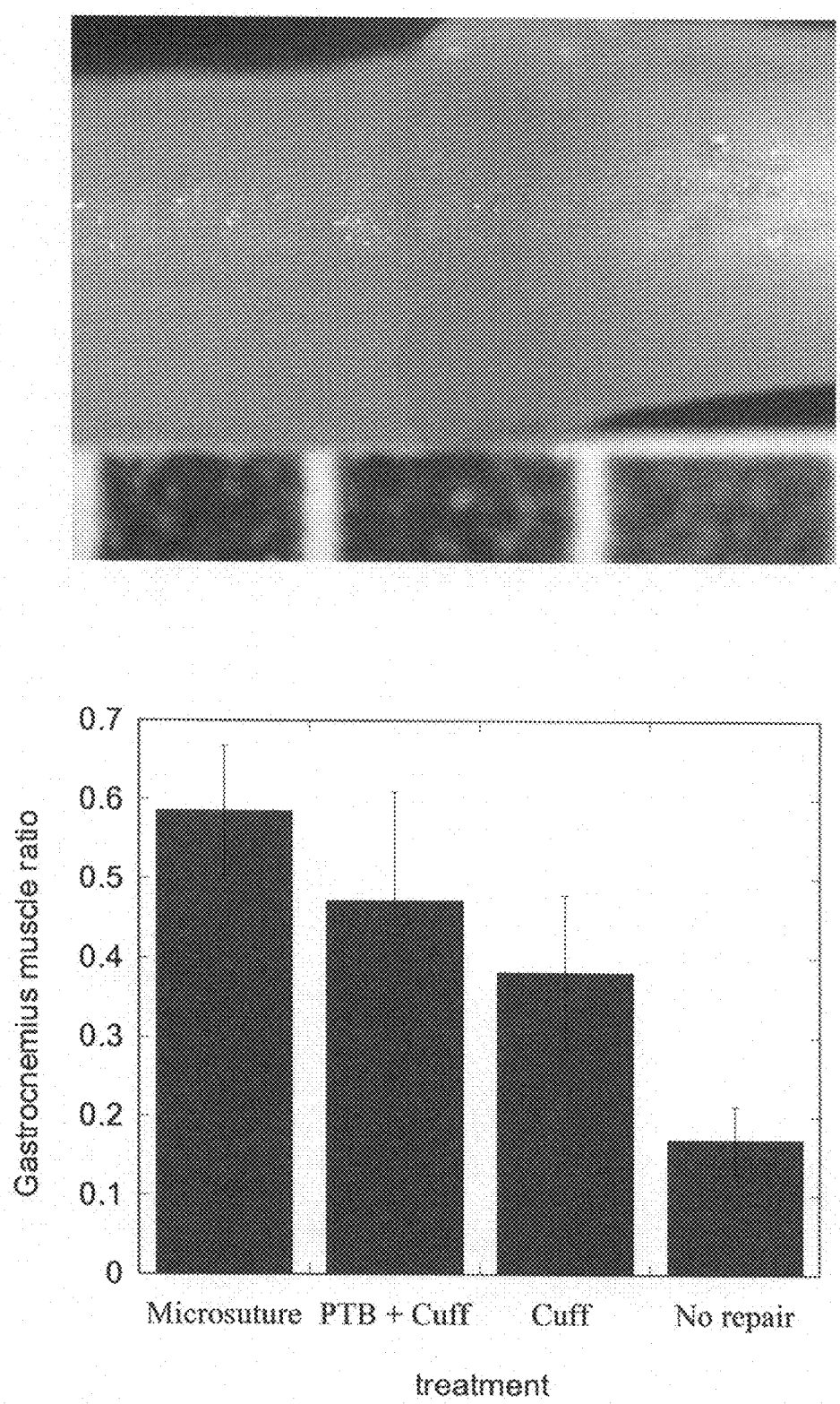
FIG. 26A shows a photograph of a sciatic nerve following epineurial cuff and PTB treatment.
FIG. 26B shows a graph of nerve repair data, showing the effects of epineurial cuff formation, and epineurial cuffs in conjunction with PTB. Nerve repair was assayed using the gastrocnemius muscle mass assay.

The results of this study are shown in FIG. 26. The methods of neural repair described herein provide an enhancement of function approaching that of conventional suture repair.

Thus, methods of the present invention provide a useful alternative to conventional surgical methods for nerve repair. Photochemical bonds can be formed that are atraumatic, instant and watertight thus minimizing any loss of neurotropic and neurotrophic factors. In addition such methods can restore the blood-nerve barrier, and minimize or eliminate any foreign-body responses and excessive scarring.

Example 15

Alternative Assays for Nerve Repair

In Example 14, a gastrocnemius muscle mass assay was used to assess nerve repair following the various treatments. Alternative assays that can also be used to assess nerve repair include tensile strength assays, histological assays, electrophysiological, and walking assays.

Tensile strength assays can be performed at post-operative days 30, 60 and 90. For example, a minimum of 4 cm of repaired sciatic nerve is removed form each animal, and a 5-0 silk suture is attached to both ends of the nerve segment immediately after dissection. The proximal nerve stump is hooked to the upper fixture of the tensile strength testing apparatus through the pre-attached suture, while the suture attached to the distal end is clamped to the lower fixture of the tensile strength testing apparatus. The nerve is adjusted to a vertical position with zero-tension before vertical tension is applied. The tensile strength testing apparatus, and the methods for testing tensile strength are the same as those previously described for skin and tendon tensile strength measurements. The force transducer records the peak force, time and the amount of deflection during the tensile test. The ultimate tensile strength of the nerve is calculated after dividing the peak force that the nerve can withstand by the cross-sectional area. Higher tensile strength measurements will typically a more effective physical repair of the nerve.

Functional analysis in the form of walking assays, as described by De Medinaceli et al. (1982), and Bain et al. (1989) can also be performed. For example, walking track analysis is performed pre-operatively and every ten days post-operatively to gauge functional recovery in the rat sciatic nerve. The animals' hind feet are dipped in dilute india ink after which they are allowed to walk down a 10 cm×40 cm corridor into a darkened box. The floor of the corridor is covered with a removable piece of paper used to record the animals' paw print. Measurements based on the print-length, toe-spread (the distance between the first and fifth toes), and the intermediary toe-spread (the distance between second and fourth toes) are used to formulate a sciatic function index (sfi). The sfi values are compared between experimental and control animals. The non-operative (right) side paw print is used to normalize SFI values between different animals.

At 90 days post-operatively, animals can be re-anesthetized and electrophysiological studies performed. The sciatic nerve is re-exposed and recording leads are placed both proximal and distal to the repair site. Stimulation and ground leads are placed and mean nerve conduction velocities are measured, giving an indication of functional nerve repair.

Histological assays to determine nerve repair can be performed also. Animals are sacrificed at a chosen day postoperatively and the muscle and neural tissues are removed. Nerve segments to be analyzed are fixed in 3% glutaraldehyde, embedded, and sectioned on a microtome. The sections are stained with hematoxylin/eosin and osmium tetroxide, and histomorphometric analysis is performed using computer-assisted quantification of digitized images from histologic slides.

Example 16

Use of Conduit Technology in Nerve Repair

Conduits consisting of sleeves of 100% collagen have been used to assist nerve repair in various animal models (Archibald et al, 1991; Li et al, 1992). The PTB methods of the present invention can be used in conjunction with collagen conduits to produce suture-less bonds. Serving as a sleeve, collagen conduits can be used to join the collagen rich epineurium of the proximal and distal ends of transected or damaged nerves. The immediate, circumferential seal formed by such methods serves to enhance the confinement of neurotrophic factors, such as nerve growth factor (NGF), and will also maximize axonal capture. Additionally inflammation and scar tissue formation is minimized.

Figure 27:
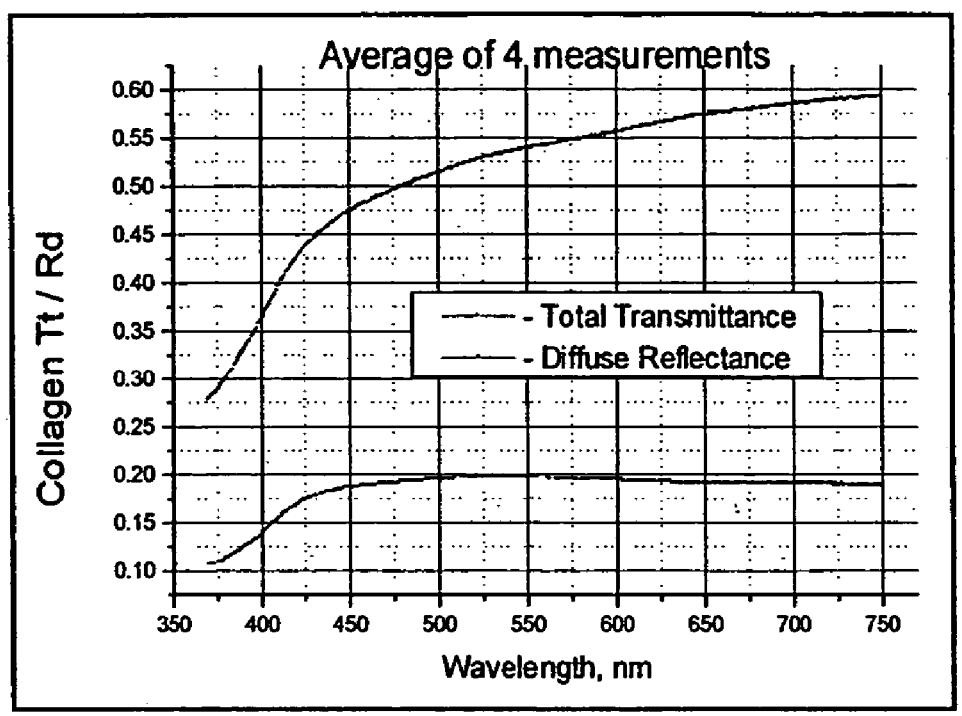
FIG. 27 shows a graph of total light transmittance and diffuse reflectance of the NeuraGen™ collagen conduit. Wavelengths of light ranging from 350 to 750 nm were tested revealing greater than 50% transmittance at ideal wavelength of 532 nm, and minimal diffuse reflectance.
Figure 28:
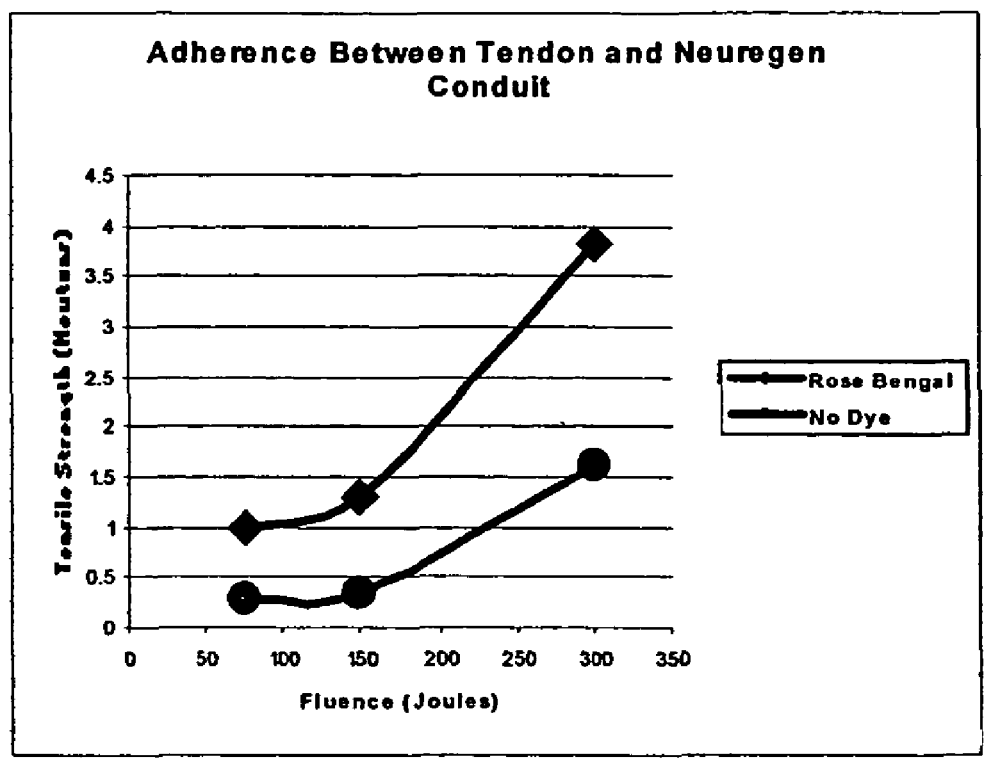
FIG. 28 shows a graph illustrating the tensile strength of the bond formed between NeuraGen™ collagen conduit and bovine tendon over a 0.25 cm² surface area. The top line (marked with squares) indicates specimens coated with Rose Bengal dye prior to laser irradiation, whereas the lower line (marked with circles) indicates laser irradiation alone, without dye treatment.

Before performing nerve repair studies, the optical suitability of 100% collagen conduits (NeuraGen™, Integra Neurosciences) for use in the PTB methods of the present invention, was assessed. Total transmittance and diffuse reflectance of light from the outside to the inside of the conduit was measured. It was found that the conduit effectively transmitted laser light at wavelengths appropriate for activation of rose bengal (RB) dye (around 532 nm). As shown in FIG. 27, at ideal wavelengths, greater than 50% of the light is transmitted through the conduit. These optical properties are similar to those of other tissues in which PTB has successfully been used in PTB with RB Additional experiments were also performed to determine the effectiveness of PTB bonding between the NeuraGen™ conduits and an animal tissue, namely bovine tendon tissue. To do this, the tensile strength of a PTB bond formed between the bovine tendon and a segment of Neuregen™ conduit was tested, using various different photoactive dyes. Both the tendon surface and the inner surface of a piece of conduit were coated with RB dye and allowed to sit in the dark for 60 seconds. The two surfaces were then thoroughly dried and pressed together to form a tendon/conduit interface of approximately $0.25 cm^2$. The construct was irradiated at 532 nm through the conduit toward the tendon/conduit interface at various fluence levels (Joules). Constructs were then pulled into tension using a tensiometer until the bond between the tendon and the conduit broke. The breaking force was measured in Newtons. A tensile strength curve based on fluence both with and without Rose Bengal dye was generated (see FIG. 28) demonstrating that an effective bond was formed at a fluence of 150-300 Joules.

Figure 29:
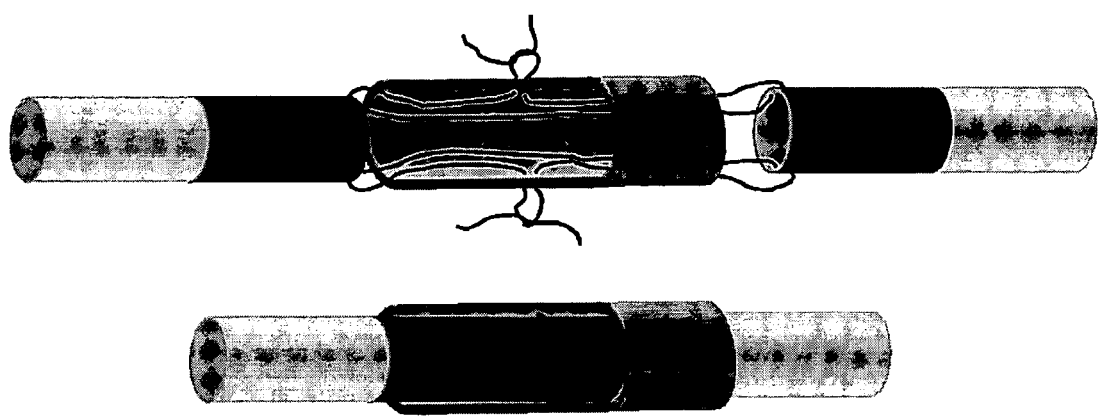
FIG. 29 shows a schematic illustration of the procedure for the formation of epineural conduits, as described in Example 16.

Having thus demonstrated the suitability of the NeuraGen™ conduit for PTB method, PTB nerve repair experiments can be performed. The sciatic nerve is transected 10 mm from the pelvic hiatus as described in the above examples. Both the proximal and the distal ends of the severed nerve are coated with a 0.1% solution of Rose Bengal dye and allowed to dry for 60 seconds. Excess dye is removed and the nerve ends are drawn into a 10 mm segment of NeuraGen™ conduit using 10-0 non-absorbable nylon monofilament suture (See FIG. 29). An argon laser with a fixed wavelength of 532 nm is used for bonding. After 1 min of application of the dye, the nerve-conduit complex is irradiated with the argon laser for 3 minutes; the nerve is then rotated 180 degrees and the opposite side is irradiated for another 3 min. The sutures are then removed from the nerve-conduit complex.

Example 17

Use of PTB in an Ex Vivo Porcine Blood Vessel Repair Model

Laser welding of blood vessels has attracted major attention in the past, however laser welding induces thermal damage in tissues causing protein denaturation. Methods of the invention avoid thermal damage while maintaining the structural integrity of the collagen, forming stronger chemical bonds.

Figure 30:
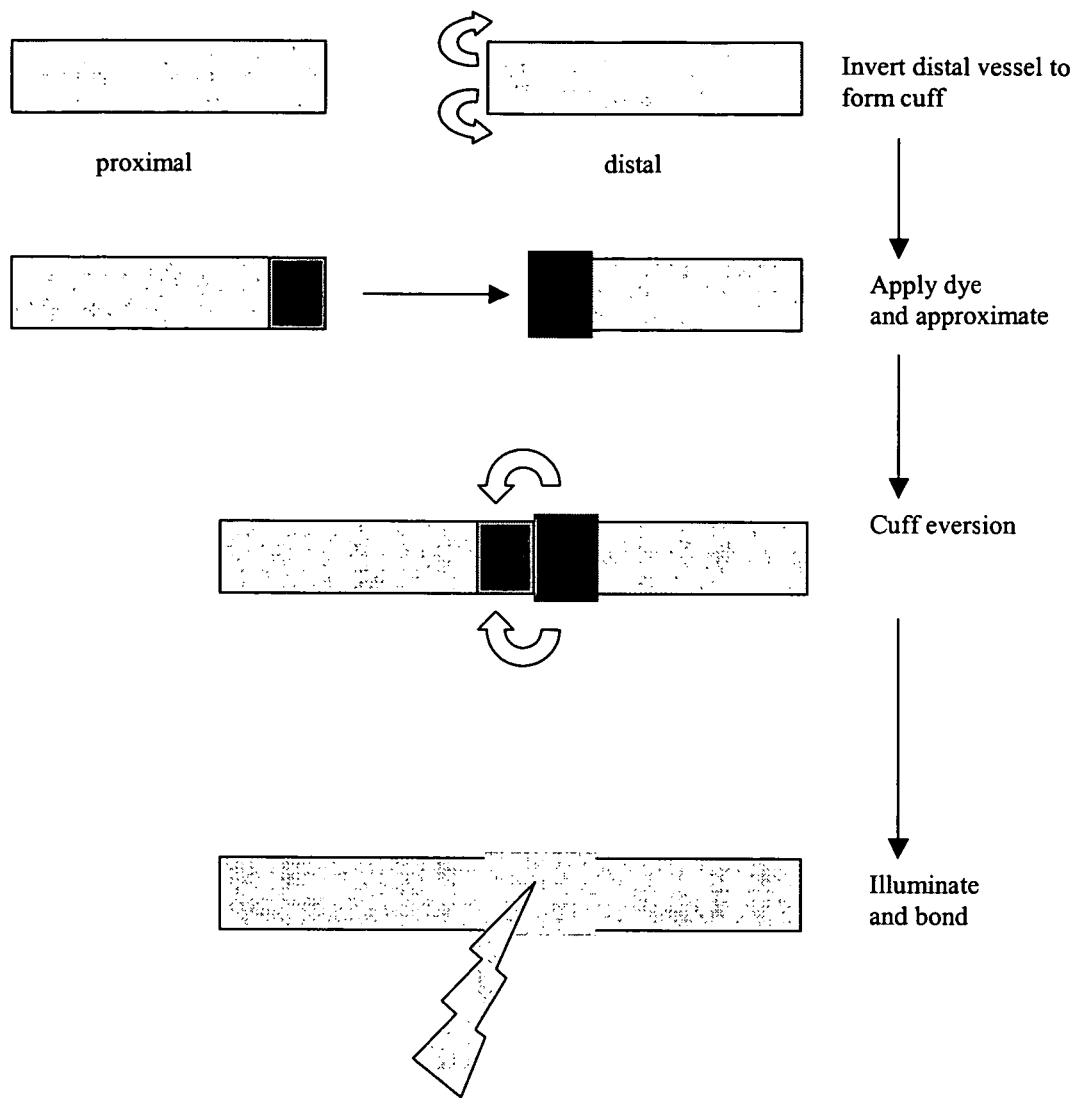
FIG. 30 shows a schematic representation of the steps involved using the "cuff" approach in PTB-mediated anastomosis of blood vessels.

In adhering segments of vascular tissue according to methods of the invention, two pieces of blood vessel are joined and photochemically bonded together to create an intimate, watertight seal. Two methods were considered to accomplish anastomosis. The "cuff" approach, which entails administration of the photoactive dye to the outer surface of the proximal vessel and the inside surface of the distal stump of the vessel. The distal stump is folded back on itself and the proximal stump brought into contact. The distal cuff is then placed over the proximal vessel to form a cuff. The overlap region in the cuff is then irradiated with visible light to bond the ends of the vessel together. FIG. 30 represents a schematic overview of the cuff approach.

Figure 31:
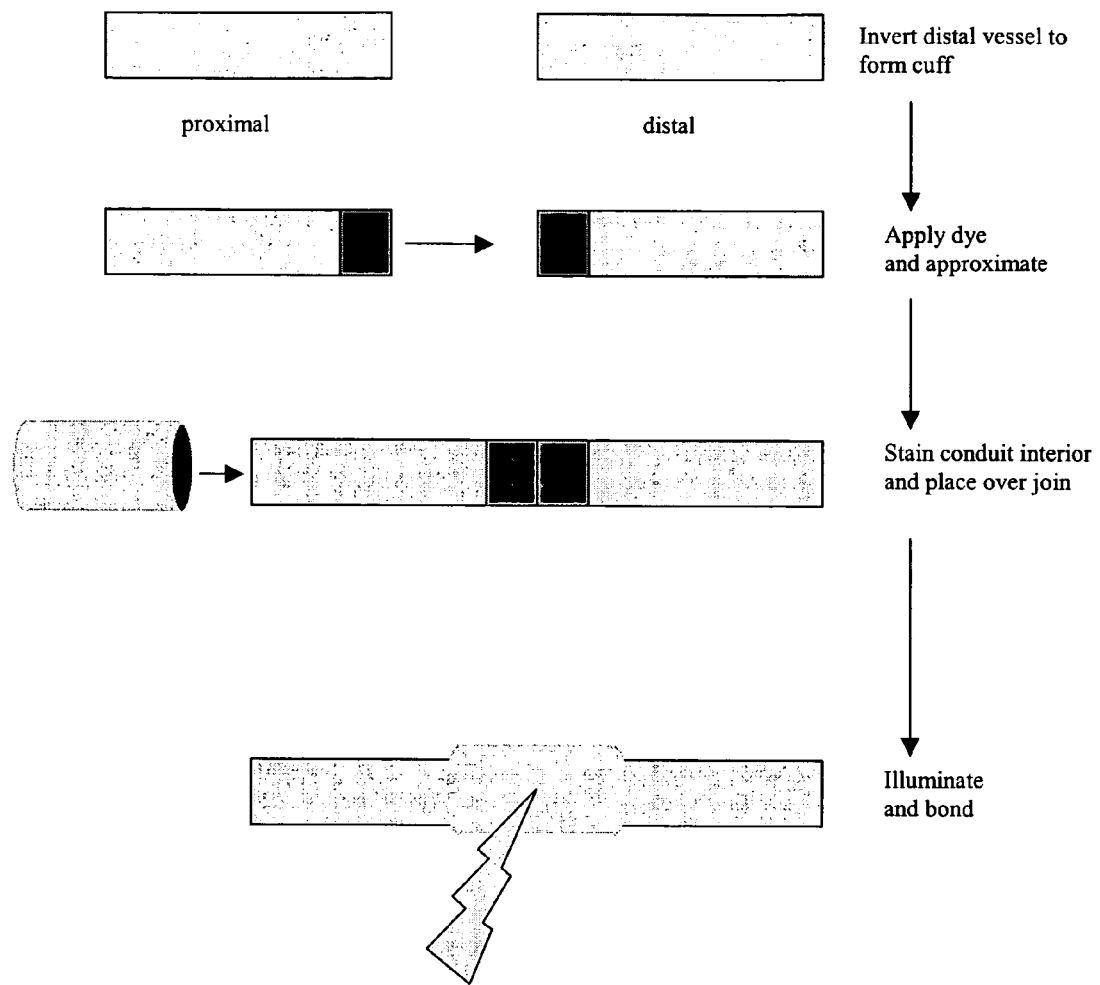
FIG. 31 shows a schematic representation of the steps involved using the "conduit" approach in PTB-mediated anastomosis of blood vessels.

FIG. 31 demonstrates the conduit approach, wherein the photoactive dye is administered to the outer surfaces of both proximal and distal vessel stumps and the inside of a tubular conduit with an inner diameter equal to the outer diameter of the blood vessel. This conduit can be of numerous materials including collagen. The conduit is placed over the approximated stumps and bonded in place using visible light.

The cuff approach was used with pig vein and arteries ex vivo. The vessels were sharply transected using a scalpel. Rose bengal at a concentration of 0.1% v/v in saline was applied to the outside surface of the proximal stump of the vessel and the inside surface of the distal vessel. The vessels were then mounted over a cylindrical glass rod that acts as support for the hollow vessels. A distal cuff was formed by folding the end of the distal end back on itself, as described above and in FIG. 30. Following apposition, the cuff was everted over the proximal vessel and the cuff region was then irradiated using 532 nm green light from a CW Nd/YAG laser (Coherent) at 0.5 W/cm2 for 2.5 minutes.

Figure 32:
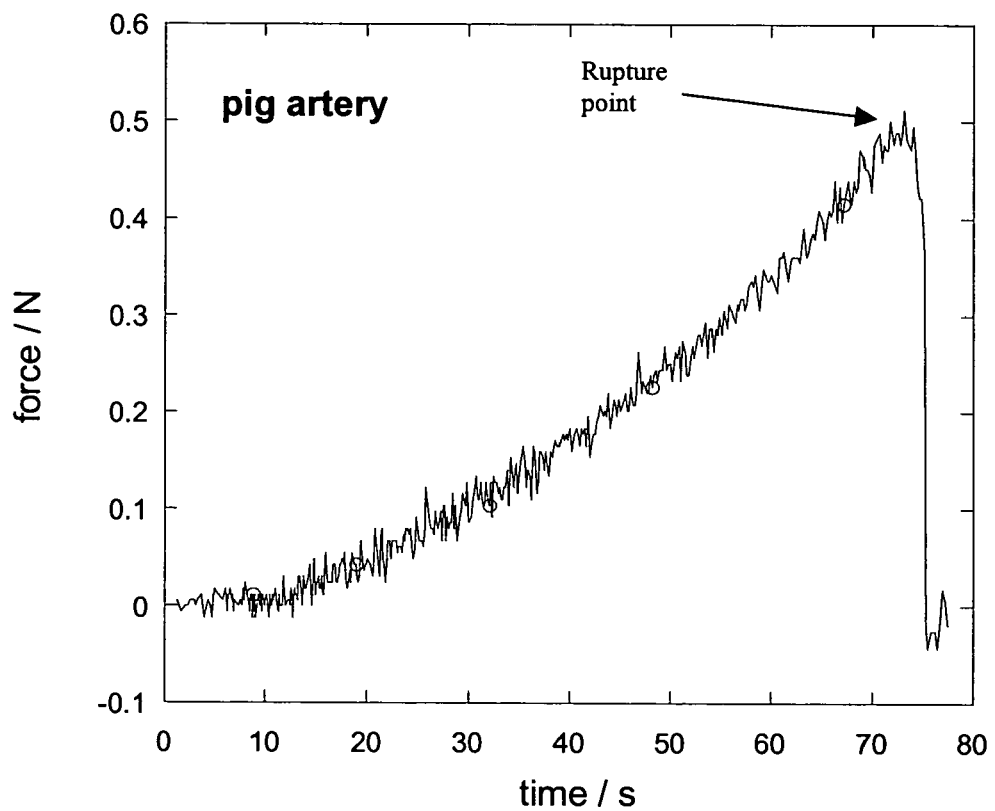
FIG. 32 shows a graph illustrating the force necessary to rupture anastomosed porcine arteries as a function of time.
Figure 33:
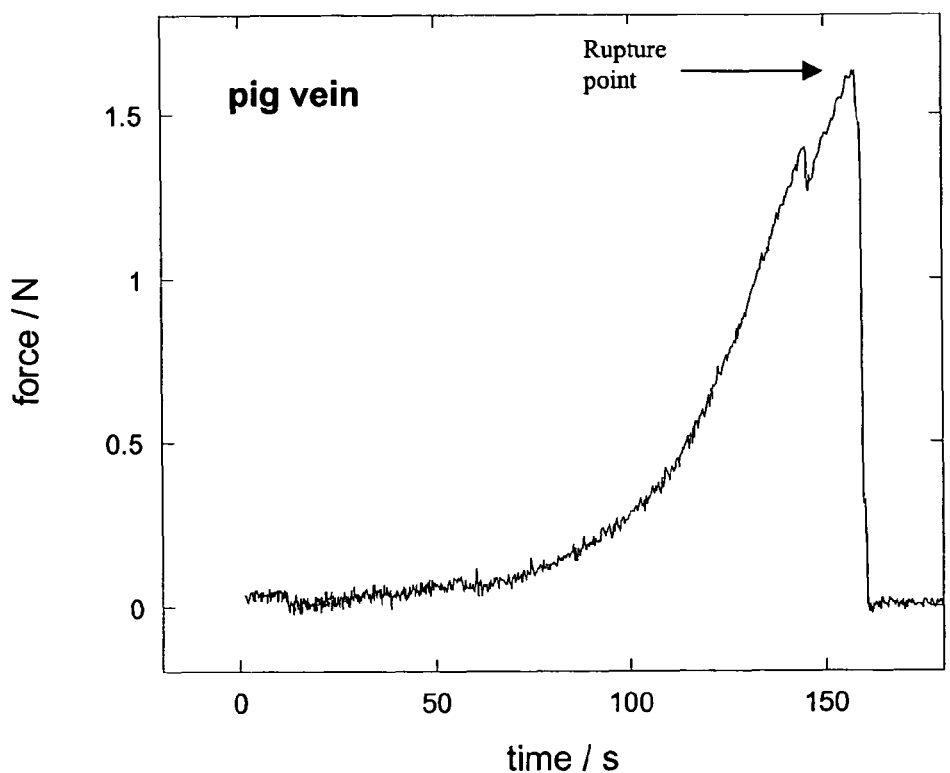
FIG. 33 shows a graph illustrating the force necessary to rupture anastomosed porcine veins as a function of time.

Following illumination, the glass support was removed and the anastomosed vessel was mounted on a strain gauge for measurement of the tensile strength of the anastomosed bond. Sutures were placed at each end of the vessel and were used to attach to the strain gauge attachments. FIG. 32 shows the force withstood by a pig artery with an inner diameter of around 3 mm before rupture took place at the site of the seal. FIG. 33 shows data collected in the same way following re-anastomosis of a pig vein of similar dimensions treated in the same way.

Very strong bonds were formed and the vessels were stretched to 3-4 times their normal length before rupture was achieved. In some cases, the bond was strong enough to withstand the force and the suture actually tore out of the end of the vessel before rupture of the seal could be achieved.

A number of embodiments of the invention have been described. Nevertheless, it will be understood that various modifications may be made without departing from the spirit and scope of the invention. Accordingly, other embodiments are within the scope of the following claims.

We claim:

1. A method for adhering neural tissue, comprising:
retracting the epineural tissue of a first neural segment and expose the endoneurium;
removing the exposed endoneurium;
contacting the inner surface of the retracted epineural tissue of the first neural segment and the outer surface of the epineural tissue of a second neural segment with at least one photosensitizer agent to form a tissue-photosensitizer complex;
joining the second neural segment with the first neural segment by placing the second neural segment within the epineurium of the first neural segment;
applying at least one suture between the first and second neural segments; and
applying electromagnetic energy to the tissue-photosensitizer complex in a manner effective to bond the first and second neural segments, thereby creating a tissue seal between the neural segments.

2. The method of claim 1, wherein at least one photosensitizer agent is selected from the group consisting of a xanthene, flavin, pyridine, phenothiazine, cyanine, and porphyrin.

3. The method of claim 2, wherein the xanthene is Rose Bengal.

4. The method of claim 1, wherein the contacting step occurs ex vivo.

5. The method of claim 1, wherein the contacting step occurs in vivo in a subject.

6. The method of claim 5, wherein the subject is a human.

7. The method of claim 1, wherein the application of electromagnetic energy to the tissue-photosensitizer complex occurs without substantial thermal tissue damage.

8. The method of claim 1, wherein the electromagnetic energy is applied at an irradiance less than 1.5 W/cm$^2$.

9. The method of claim 1, wherein the electromagnetic energy is applied at an irradiance of about 0.50 W/cm$^2$.

10. The method of claim 1, wherein the photosensitizer agent is contained in a collagen gel and wherein the gel is applied circumferentially around the first and second neural segments.

11. The method of claim 1, wherein the neural tissue is peripheral neural tissue.

12. The method of claim 1, where in the first neural segment is distal and the second neural segment is proximal to a nerve lesion.

* * * * *